United States Patent
Choi et al.

(10) Patent No.: US 10,937,970 B2
(45) Date of Patent: Mar. 2, 2021

(54) COMPOUND AND PHOTOELECTRIC DEVICE, IMAGE SENSOR AND ELECTRONIC DEVICE INCLUDING THE SAME

(71) Applicant: Samsung Electronics Co., Ltd., Suwon-si (KR)

(72) Inventors: Taejin Choi, Suwon-si (KR); Sang Mo Kim, Hwaseong-si (KR); Sung Young Yun, Suwon-si (KR); Youn Hee Lim, Hwaseong-si (KR); Katsunori Shibata, Hwaseong-si (KR); Hiromasa Shibuya, Seongnam-si (KR); Gae Hwang Lee, Seongnam-si (KR); Norihito Ishii, Suwon-si (KR); Dong-Seok Leem, Hwaseong-si (KR); Yong Wan Jin, Seoul (KR); Yeong Suk Choi, Suwon-si (KR); Jong Won Choi, Yongin-si (KR); Hyesung Choi, Seoul (KR)

(73) Assignee: Samsung Electronics Co., Ltd., Gyeonggi-do (KR)

( * ) Notice: Subject to any disclaimer, the term of this patent is extended or adjusted under 35 U.S.C. 154(b) by 0 days.

(21) Appl. No.: 16/176,422

(22) Filed: Oct. 31, 2018

(65) Prior Publication Data

US 2019/0131541 A1   May 2, 2019

(30) Foreign Application Priority Data

Oct. 31, 2017 (KR) .................. 10-2017-0143820
Oct. 31, 2018 (KR) .................. 10-2018-0132322

(51) Int. Cl.
| | | |
|---|---|---|
| H01L 51/00 | (2006.01) | |
| H01L 27/30 | (2006.01) | |
| C07D 293/10 | (2006.01) | |
| C07D 421/04 | (2006.01) | |
| C07C 225/22 | (2006.01) | |
| C07D 333/46 | (2006.01) | |
| H01L 51/44 | (2006.01) | |
| H01L 51/42 | (2006.01) | |

(52) U.S. Cl.
CPC ........ *H01L 51/0071* (2013.01); *C07C 225/22* (2013.01); *C07D 293/10* (2013.01); *C07D 333/46* (2013.01); *C07D 421/04* (2013.01); *H01L 51/006* (2013.01); *H01L 51/0052* (2013.01); *H01L 51/0053* (2013.01); *H01L 51/0059* (2013.01); *H01L 51/0061* (2013.01); *H01L 51/0067* (2013.01); *H01L 51/0068* (2013.01); *C07C 2603/12* (2017.05); *H01L 27/307* (2013.01); *H01L 51/0058* (2013.01); *H01L 51/4253* (2013.01); *H01L 51/44* (2013.01)

(58) Field of Classification Search
CPC ............ C07C 2603/12; H01L 51/0053; H01L 51/0067; H01L 51/0071; H01L 51/0059; C07D 333/46; C07D 421/04; C07D 293/10

USPC .......................................................... 257/40
See application file for complete search history.

(56) References Cited

U.S. PATENT DOCUMENTS

| | | | |
|---|---|---|---|
| 6,689,491 | B1 | 2/2004 | Nii et al. |
| 6,821,591 | B2 | 11/2004 | Gord et al. |
| 8,513,651 | B2 | 8/2013 | Mitsui et al. |
| 8,525,577 | B2 | 9/2013 | Yofu et al. |
| 9,666,810 | B2 | 5/2017 | Yun et al. |
| 9,786,847 | B2 | 10/2017 | Lim et al. |
| 9,941,477 | B2 | 4/2018 | Choi et al. |
| 2005/0065351 | A1 | 3/2005 | Nii et al. |
| 2016/0126470 | A1 | 5/2016 | Ro et al. |
| 2017/0092868 | A1 | 3/2017 | Yagi et al. |
| 2017/0213973 | A1 | 7/2017 | Yun et al. |
| 2017/0294589 | A1 | 10/2017 | Shibuya et al. |
| 2017/0331050 | A1 | 11/2017 | Yagi et al. |
| 2017/0352811 | A1 | 12/2017 | Choi et al. |

FOREIGN PATENT DOCUMENTS

| | | |
|---|---|---|
| CN | 106220619 A | 12/2016 |
| CN | 106279203 A | 1/2017 |
| JP | 2000297068 A | 10/2000 |
| JP | 2004302207 A | 10/2004 |
| JP | 2005123033 A | 5/2005 |
| JP | 2007095584 A | 4/2007 |

(Continued)

OTHER PUBLICATIONS

U.S. Appl. No. 16/835,934, filed Mar. 2020, Choi et al., H01L 51/00.*

(Continued)

*Primary Examiner* — Mark L Shibuya
*Assistant Examiner* — Ebenezer O Sackey
(74) *Attorney, Agent, or Firm* — Harness, Dickey & Pierce, P.L.C.

(57) ABSTRACT

A compound of Chemical Formula 1, and a photoelectric device, an image sensor, and an electronic device including the same are disclosed:

[Chemical Formula 1]

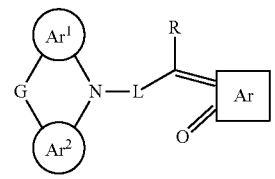

In Chemical Formula 1, each substituent is the same as defined in the detailed description.

26 Claims, 9 Drawing Sheets

(56) References Cited

FOREIGN PATENT DOCUMENTS

| JP | 2009205890 A | 9/2009 |
|---|---|---|
| JP | 2009212035 A | 9/2009 |
| JP | 2011150874 A | 8/2011 |
| JP | 2012214738 A | 11/2012 |
| JP | 2013122912 A | 6/2013 |
| KR | 10-0477983 B1 | 3/2005 |
| KR | 10-2010-0048210 A | 5/2010 |
| KR | 10-0957783 B1 | 5/2010 |
| KR | 10-2010-0131390 A | 12/2010 |
| KR | 10-2012-0122847 A | 11/2012 |
| KR | 10-2014-0009939 A | 1/2014 |
| KR | 10-2016-0046567 A | 4/2016 |
| KR | 10-1608281 B1 | 4/2016 |
| KR | 10-2016-0052448 A | 5/2016 |
| KR | 10-2016-0062527 A | 6/2016 |
| KR | 10-2017-0037390 A | 4/2017 |
| KR | 10-2017-0060488 A | 6/2017 |
| KR | 10-2017-0114839 A | 10/2017 |
| KR | 10-2017-0126753 A | 11/2017 |
| KR | 10-2017-0137648 A | 12/2017 |
| WO | WO-2010/050779 A1 | 5/2010 |

OTHER PUBLICATIONS

Kim, S. et al., "Synthesis and Optical Chromic Properties of New Barbituric Acid based Dye Molecules Having Push-π-Pull System," Molecular Crystals and Liquid Crystals, vol. 550, pp. 240-249, (2011).

Kim, B. et al., "Synthesis and Solvatofluorochromism Behaviors on Intramolecular Charge Transfer System of Novel D-π-A Dyes," Molecular Crystals and Liquid Crystals, vol. 563, pp. 257-271, (2012).

Seo, H. et al.. "Color Sensors with Three Vertically Stacked Organic Photodetectors," Japanese Journal of Applied Physics, vol. 46, No. 49, (2007), pp. L1240-L1242.

Aihara, S. et al., "Stacked Image Sensor With Green- and Red-Sensitive Organic Photoconductive Films Applying Zinc Oxide Thin-Film Transistors to a Signal Readout Circuit," IEEE Transactions on Electron Devices, vol. 56, No. 11, (Nov. 2009), pp. 2570-2576.

Ihama, M. et al., "CMOS Image Sensor with a Thin Overlaid Panchromatic Organic Photoconductive Layer for Sensors with Reduced Pixel Size," IDW '09, INP 1-4, pp. 2123-2126, 2009.

Kim, S. et al., "Synthesis and Optical Chromic Properties of New Barbituric Acid based Dye Molecules Having Push-π-Pull System," Molecular Crystals and Liquid Crystals, vol. 550, pp. 240-249, (2011).

Kim. B. et al., "Synthesis and Solvatofluorochromism Behaviors on Intramolecular Charge Transfer System of Novel D-π-A Dyes," Molecular Crystals and Liquid Crystals, vol. 563, pp. 257-271, (2012).

* cited by examiner

COMPOUND AND PHOTOELECTRIC DEVICE, IMAGE SENSOR AND ELECTRONIC DEVICE INCLUDING THE SAME

CROSS-REFERENCE TO RELATED APPLICATION

This application claims priority to Korean Patent Application Nos. 10-2017-0143820 and 10-2018-0132322, filed in the Korean Intellectual Property Office on Oct. 31, 2017 and Oct. 31, 2018, respectively and all the benefits accruing therefrom under 35 U.S.C. § 119, the entire contents of which are incorporated herein by reference.

BACKGROUND

1. Field

Example embodiments relate to a compound and a photoelectric device, an image sensor, and an electronic device including the same.

2. Description of the Related Art

A photoelectric device converts light into an electrical signal using photoelectric effects, it may include a photodiode, a phototransistor, and the like, and it may be applied to an image sensor, a solar cell, an organic light emitting diode, and the like.

An image sensor including a photodiode requires relatively high resolution and thus a smaller pixel. At present, a silicon photodiode is widely used. In some cases, a silicon photodiode exhibits may have deteriorated sensitivity because of a relatively small absorption area due to relatively small pixels. Accordingly, an organic material that is capable of replacing silicon has been researched.

An organic material may have a relatively high extinction coefficient and may selectively absorb light in a particular wavelength region depending on a molecular structure, and thus may simultaneously replace a photodiode and a color filter and resultantly improve sensitivity and contribute to relatively high integration.

SUMMARY

Example embodiments provide a compound that selectively absorbs light in a green wavelength region and has improved thermal stability.

Example embodiments also provide a photoelectric device (e.g., organic photoelectric device), an image sensor, and an electronic device including the compound.

According to example embodiments, a compound represented by Chemical Formula 1 is provided.

[Chemical Formula 1]

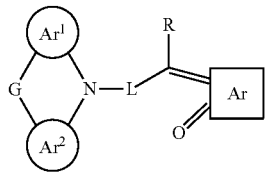

In Chemical Formula 1,

Ar may be one of a substituted or unsubstituted 5-membered aromatic ring group, a substituted or unsubstituted 6-membered aromatic ring group, and a condensed ring of two or more of the foregoing ring groups, R may be one of hydrogen, a substituted or unsubstituted C1 to C30 alkyl group, a substituted or unsubstituted C1 to C30 alkoxy group, a substituted or unsubstituted C6 to C30 aryl group, a substituted or unsubstituted C3 to C30 heteroaryl group, a halogen, a cyano group (—CN), a cyano-containing group, or a combination thereof, L may be one of a substituted or unsubstituted C6 to C16 aromatic ring group or a substituted or unsubstituted C3 to C13 N-containing heteroaromatic ring group, $Ar^1$ and $Ar^2$ may independently be one of a substituted or unsubstituted C6 to C30 aryl group or a substituted or unsubstituted C3 to C30 heteroaryl group, and G may be one of —Se—, —N=, —$NR^a$—, —$SiR^bR^c$—, —$SiR^{bb}R^{cc}$—, —$GeR^dR^e$—, or —$GeR^{dd}R^{ee}$— wherein $R^a$, $R^b$, $R^c$, $R^d$, and $R^e$ are independently one of hydrogen, a halogen, or a substituted or unsubstituted C1 to C10 alkyl group, wherein $R^{bb}$, $R^{cc}$, $R^{dd}$ and $R^{ee}$ may independently be one of a substituted or unsubstituted C1 to C10 alkyl group, or a substituted or unsubstituted C6 to C10 aryl group, $R^{bb}$ and $R^{cc}$ may be linked with each other to provide a ring structure, and $R^{dd}$ and $R^{ee}$ may be linked with each other to provide a ring structure.

In some example embodiments, in Chemical Formula 1, L may be one of linkers represented by Chemical Formula 2-1.

[Chemical Formula 2-1]

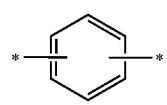

(1)

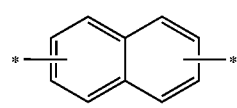

(2)

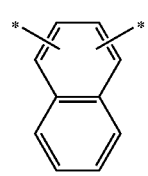

(3)

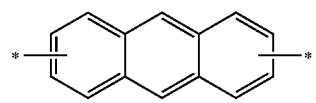

(4)

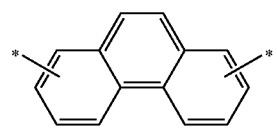

(5)

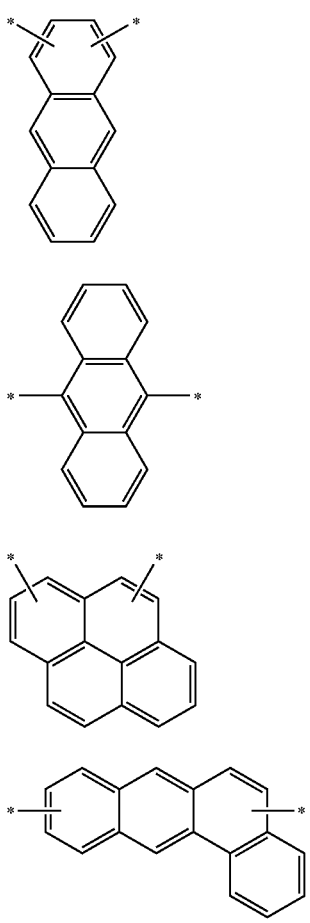

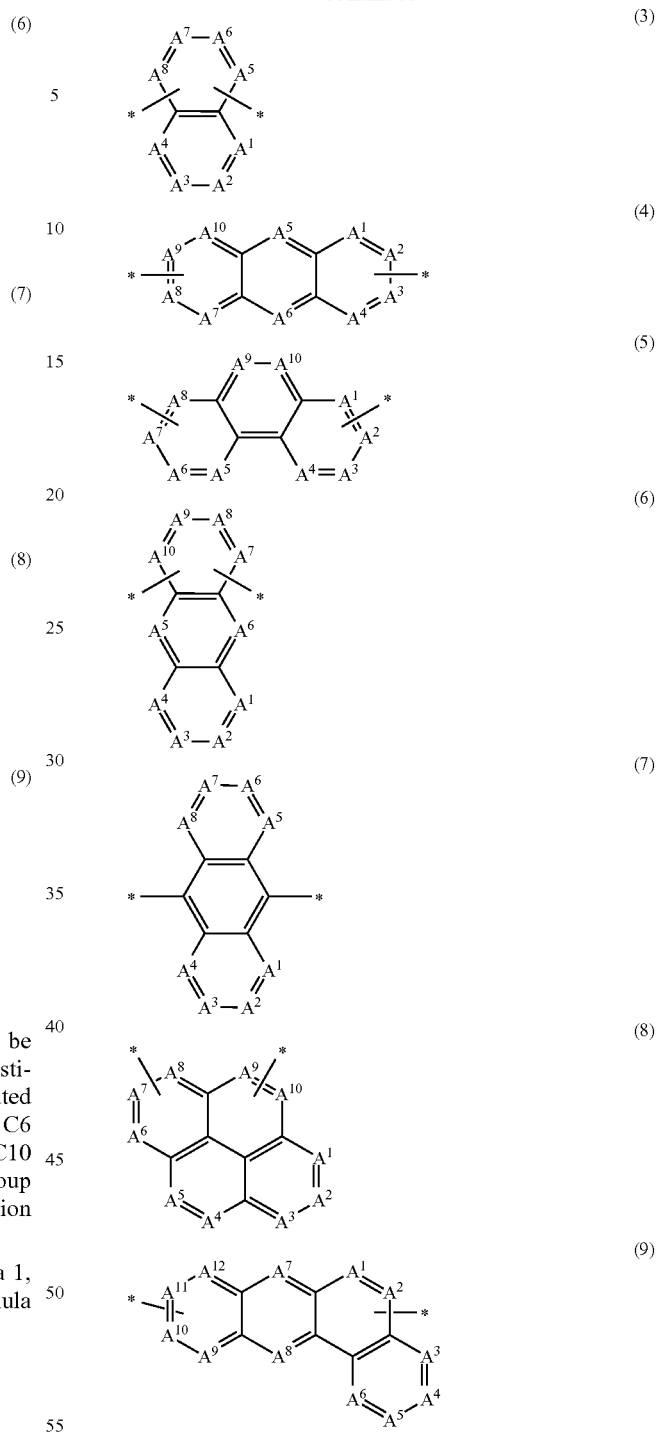

In Chemical Formula 2-1, hydrogen of —CH— in each aromatic ring may be optionally replaced by a group of a substituted or unsubstituted C1 to C20 alkyl group, a substituted or unsubstituted C1 to C20 alkoxy group, a substituted or unsubstituted C6 to C10 aryl group, a substituted or unsubstituted C4 to C10 heteroaryl group, a halogen (F, Cl, Br, or I), a cyano group (—CN), a cyano-containing group, or a combination thereof.

In some example embodiments, in Chemical Formula 1, L may be one of linkers represented by Chemical Formula 2-2.

[Chemical Formula 2-2]

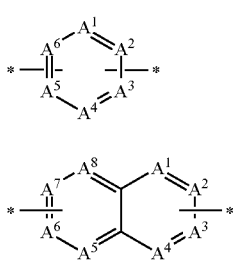

In Chemical Formula 2-2, $A^1$ to $A^{12}$ may independently be N or $CR^a$ (wherein, $R^a$ may be one of hydrogen, a substituted or unsubstituted C1 to C20 alkyl group, a substituted or unsubstituted C1 to C20 alkoxy group, a substituted or unsubstituted C6 to C10 aryl group, a substituted or unsubstituted C4 to C10 heteroaryl group, a halogen (F, Cl, Br, or I), a cyano group (—CN), a cyano-containing group, or a combination thereof), one to three of $A^1$ to $A^6$ in Chemical Formula (1) may be N, one to three of $A^1$ to $A^8$ in Chemical Formulae (2) and (3) may be N, one to three of $A^1$ to $A^{10}$ in Chemical Formulae (4) and (6) may be N, one to three of $A^1$ to $A^8$ in Chemical Formula (7) may be N, one to three of $A^1$ to $A^9$ in Chemical Formula (8) may be N, and one to three of $A^1$ to $A^{12}$ in Chemical Formula (9) may be N.

In some example embodiments, in Chemical Formula 1, L may be one of linkers represented by Chemical Formula 3.

[Chemical Formula 3]

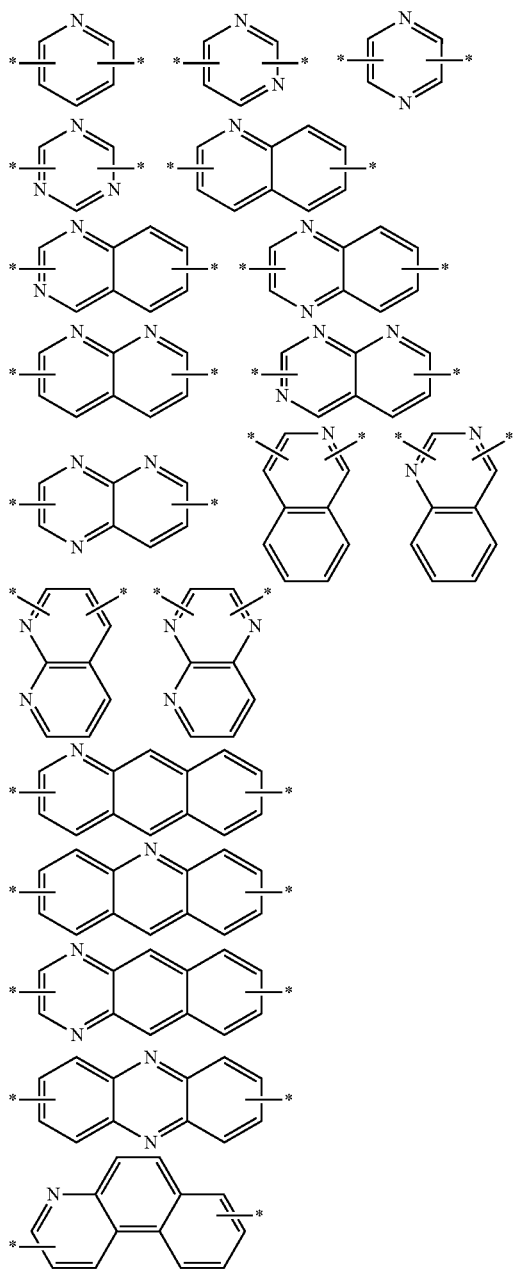

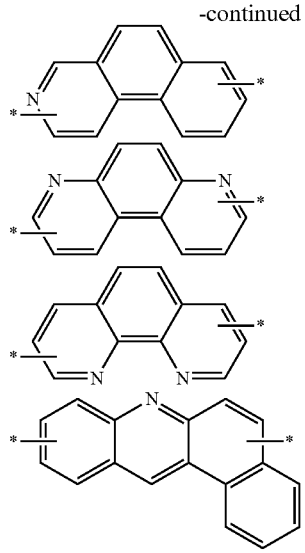

In Chemical Formula 3, hydrogen of —CH— in each aromatic ring may be optionally replaced by a group of a substituted or unsubstituted C1 to C20 alkyl group, a substituted or unsubstituted C1 to C20 alkoxy group, a substituted or unsubstituted C6 to C10 aryl group, a substituted or unsubstituted C4 to C10 heteroaryl group, a halogen (F, Cl, Br, or I), a cyano group (—CN), a cyano-containing group, or a combination thereof.

In some example embodiments, in Chemical Formula 1, at least one of $Ar^1$ and $Ar^2$ may include a heteroatom at the No. 1 position and the heteroatom may be one of nitrogen (N), sulfur (S), and selenium (Se).

In some example embodiments, in Chemical Formula 1, the ring group including $Ar^1$ and $Ar^2$ may be one of Chemical Formula 4.

[Chemical Formula 4]

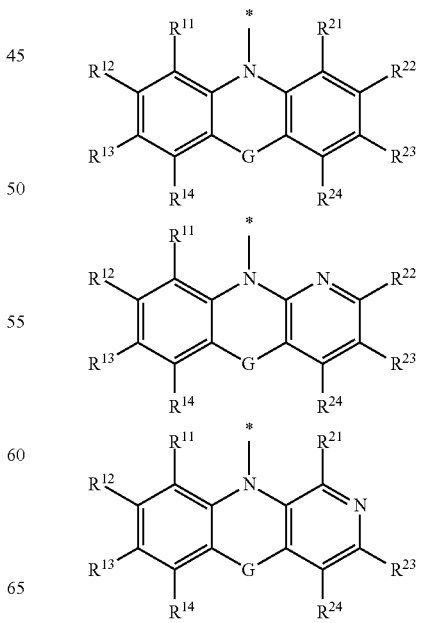

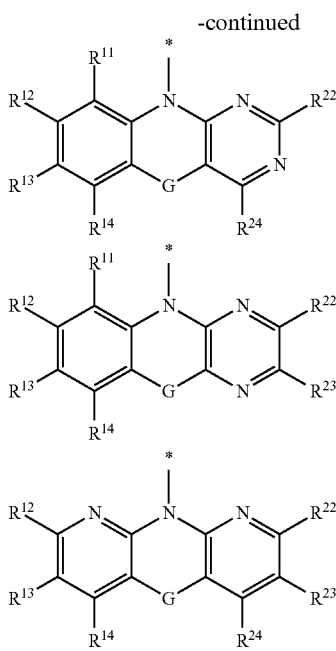

In Chemical Formula 4,

G may be one of —Se—, —N=, —NR$^a$—, —SiR$^b$R$^c$—, —SiR$^{bb}$R$^{cc}$—, —GeR$^d$R$^e$—, or —GeR$^{dd}$R$^{ee}$— wherein R$^a$, R$^b$, R$^c$, R$^d$, and R$^e$ are independently one of hydrogen, a halogen, or a substituted or unsubstituted C1 to C10 alkyl group, wherein R$^{bb}$, R$^{cc}$, R$^{dd}$ and R$^{ee}$ may independently be one of a substituted or unsubstituted C1 to C10 alkyl group, or a substituted or unsubstituted C6 to C10 aryl group, R$^{bb}$ and R$^{cc}$ may be linked with each other to provide a ring structure, and R$^{dd}$ and R$^{ee}$ may be linked with each other to provide a ring structure, and R$^{11}$ to R$^{14}$ and R$^{21}$ to R$^{24}$ may independently be one of hydrogen, a substituted or unsubstituted C1 to C30 alkyl group, a substituted or unsubstituted C6 to C30 aryl group, a substituted or unsubstituted C3 to C30 heteroaryl group, a halogen, a cyano group (—CN), a cyano-containing group, or a combination thereof, two adjacent groups of R$^{11}$ to R$^{14}$ may be linked with each other to provide a 5-membered aromatic ring group or a 6-membered aromatic ring group, or two adjacent groups of R$^{11}$ to R$^{14}$ may not be linked with each other to provide a 5-membered aromatic ring or a 6-membered aromatic ring, and two adjacent groups of R$^{21}$ to R$^{24}$ may be linked with each other to provide a 5-membered aromatic ring group or a 6-membered aromatic ring group, or two adjacent groups of R$^{21}$ to R$^{24}$ may not be linked with each other to provide a 5-membered aromatic ring or a 6-membered aromatic ring.

In some example embodiments, in Chemical Formula 1, an Ar-containing ring group may be represented by Chemical Formula 5.

[Chemical Formula 5]

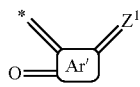

In Chemical Formula 5,

Ar' may be one of a substituted or unsubstituted 5-membered aromatic ring group, a substituted or unsubstituted 6-membered aromatic ring group, and a condensed ring of two or more of the foregoing ring groups, and $Z^1$ may be O or CR$^a$R$^b$, wherein R$^a$ and R$^b$ may independently be one of hydrogen, a substituted or unsubstituted C1 to C10 alkyl group, a cyano group, or a cyano-containing group, provided that at least one of R$^a$ and R$^b$ is a cyano group or a cyano-containing group.

In some example embodiments, in Chemical Formula 1, Ar-containing ring group may be represented by one of Chemical Formulae 5-1 to 5-6.

[Chemical Formula 5-1]

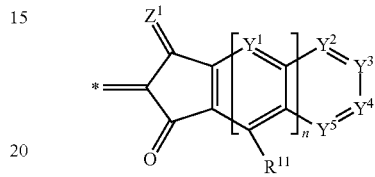

In Chemical Formula 5-1, $Z^1$ may be O or CR$^a$R$^b$ (wherein R$^a$ and R$^b$ may independently be one of hydrogen, a substituted or unsubstituted C1 to C10 alkyl group, a cyano group, or a cyano-containing group, provided that at least one of R$^b$ and R$^c$ is a cyano group or a cyano-containing group), $Y^1$ to $Y^5$ may be the same or different and may be one of N and CR$^c$, wherein R$^c$ may be one of hydrogen, a substituted or unsubstituted C1 to C30 alkyl group, a substituted or unsubstituted C1 to C30 alkoxy group, a substituted or unsubstituted C6 to C30 aryl group, a substituted or unsubstituted C4 to C30 heteroaryl group, a halogen, a cyano group, a cyano-containing group, or a combination thereof, R$^{11}$ may be one of hydrogen, a substituted or unsubstituted C1 to C30 alkyl group, a substituted or unsubstituted C6 to C30 aryl group, a substituted or unsubstituted C4 to C30 heteroaryl group, a halogen, a cyano group (—CN), a cyano-containing group, or a combination thereof, n is 0, 1 or 2, and

* indicates a linking position.

[Chemical Formula 5-2]

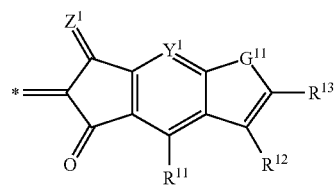

In Chemical Formula 5-2, $Y^1$ may be N or CR$^c$, wherein R$^c$ may be one of hydrogen, a substituted or unsubstituted C1 to C30 alkyl group, a substituted or unsubstituted C1 to C30 alkoxy group, a substituted or unsubstituted C6 to C30 aryl group, a substituted or unsubstituted C4 to C30 heteroaryl group, a halogen, a cyano group, a cyano-containing group, or a combination thereof, R$^{11}$ to R$^{13}$ may be the same or different and may be one of hydrogen, a substituted or unsubstituted C1 to C30 alkyl group, a substituted or unsubstituted C6 to C30 aryl group, a substituted or unsubstituted C4 to C30 heteroaryl group, a halogen, a cyano group (—CN), a cyano-containing group, or a combination thereof, and G$^{11}$ may be one of S, Se, GeR$^x$R$^y$, or Te, wherein R$^x$ and R$^y$ may be the same or different and may independently be one of hydrogen, a halogen, a substituted or unsubstituted C1 to C10 alkyl group, or a substituted or unsubstituted C6 to C10 aryl group.

[Chemical Formula 5-3]

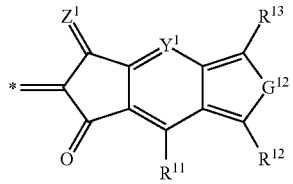

In Chemical Formula 5-3,

Y$^1$ may be N or CR$^c$, wherein R$^c$ may be one of hydrogen, a substituted or unsubstituted C1 to C30 alkyl group, a substituted or unsubstituted C1 to C30 alkoxy group, a substituted or unsubstituted C6 to C30 aryl group, a substituted or unsubstituted C4 to C30 heteroaryl group, a halogen, a cyano group, a cyano-containing group, or a combination thereof, R$^{11}$ to R$^{13}$ may be the same or different and may be one of hydrogen, a substituted or unsubstituted C1 to C30 alkyl group, a substituted or unsubstituted C6 to C30 aryl group, a substituted or unsubstituted C4 to C30 heteroaryl group, a halogen, a cyano group (—CN), a cyano-containing group, or a combination thereof, and G$^{12}$ may be one of S, Se, GeR$^x$R$^y$, or Te, wherein R$^x$ and R$^y$ are the same or different and may independently be one of hydrogen, a halogen, a substituted or unsubstituted C1 to C10 alkyl group, or a substituted or unsubstituted C6 to C10 aryl group.

[Chemical Formula 5-4]

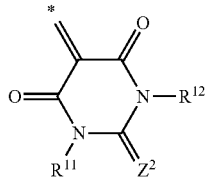

In Chemical Formula 5-4,

Z$^2$ may be one of O, S, Se, Te, or C(R$^d$)(CN), wherein R$^d$ may be one of hydrogen, a cyano group (—CN), or a C1 to C10 alkyl group, R$^{11}$ and R$^{12}$ may independently be one of hydrogen, a substituted or unsubstituted C1 to C30 alkyl group, a substituted or unsubstituted C1 to C30 alkoxy group, a substituted or unsubstituted C6 to C30 aryl group, a substituted or unsubstituted C4 to C30 heteroaryl group, a halogen, a cyano group (—CN), or a combination thereof, and

* indicates a linking position.

[Chemical Formula 5-5]

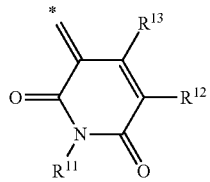

In Chemical Formula 5-5,

R$^{11}$ to R$^{13}$ may independently be one of hydrogen, a substituted or unsubstituted C1 to C30 alkyl group, a substituted or unsubstituted C1 to C30 alkoxy group, a substituted or unsubstituted C6 to C30 aryl group, a substituted or unsubstituted C4 to C30 heteroaryl group, a halogen, a cyano group (—CN), a cyano-containing group, or a combination thereof, and

* indicates a linking position.

[Chemical Formula 5-6]

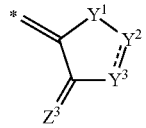

In Chemical Formula 5-6,

Z$^3$ may be one of O, S, Se, Te, or C(R$^d$)(CN), wherein R$^d$ may be one of hydrogen, a cyano group (—CN), or a C1 to C10 alkyl group, Y$^1$ may be one of O, S, Se, Te, or GeR$^e$R$^f$ (wherein R$^e$ and R$^f$ are the same or different and may independently be one of hydrogen, a halogen, a substituted or unsubstituted C1 to C10 alkyl group, or a substituted or unsubstituted C6 to C10 aryl group), Y$^2$ may be one of CR$^h$, C=O, C=S, or C=(CR$^i$)(CN), Y$^3$ may be N or NR$^g$, if Z$^3$ is not oxygen (O), Y$^2$ may be C=O, R$^g$, R$^h$, and R$^i$ may independently be one of hydrogen, a substituted or unsubstituted C1 to C30 alkyl group, a substituted or unsubstituted C1 to C30 alkoxy group, a substituted or unsubstituted C6 to C30 aryl group, a substituted or unsubstituted C4 to C30 heteroaryl group, a halogen, a cyano group (—CN), a cyano-containing group, or a combination thereof, if Y$^2$ is CR$^h$ or C=(CR$^i$)(CN) and Y$^3$ is NR$^g$, Y$^2$ and Y$^3$ may be linked with each other to provide a Y$^2$-Y$^3$-containing fused ring with the structure (a pentagonal ring) represented by Chemical Formula 5-6 or may not be a part of a Y$^2$-Y$^3$-containing fused ring with the structure represented by Chemical Formula 5-6, and

* indicates a linking position.

In some example embodiments, the compound may exhibit a light absorption curve having a full width at half maximum (FWHM) of about 50 nm to about 120 nm, in a thin film state.

In some example embodiments, a temperature (deposition temperature) at which 50 wt % of an initial weight of the compound is lost may be greater than or equal to about 280° C.

In some example embodiments, a difference between a melting point of the compound and a temperature (deposition temperature) at which 50 wt % of an initial weight of the compound is lost may be greater than or equal to about 10° C.

According to another embodiment, a photoelectric device includes a first electrode and a second electrode facing each other and an active layer between the first electrode and the second electrode. The active layer may include the compound represented by Chemical Formula 1.

In some example embodiments, the active layer may exhibit a light absorption curve having a full width at half maximum (FWHM) of about 50 nm to about 120 nm, in a thin film state.

According to another embodiment, an image sensor includes the photoelectric device.

In some example embodiments, the image sensor may include a semiconductor substrate integrated with a plurality of first photo-sensing devices sensing light in a blue wavelength region and a plurality of second photo-sensing devices sensing light in a red wavelength region, and the photoelectric device may be on the semiconductor substrate and selectively sensing light in a green wavelength region.

In some example embodiments, the first photo-sensing device and the second photo-sensing device may be stacked in a vertical direction in the semiconductor substrate.

In some example embodiments, the image sensor may further include a color filter layer including a blue filter selectively transmitting light in a blue wavelength region and a red filter selectively transmitting light in a red wavelength region.

The image sensor may include a green photoelectric device of the photoelectric device, a blue photoelectric device selectively absorbing light in a blue wavelength region, and a red photoelectric device selectively absorbing light in a red wavelength region that are stacked.

According to another embodiment, an electronic device includes the image sensor.

The compound may selectively absorb light in a desired (and/or alternatively predetermined) wavelength region and have improved thermal stability, and may improve processibility during the manufacturing of a photoelectric device, an image sensor, and an electronic device.

DETAILED DESCRIPTION

Figure 1:
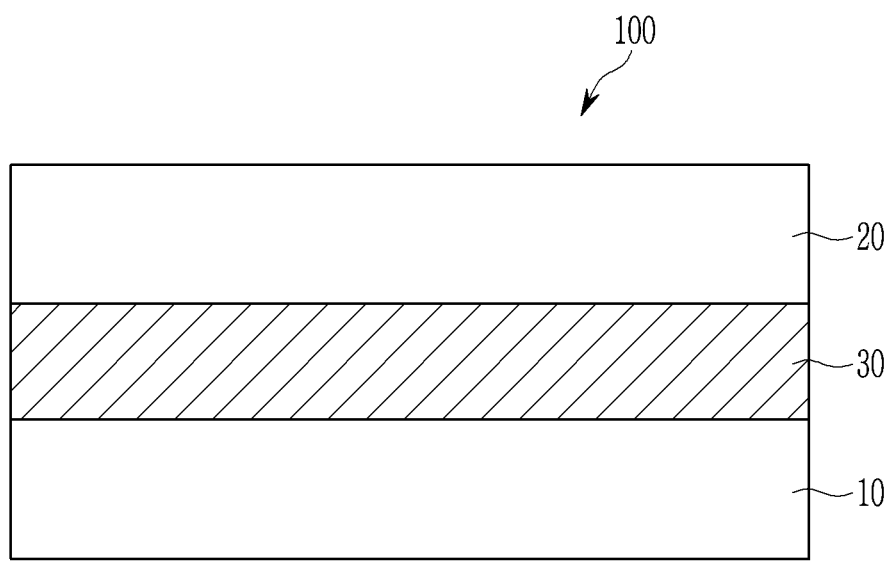
FIG. 1 is a cross-sectional view showing a photoelectric device according to an embodiment.

Example embodiments will hereinafter be described in detail, and may be easily performed by a person having an ordinary skill in the related art. However, this disclosure may be embodied in many different forms and is not to be construed as limited to the example embodiments set forth herein.

In the drawings, the thickness of layers, regions, etc., are exaggerated for clarity. Like reference numerals designate like elements throughout the specification. It will be understood that when an element such as a layer, film, region, or plate is referred to as being "on" another element, it can be directly on the other element or intervening elements may also be present. In contrast, when an element is referred to as being "directly on" another element, there are no intervening elements present.

In the drawings, parts having no relationship with the description are omitted for clarity of the embodiments, and the same or similar constituent elements are indicated by the same reference numeral throughout the specification.

Expressions such as "at least one of," when preceding a list of elements (e.g., A, B, and C), modify the entire list of elements and do not modify the individual elements of the list. For example, "at least one of A, B, and C," "at least one of A, B, or C," "one of A, B, C, or a combination thereof," and "one of A, B, C, and a combination thereof," respectively, may be construed as covering any one of the following combinations: A; B; A and B; A and C; B and C; and A, B, and C."

As used herein, when specific definition is not otherwise provided, "substituted" may refer to replacement of a hydrogen valence halogen atom (F, Br, Cl, or I), a hydroxy group, a nitro group, a cyano group, an amino group, an azido group, an amidino group, a hydrazino group, a hydrazono group, a carbonyl group, a carbamyl group, a thiol group, an ester group, a carboxyl group or a salt thereof, a sulfonic acid group or a salt thereof, phosphoric acid group or a salt thereof, a C1 to C20 alkyl group, a C1 to C20 alkoxy group, a C2 to C20 alkenyl group, a C2 to C20 alkynyl group, a C6 to C30 aryl group, a C7 to C30 arylalkyl group, a C2 to C20 heteroaryl group, a C3 to C20 heteroarylalkyl group, a C3 to C30 cycloalkyl group, a C3 to C15 cycloalkenyl group, a C6 to C15 cycloalkynyl group, a C2 to C20 heterocycloalkyl group, =S, and a combination thereof.

As used herein, when specific definition is not otherwise provided, "hetero" may refer to one including 1 to 3 heteroatoms selected from N, O, S, P, and Si.

As used herein, "alkyl group" may refer to a straight or branched saturated monovalent hydrocarbon group, for example, a methyl group, an ethyl group, a propyl group, an isopropyl group, an n-butyl group, an isobutyl group, a t-butyl group, a pentyl group, a hexyl group, and the like.

As used herein, "cycloalkyl group" may refer to a monovalent cyclic hydrocarbon group in which all ring-forming atoms are carbon, for example, a cyclopropyl group, a cyclobutyl group, a cyclopentyl group, a cyclohexyl group, and the like.

As used herein, "aryl group" may refer to a group in which all elements of the cycle have p-orbitals which form conjugation, and may be a monocyclic, polycyclic or fused polycyclic (e.g., rings sharing adjacent pairs of carbon atoms) functional group.

As used herein, when a definition is not otherwise provided, "cyano-containing group" may refer to a monovalent group such as a C1 to C30 alkyl group, a C2 to C30 alkenyl group, or a C2 to C30 alkynyl group where at least one hydrogen is substituted with a cyano group. The cyano-containing group may also refer to a divalent group such as a dicyanoalkenyl group represented by $=CR^{x'}-(CR^xR^y)_p-CR^{y'}(CN)_2$ wherein $R^x$, $R^y$, $R^{x'}$, and $R^{y'}$ are independently hydrogen or a C1 to C10 alkyl group and p is an integer of 0 to 10 (or 1 to 10). Specific examples of the cyano-containing group may be a dicyanomethyl group, a dicyanovinyl group, a cyanoethynyl group, and the like. The term "cyano-containing group" does not cover the cyano group (—CN) itself.

As used herein, when a definition is not otherwise provided, "combination thereof" may refer to at least two substituents bound to each other by a single bond or a C1 to C10 alkylene group, or at least two fused substituents.

As used herein, "aliphatic hydrocarbon group" may be for example, a C1 to C15 alkyl group such as a methyl group, an ethyl group, or a propyl group, a C1 to C15 alkylene group, a C2 to C15 alkenyl group such as ethenyl group or propenyl group, a C2 to C15 alkenylene group, a C2 to C15 alkynyl group such as ethynyl group or propynyl group, and the like, but is not limited thereto.

As used herein, "5-membered aromatic ring group" may refer to a 5-membered ring group (e.g., C5 aryl group) having a conjugation structure or a 5-membered heterocyclic group (e.g., C2 to C4 heteroaryl group) having a conjugation structure. As used herein, "6-membered aromatic ring group" may refer to a 6-membered ring group (e.g., C6 aryl group) having a conjugation structure or a 6-membered heterocyclic group (e.g., C2 to C5 heteroaryl groups) having a conjugation structure, but is not limited thereto. The aromatic ring group may include the 5-membered aromatic ring group or the 6-membered aromatic ring group, but is not limited thereto.

Hereinafter, a compound according to an embodiment is described. The compound is represented by Chemical Formula 1.

[Chemical Formula 1]

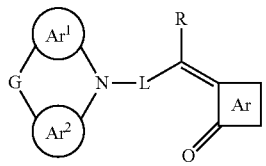

In Chemical Formula 1,

Ar may be one of a substituted or unsubstituted 5-membered aromatic ring group, a substituted or unsubstituted 6-membered aromatic ring group, and a condensed ring of two or more of the foregoing ring groups, R may be one of hydrogen, a substituted or unsubstituted C1 to C30 alkyl group, a substituted or unsubstituted C1 to C30 alkoxy group, a substituted or unsubstituted C6 to C30 aryl group, a substituted or unsubstituted C3 to C30 heteroaryl group, a halogen, a cyano group (—CN), a cyano-containing group, or a combination thereof, L may be one of a substituted or unsubstituted C6 to C16 aromatic ring group or a substituted or unsubstituted C3 to C13 N-containing heteroaromatic ring group, $Ar^1$ and $Ar^2$ may independently be one of a substituted or unsubstituted C6 to C30 aryl group or a substituted or unsubstituted C3 to C30 heteroaryl group, and G may be one of —Se—, —N=, —NR$^a$—, —SiR$^b$R$^c$—, —SiR$^{bb}$R$^{cc}$—, —GeR$^d$R$^e$—, or —GeR$^{dd}$R$^{ee}$— wherein R$^a$, R$^b$, R$^c$, R$^d$, and R$^e$ are independently one of hydrogen, a halogen, or a substituted or unsubstituted C1 to C10 alkyl group, wherein R$^{bb}$, R$^{cc}$, R$^{dd}$ and R$^{ee}$ may independently be one of a substituted or unsubstituted C1 to C10 alkyl group, or a substituted or unsubstituted C6 to C10 aryl group, R$^{bb}$ and R$^{cc}$ may be linked with each other to provide a ring structure, and R$^{dd}$ and R$^{ee}$ may be linked with each other to provide a ring structure.

The compound represented by Chemical Formula 1 includes an electron donor moiety of an N-containing hetero aromatic ring group, a linker of L and a methine group, and an electron acceptor moiety represented by Ar.

$Ar^1$ and $Ar^2$ of the N-containing hetero aromatic ring group are linked by G and thereby provides one conjugation structure overall to improve thermal stability of the compound. Such a conjugation structure may be formed by fusing three to four 5-membered or 6-membered aromatic ring groups, but is not limited thereto.

$Ar^1$ and $Ar^2$ may be a substituted or unsubstituted C6 to C30 aryl group or a substituted or unsubstituted C3 to C30 heteroaryl group that is formed by fusing aromatic rings, for example a substituted or unsubstituted C6 to C20 aryl group or a substituted or unsubstituted C3 to C20 heteroaryl group.

In an embodiment, the aryl group may be a phenyl group, a naphthyl group, or an anthracenyl group and the heteroaryl group may be one of a pyrrolyl group, a prazolyl group, an imidazolyl group, an oxazolyl group, an isoxazolyl group, a thiazolyl group, an isothiazolyl group, a pyridinyl group, a pyridazinyl group, a pyrimidinyl group, a pyrazinyl group, an indolyl group, a quinolinyl group, an isoquinolinyl group, an naphthyridinyl group, a cinnolinyl group, a quinazolinyl group, a phthalazinyl group, a benzotriazinyl group, a pyridopyrazinyl group, a pyridopyrimidinyl group, a pyridopyridazinyl group, a thienyl group, a benzothienyl group, a selenophenyl group, and a benzoselenophenyl group.

In Chemical Formula 1, L may be one of linkers represented by Chemical Formula 2-1.

[Chemical Formula 2-1]

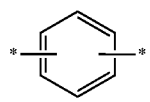 (1)

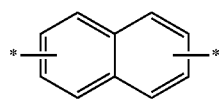 (2)

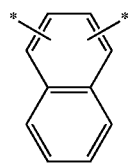 (3)

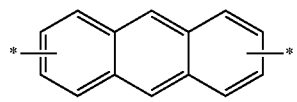 (4)

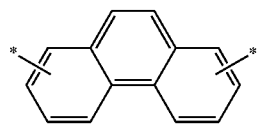 (5)

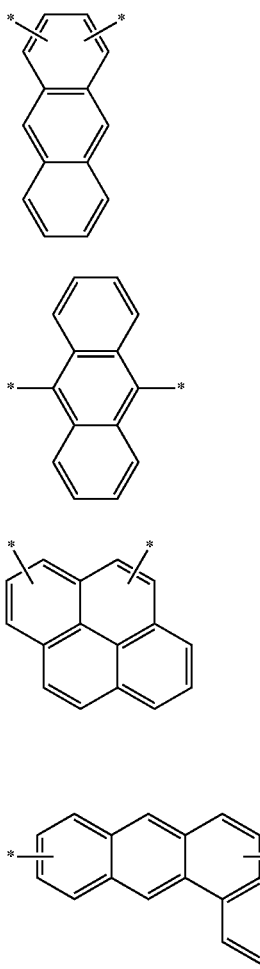

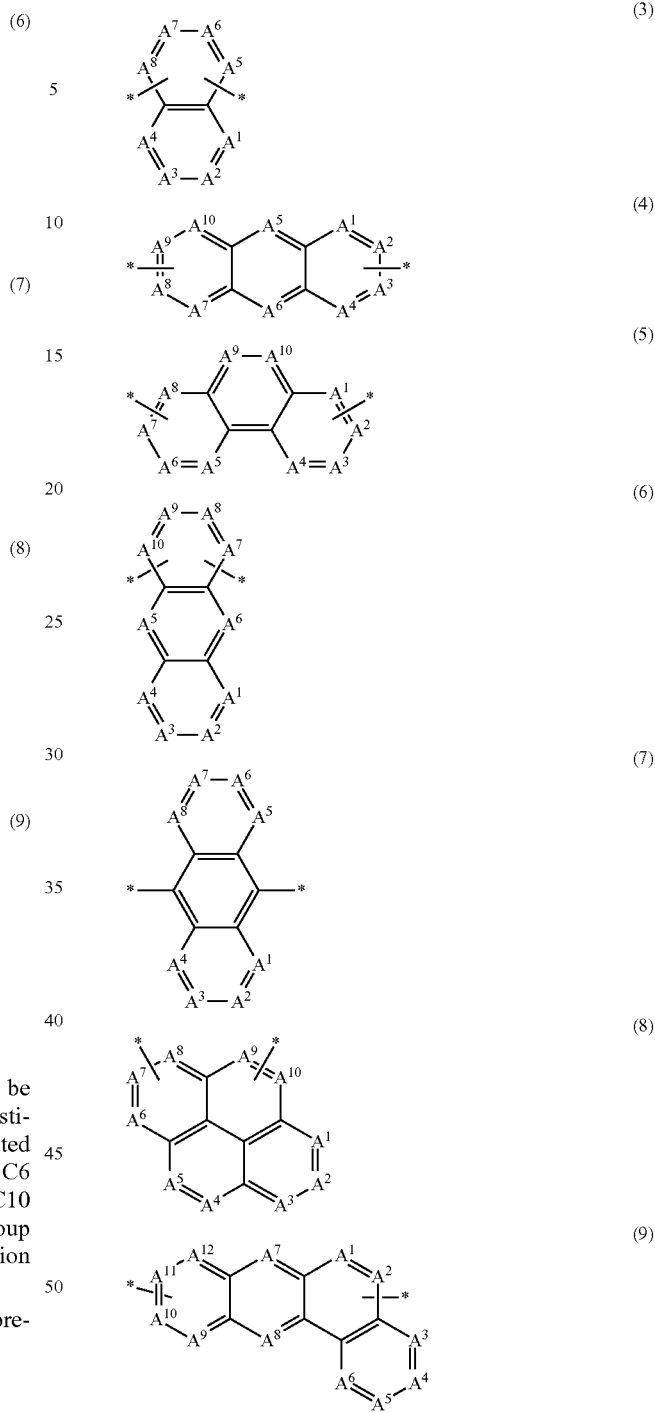

In Chemical Formula 2-1, hydrogen of —CH— in each aromatic ring may be optionally replaced by a group of a substituted or unsubstituted C1 to C20 alkyl group, a substituted or unsubstituted C1 to C20 alkoxy group, a substituted or unsubstituted C6 to C10 aryl group, a substituted or unsubstituted C4 to C10 heteroaryl group, a halogen (F, Cl, Br, or I), a cyano group (—CN), a cyano-containing group, or a combination thereof.

In Chemical Formula 1, L may be one of linkers represented by Chemical Formula 2-2.

[Chemical Formula 2-2]

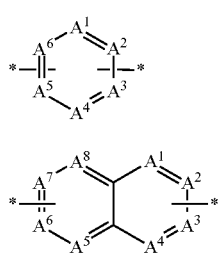

In Chemical Formula 2-2, $A^1$ to $A^{12}$ may independently be N or $CR^a$ (wherein, $R^a$ may be one of hydrogen, a substituted or unsubstituted C1 to C20 alkyl group, a substituted or unsubstituted C1 to C20 alkoxy group, a substituted or unsubstituted C6 to C10 aryl group, a substituted or unsubstituted C4 to C10 heteroaryl group, a halogen (F, Cl, Br, or I), a cyano group (—CN), a cyano-containing group, or a combination thereof), one to three of $A^1$ to $A^6$ in Chemical Formula (1) may be N, one to three of $A^1$ to $A^8$ in Chemical Formulae (2) and (3) may be N, one to three of $A^1$ to $A^{10}$ in Chemical Formulae (4) and (6) may be N, one to three of $A^1$ to $A^8$ in Chemical Formula (7) may be N, one to three of $A^1$ to $A^9$ in Chemical Formula (8) may be N, and one to three of $A^1$ to $A^{12}$ in Chemical Formula (9) may be N.

In Chemical Formula 1, L may be one of linkers represented by Chemical Formula 3.

[Chemical Formula 3]

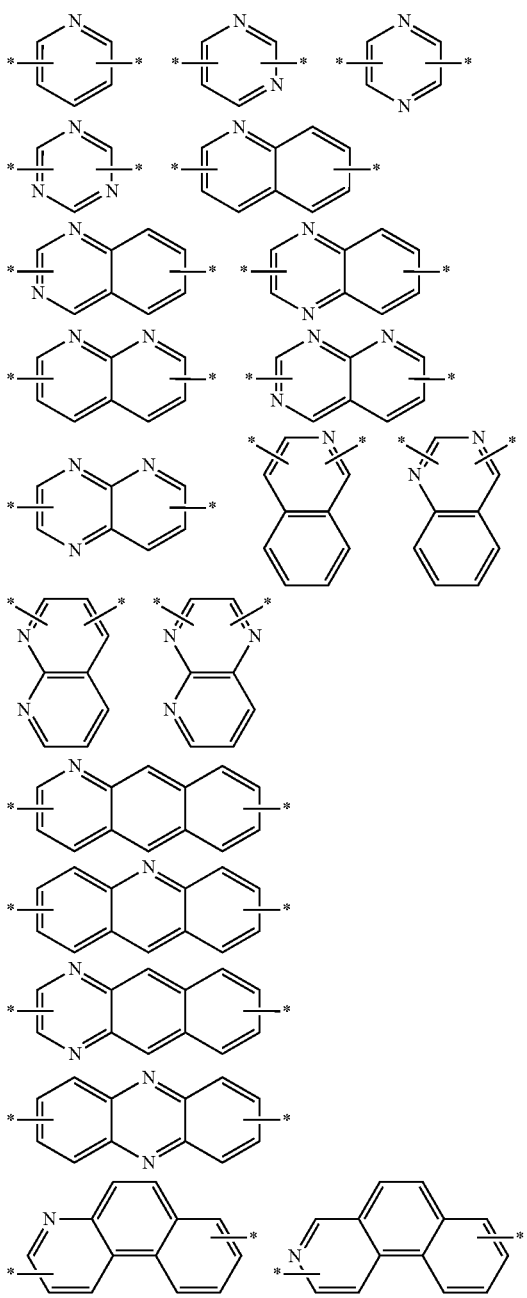

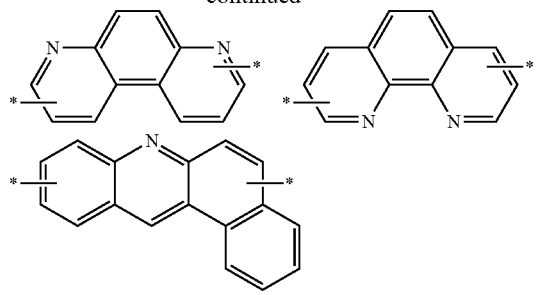

In Chemical Formula 3, hydrogen of —CH— in each aromatic ring may be optionally replaced by a group of a substituted or unsubstituted C1 to C20 alkyl group, a substituted or unsubstituted C1 to C20 alkoxy group, a substituted or unsubstituted C6 to C10 aryl group, a substituted or unsubstituted C4 to C10 heteroaryl group, a halogen (F, Cl, Br, or I), a cyano group (—CN), a cyano-containing group, or a combination thereof.

In some example embodiments, in Chemical Formula 1, at least one of $Ar^1$ and $Ar^2$ may include a heteroatom at the No. 1 position and the heteroatom may be one of nitrogen (N), sulfur (S), and selenium (Se).

In some example embodiments, in Chemical Formula 1, the ring group including $Ar^1$ and $Ar^2$ may be one of groups of Chemical Formula 4.

[Chemical Formula 4]

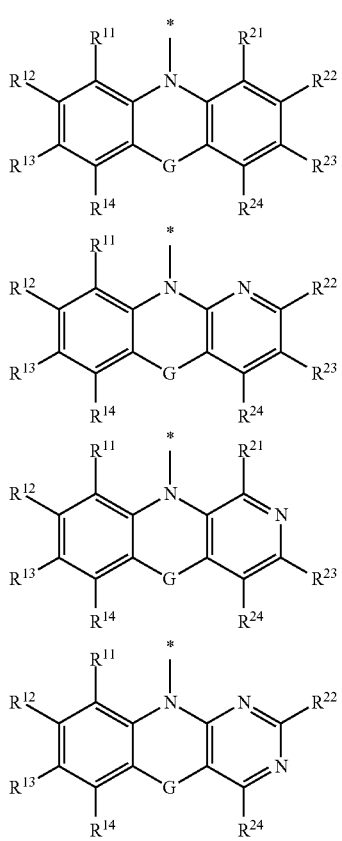

-continued

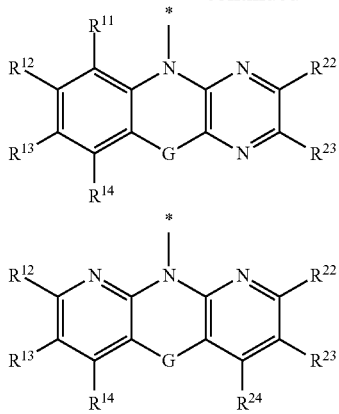

In Chemical Formula 4,

G may be one of —Se—, —N=, —NR$^a$—, —SiR$^b$R$^c$—, —SiR$^{bb}$R$^{cc}$—, —GeR$^d$R$^e$—, or —GeR$^{dd}$R$^{ee}$— wherein R$^a$, R$^b$, R$^c$, R$^d$, and R$^e$ are independently one of hydrogen, a halogen, or a substituted or unsubstituted C1 to C10 alkyl group, wherein R$^{bb}$, R$^{cc}$, R$^{dd}$ and R$^{ee}$ may independently be one of a substituted or unsubstituted C1 to C10 alkyl group, or a substituted or unsubstituted C6 to C10 aryl group, R$^{bb}$ and R$^{cc}$ may be linked with each other to provide a ring structure, and R$^{dd}$ and R$^{ee}$ may be linked with each other to provide a ring structure, and R$^{11}$ to R$^{14}$ and R$^{21}$ to R$^{24}$ may independently be one of hydrogen, a substituted or unsubstituted C1 to C30 alkyl group, a substituted or unsubstituted C6 to C30 aryl group, a substituted or unsubstituted C3 to C30 heteroaryl group, a halogen, a cyano group (—CN), a cyano-containing group, or a combination thereof, two adjacent groups of R$^{11}$ to R$^{14}$ may be linked with each other to provide a 5-membered aromatic ring group or a 6-membered aromatic ring group, or two adjacent groups of R$^{11}$ to R$^{14}$ may not be linked with each other to provide a 5-membered aromatic ring or a 6-membered aromatic ring, and two adjacent groups of R$^{21}$ to R$^{24}$ may be linked with each other to provide a 5-membered aromatic ring group or a 6-membered aromatic ring group or two adjacent groups of R$^{21}$ to R$^{24}$ may not be linked with each other to provide a 5-membered aromatic ring or a 6-membered aromatic ring.

The 5-membered aromatic ring or the 6-membered aromatic ring formed by the two adjacent groups of R$^{11}$ to R$^{14}$ and/or the two adjacent groups of R$^{21}$ to R$^{24}$ may include at least one heteroatom of N, O, S, P, and Si therein.

The ring structure formed by linking at least one pair of R$^{bb}$ and R$^{cc}$ or R$^{dd}$ and R$^{ee}$ may be a spiro structure or a fused ring structure, for example a 5-membered or 6-membered ring structure. The ring structures may include at least one heteroatom of N, O, S, P, and Si therein.

In Chemical Formula 1, an Ar-containing ring group includes at least one carbonyl group as an electron acceptor moiety.

For example, in Chemical Formula 1, the Ar-containing ring group that is bonded with the methine group may include one carbonyl group or two or more carbonyl groups.

For example, in Chemical Formula 1, the Ar-containing ring group that is bonded with the methine group may include at least one carbonyl group and at least one cyano-containing moiety.

In Chemical Formula 1, the Ar-containing ring group may be represented by Chemical Formula 5.

[Chemical Formula 5]

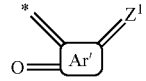

In Chemical Formula 5,

Ar' may be one of a substituted or unsubstituted 5-membered aromatic ring group, a substituted or unsubstituted 6-membered aromatic ring group, and a condensed ring of two or more of the foregoing ring groups, and Z$^1$ may be O or CR$^a$R$^b$, wherein R$^a$ and R$^b$ may independently be one of hydrogen, a substituted or unsubstituted C1 to C10 alkyl group, a cyano group, or a cyano-containing group, provided that at least one of R$^a$ and R$^b$ is a cyano group or a cyano-containing group.

For example, in Chemical Formula 1, the Ar-containing ring group that is bonded with the methine group may be a condensed ring of a substituted or unsubstituted 5-membered aromatic ring group and a substituted or unsubstituted 6-membered aromatic ring group.

In Chemical Formula 1, the Ar-containing ring group may be represented by one of Chemical Formulae 5-1 to 5-6.

[Chemical Formula 5-1]

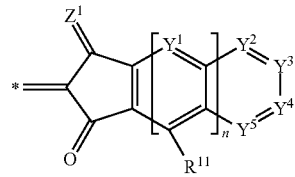

In Chemical Formula 5-1,

Z$^1$ may be O or CR$^a$R$^b$, wherein R$^a$ and R$^b$ may independently be one of hydrogen, a substituted or unsubstituted C1 to C10 alkyl group, a cyano group, or a cyano-containing group, provided that at least one of R$^b$ and R$^c$ is a cyano group or a cyano-containing group), Y$^1$ to Y$^5$ may be the same or different and are N or CR$^c$, wherein R$^c$ may be one of hydrogen, a substituted or unsubstituted C1 to C30 alkyl group, a substituted or unsubstituted C1 to C30 alkoxy group, a substituted or unsubstituted C6 to C30 aryl group, a substituted or unsubstituted C4 to C30 heteroaryl group, a halogen, a cyano group, a cyano-containing group, or a combination thereof, R$^{11}$ may be one of hydrogen, a substituted or unsubstituted C1 to C30 alkyl group, a substituted or unsubstituted C6 to C30 aryl group, a substituted or unsubstituted C4 to C30 heteroaryl group, a halogen, a cyano group (—CN), a cyano-containing group, and a combination thereof, n is 0 or 1, and

* indicates a linking position.

[Chemical Formula 5-2]

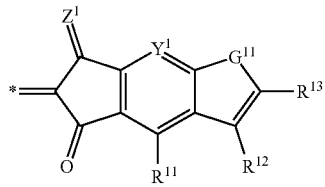

In Chemical Formula 5-2, $Y^1$ may be N or $CR^c$, wherein $R^c$ may be one of hydrogen, a substituted or unsubstituted C1 to C30 alkyl group, a substituted or unsubstituted C1 to C30 alkoxy group, a substituted or unsubstituted C6 to C30 aryl group, a substituted or unsubstituted C4 to C30 heteroaryl group, a halogen, a cyano group, a cyano-containing group, or a combination thereof, $R^{11}$ to $R^{13}$ may be the same or different and may be one of hydrogen, a substituted or unsubstituted C1 to C30 alkyl group, a substituted or unsubstituted C6 to C30 aryl group, a substituted or unsubstituted C4 to C30 heteroaryl group, a halogen, a cyano group (—CN), a cyano-containing group, or a combination thereof, and $G^{11}$ may be one of S, Se, $GeR^xR^y$, and Te, wherein $R^x$ and $R^y$ may be the same or different and may independently be one of hydrogen, a halogen, a substituted or unsubstituted C1 to C10 alkyl group, or a substituted or unsubstituted C6 to C10 aryl group.

[Chemical Formula 5-3]

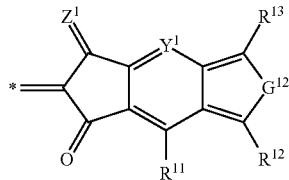

In Chemical Formula 5-3, $Y^1$ may be N or $CR^c$, wherein $R^c$ may be one of hydrogen, a substituted or unsubstituted C1 to C30 alkyl group, a substituted or unsubstituted C1 to C30 alkoxy group, a substituted or unsubstituted C6 to C30 aryl group, a substituted or unsubstituted C4 to C30 heteroaryl group, a halogen, a cyano group, a cyano-containing group, or a combination thereof, $R^{11}$ to $R^{13}$ may be the same or different and may be one of hydrogen, a substituted or unsubstituted C1 to C30 alkyl group, a substituted or unsubstituted C6 to C30 aryl group, a substituted or unsubstituted C4 to C30 heteroaryl group, a halogen, a cyano group (—CN), a cyano-containing group, or a combination thereof, and $G^{12}$ may be one of S, Se, $GeR^xR^y$, or Te, wherein $R^x$ and $R^y$ are the same or different and may independently be one of hydrogen, a halogen, a substituted or unsubstituted C1 to C10 alkyl group, or a substituted or unsubstituted C6 to C10 aryl group.

[Chemical Formula 5-4]

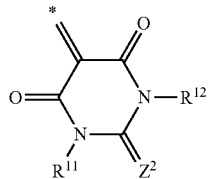

In Chemical Formula 5-4, $Z^2$ may be one of O, S, Se, Te, or $C(R^d)(CN)$, wherein $R^d$ may be one of hydrogen, a cyano group (—CN), or a C1 to C10 alkyl group, $R^{11}$ and $R^{12}$ may independently be one of hydrogen, a substituted or unsubstituted C1 to C30 alkyl group, a substituted or unsubstituted C1 to C30 alkoxy group, a substituted or unsubstituted C6 to C30 aryl group, a substituted or unsubstituted C4 to C30 heteroaryl group, a halogen, a cyano group (—CN), or a combination thereof, and

* indicates a linking position.

[Chemical Formula 5-5]

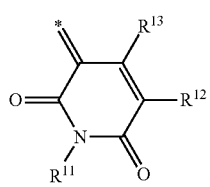

In Chemical Formula 5-5, $R^{11}$ to $R^{13}$ may independently be one of hydrogen, a substituted or unsubstituted C1 to C30 alkyl group, a substituted or unsubstituted C1 to C30 alkoxy group, a substituted or unsubstituted C6 to C30 aryl group, a substituted or unsubstituted C4 to C30 heteroaryl group, a halogen, a cyano group (—CN), a cyano-containing group, or a combination thereof, and

* indicates a linking position.

[Chemical Formula 5-6]

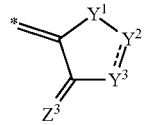

In Chemical Formula 5-6, $Z^3$ may be one of O, S, Se, Te, or $C(R^d)(CN)$, wherein $R^d$ may be one of hydrogen, a cyano group (—CN), or a C1 to C10 alkyl group, $Y^1$ may be one of O, S, Se, Te, or $GeR^eR^f$, wherein $R^e$ and $R^f$ may be the same or different and may independently be one of hydrogen, a halogen, a substituted or unsubstituted C1 to C10 alkyl group, or a substituted or unsubstituted C6 to C10 aryl group, $Y^2$ may be one of $CR^h$, C=O, C=S, or $C=(CR^i)(CN)$, $Y^3$ may be N or $NR^g$, if $Z^3$ is not oxygen (O), $Y^2$ may be C=O, $R^g$, $R^h$, and $R^i$ may independently be one of hydrogen, a substituted or unsubstituted C1 to C30 alkyl group, a substituted or unsubstituted C1 to C30 alkoxy group, a substituted or unsubstituted C6 to C30 aryl group, a substituted or unsubstituted C4 to C30 heteroaryl group, a halogen, a cyano group (—CN), a cyano-containing group, or a combination thereof, if $Y^2$ is $CR^h$ or $C=(CR^i)(CN)$ and $Y^3$ is $NR^g$, $Y^2$ and $Y^3$ may be linked with each other to provide a $Y^2$-$Y^3$-containing fused ring with the structure (a pentagonal ring) represented by Chemical Formula 5-6 or may not be a part of a $Y^2$-$Y^3$-containing fused ring with the structure represented by Chemical Formula 5-6, and

* indicates a linking position.

The ring group represented by Chemical Formula 5-1 may be for example represented by Chemical Formula 5-1-1, 5-1-2, or 5-1-3.

[Chemical Formula 5-1-1]

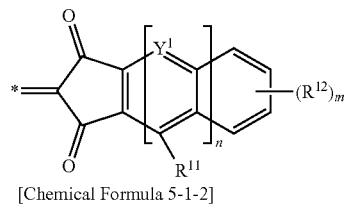

[Chemical Formula 5-1-2]

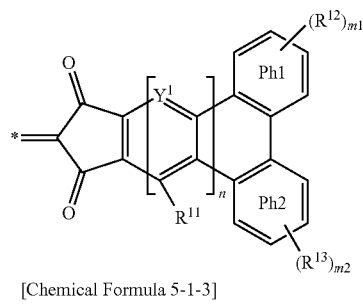

[Chemical Formula 5-1-3]

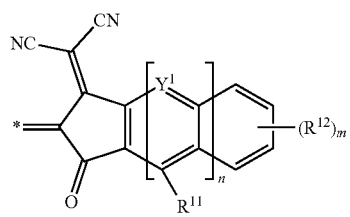

In Chemical Formulae 5-1-1, 5-1-2, and 5-1-3, $Y^1$, $R^{11}$, and n are the same as in Chemical Formula 5-1, $R^{12}$ and $R^{13}$ may independently be one of hydrogen, a substituted or unsubstituted C1 to C30 alkyl group, a substituted or unsubstituted C6 to C30 aryl group, a substituted or unsubstituted C4 to C30 heteroaryl group, a halogen, a cyano group (—CN), a cyano-containing group, or a combination thereof, m, m1, and m2 are independently an integer ranging from 0 to 4, and Ph1 and Ph2 denote a fused phenylene ring, provided that one of Ph1 and Ph2 may be optionally omitted.

The ring group represented by Chemical Formula 5-4 may be for example represented by Chemical Formula 5-4-1 or 5-4-2.

[Chemical Formula 5-4-1]

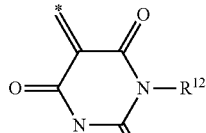

[Chemical Formula 5-4-2]

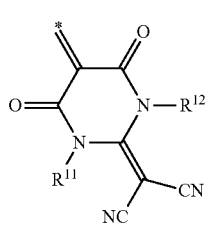

In Chemical Formulae 5-4-1 and 5-4-2, $R^1$ and $R^{12}$ are the same as in Chemical Formula 5-4.

The ring group represented by Chemical Formula 5-5 may be for example a ring group represented by Chemical Formula 5-5-1 or 5-5-2.

[Chemical Formula 5-5-1]

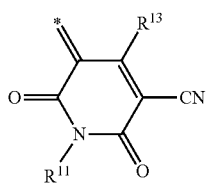

[Chemical Formula 5-5-2]

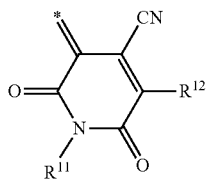

In Chemical Formulae 5-5-1 and 5-5-2, $R^{11}$ to $R^{13}$ are the same as in Chemical Formula 5-5.

The ring group represented by Chemical Formula 5-6 may be for example a ring group represented by Chemical Formula 5-6-1, 5-6-2, 5-6-3, 5-6-4, 5-6-5, or 5-6-6.

[Chemical Formula 5-6-1]

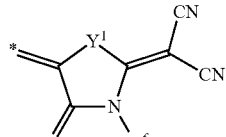

[Chemical Formula 5-6-2]

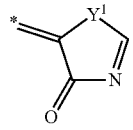

[Chemical Formula 5-6-3]

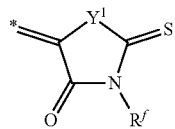

[Chemical Formula 5-6-4]

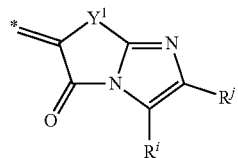

[Chemical Formula 5-6-5]

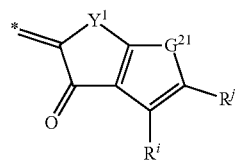

[Chemical Formula 5-6-6]

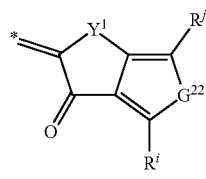

In Chemical Formulae 5-6-1, 5-6-2, 5-6-3, 5-6-4, 5-6-5, and 5-6-6, $Y^1$ and $R^f$ are the same as in Chemical Formula 5-6, in Chemical Formulae 5-6-5 to 5-6-6, $G^{21}$ and $G^{22}$ may independently be one of S, Se, $GeR^xR^y$, or Te, wherein $R^x$ and $R^y$ are the same or different and may independently be one of hydrogen, a halogen, a substituted or unsubstituted C1 to C10 alkyl group, or a substituted or unsubstituted C6 to C10 aryl group, and in Chemical Formulae 5-6-4 to 5-6-6, $R^i$ and $R^j$ may independently be one of hydrogen, a substituted or unsubstituted C1 to C30 alkyl group, a substituted or unsubstituted C1 to C30 alkoxy group, a substituted or unsubstituted C6 to C30 aryl group, a substituted or unsubstituted C4 to C30 heteroaryl group, a halogen, a cyano group (—CN), a cyano-containing group, or a combination thereof or are linked with each other to provide a fused ring. The fused ring may be a 5-membered or 6-membered aromatic ring group or a heteroaromatic ring group.

Examples of the compound of Chemical Formula 1 may be at least one of compounds represented by Chemical Formula 6-1, Chemical Formula 6-2, Chemical Formula 6-3, Chemical Formula 6-4, Chemical Formula 6-5, Chemical Formula 6-6, or Chemical Formula 6-7, but are not limited thereto.

[Chemical Formula 6-1]

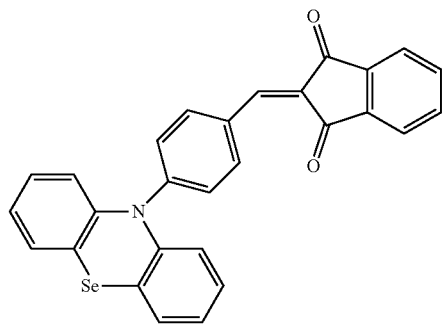

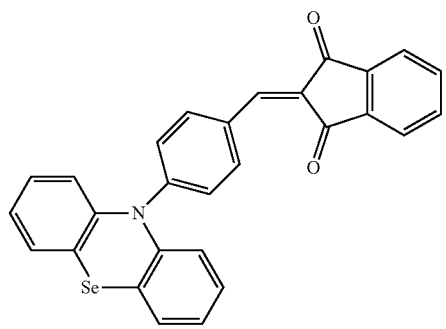

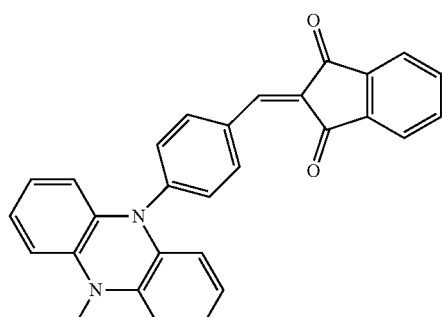

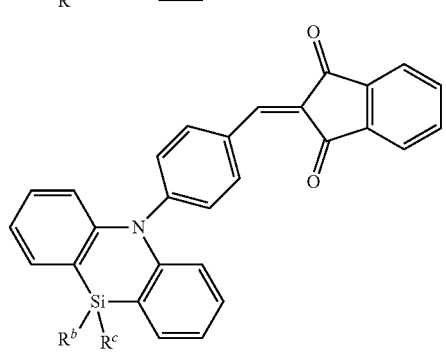

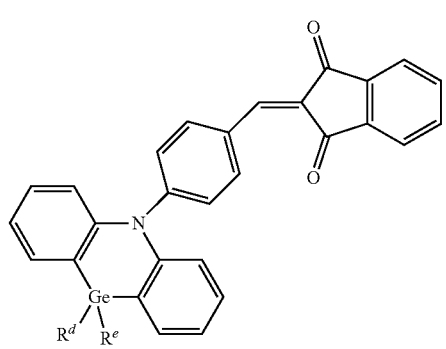

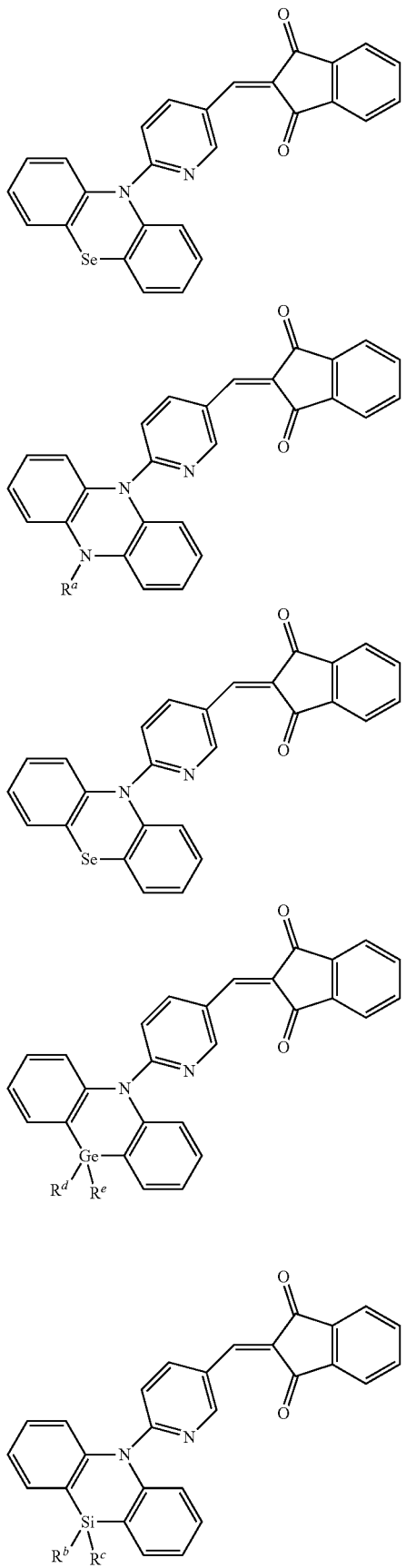
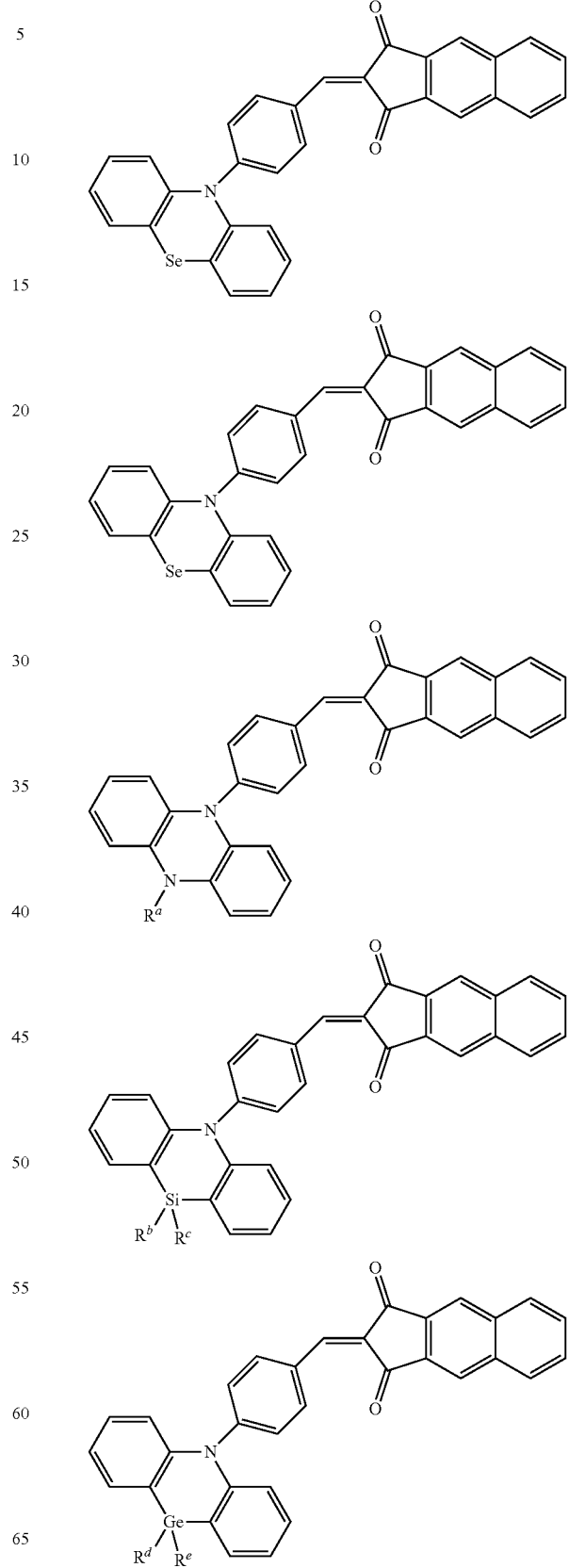
[Chemical Formula 6-2]

-continued
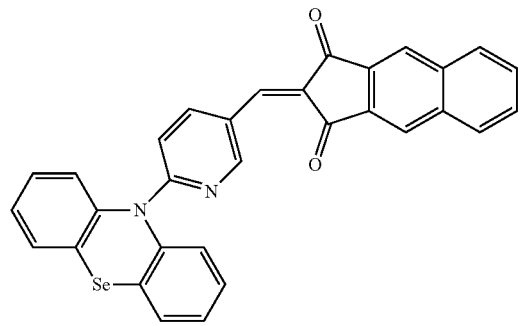
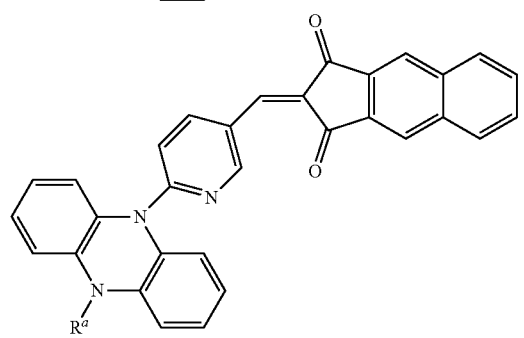
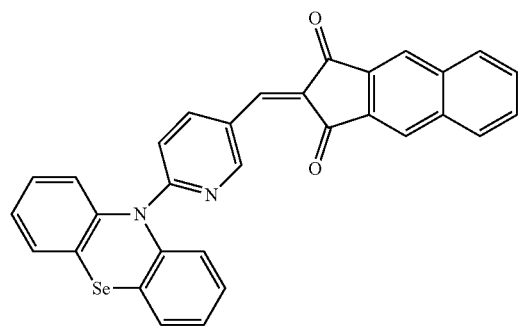
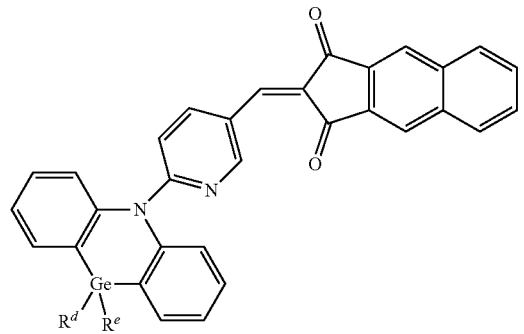
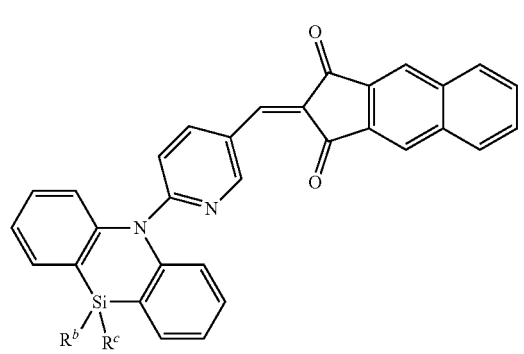
-continued
[Chemical Formula 6-3]
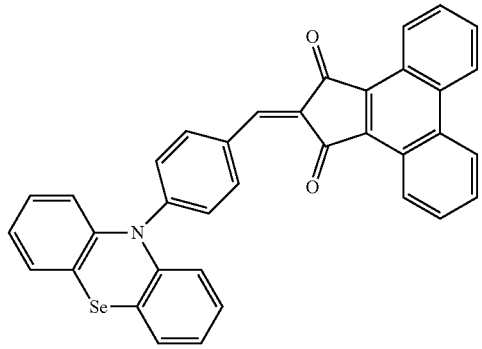
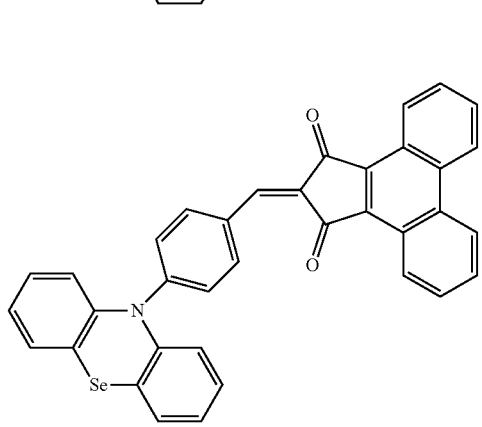
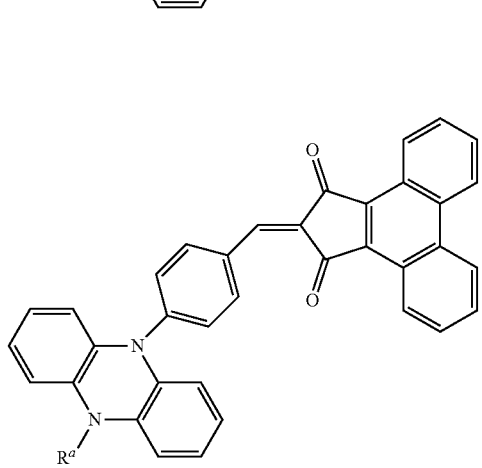
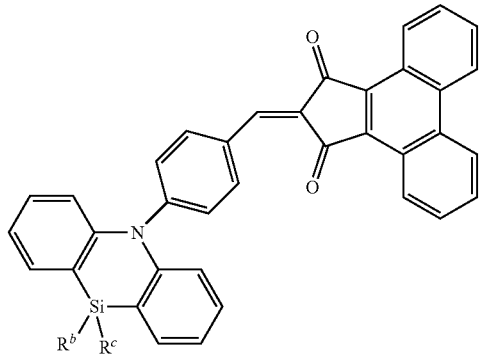

-continued
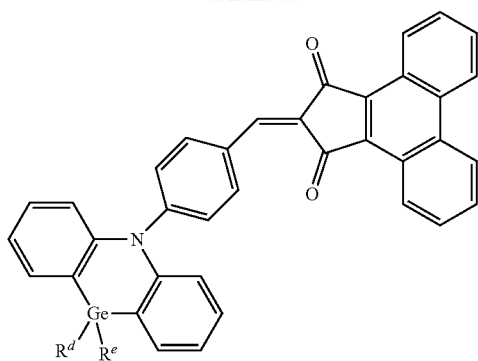
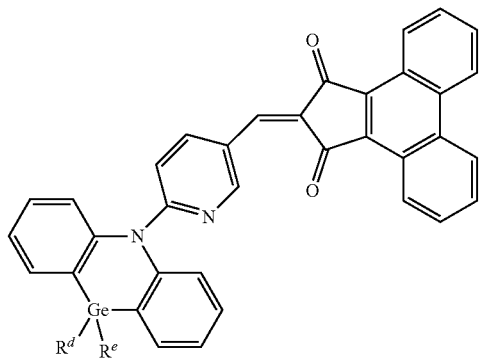
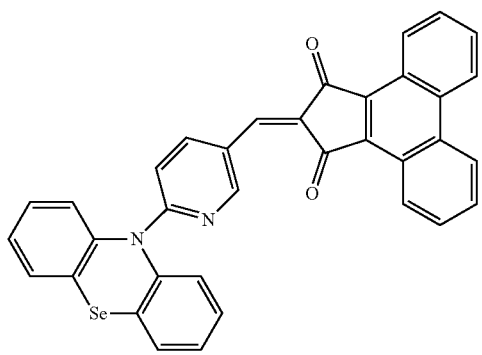
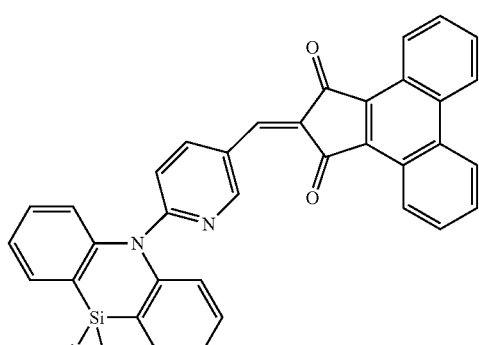
[Chemical Formula 6-4]
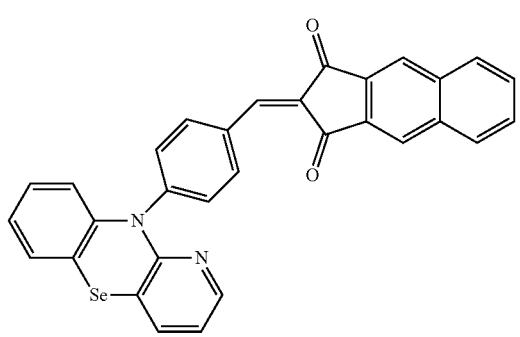
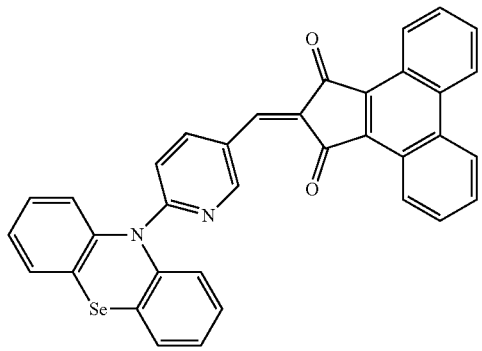
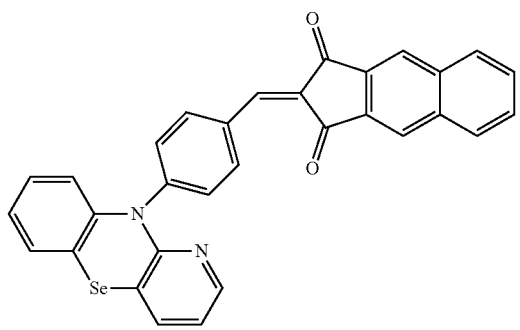

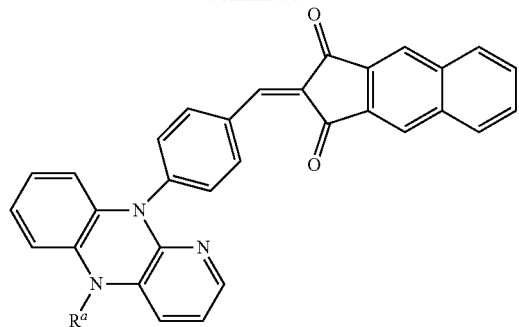
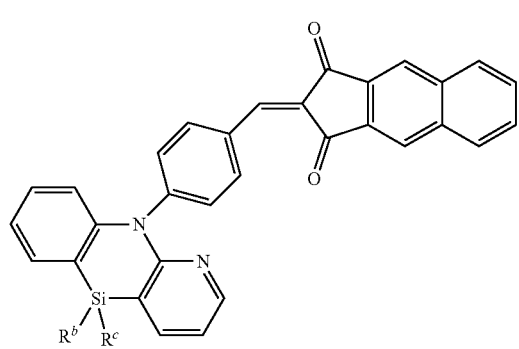
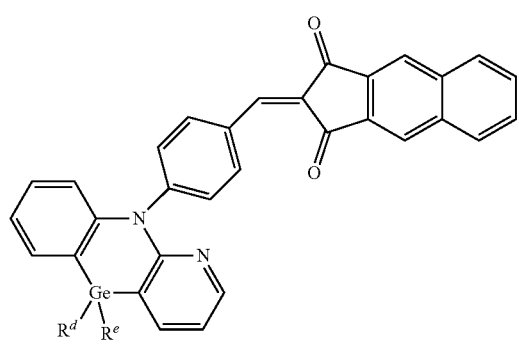
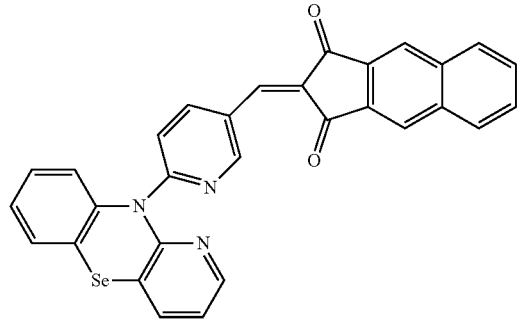
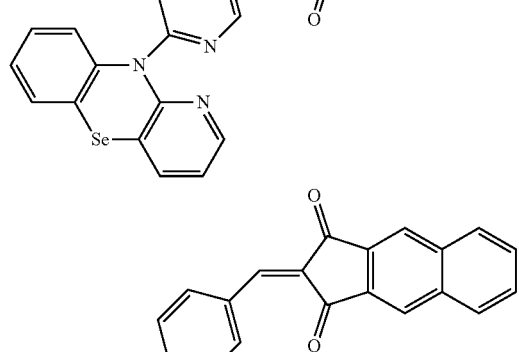
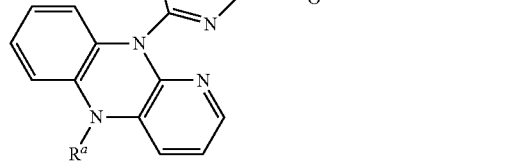
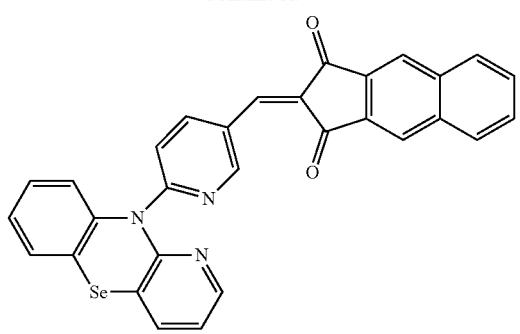
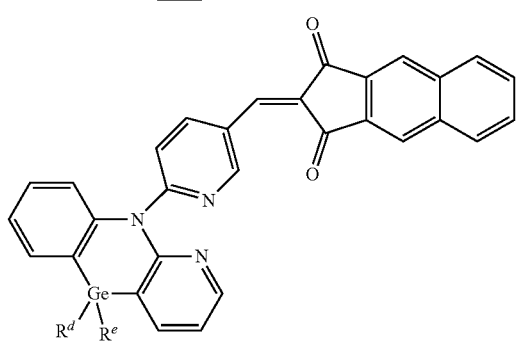
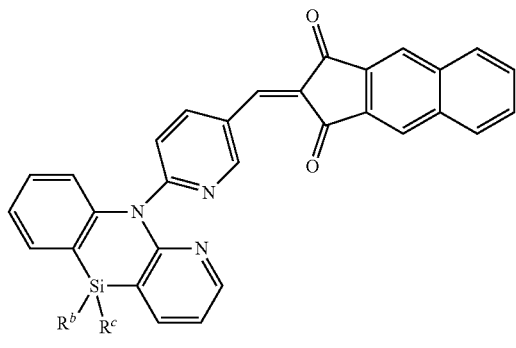
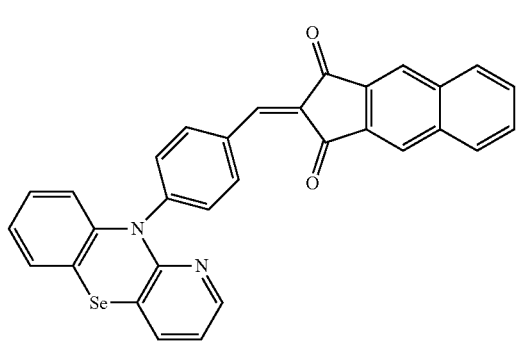
[Chemical Formula 6-5]
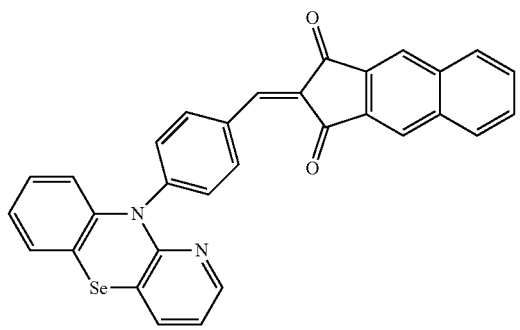

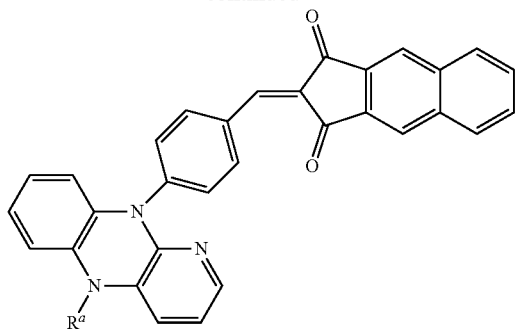
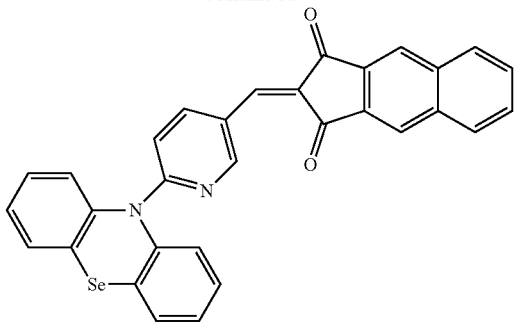
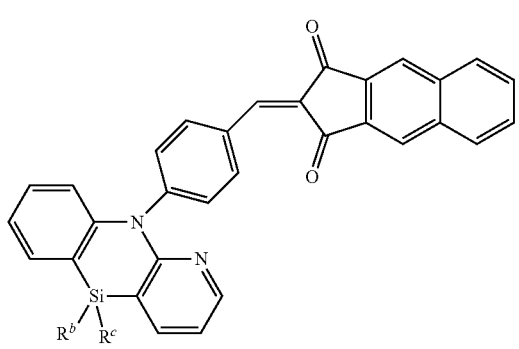
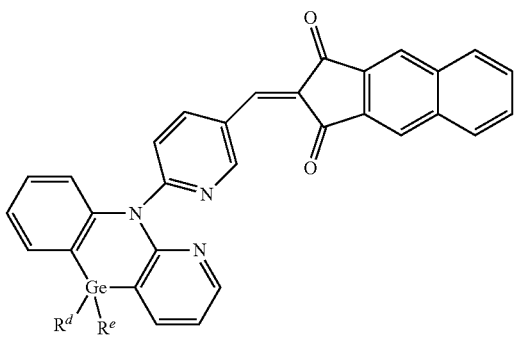
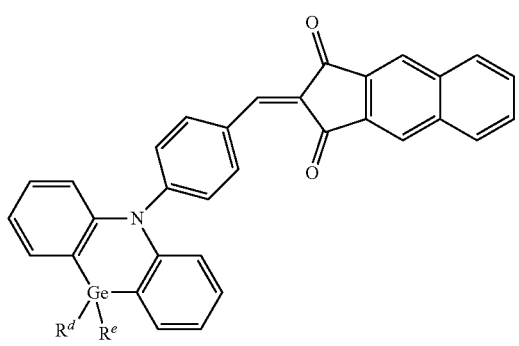
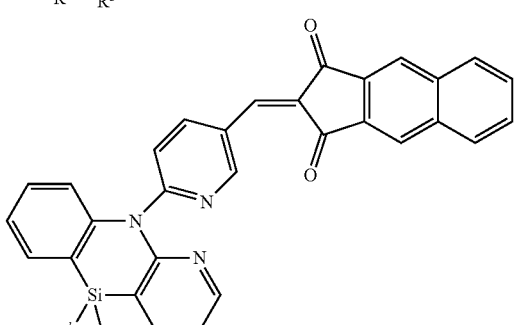
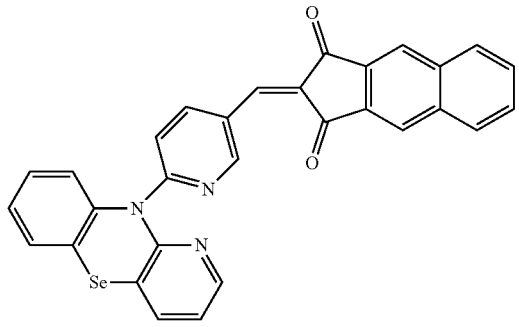
[Chemical Formula 6-6]
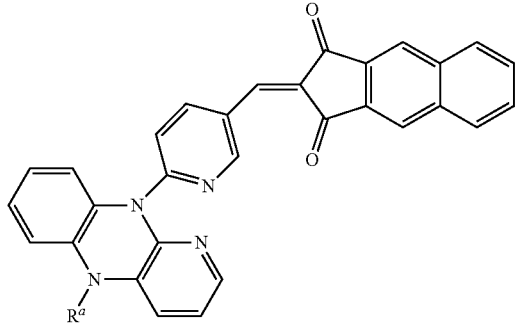
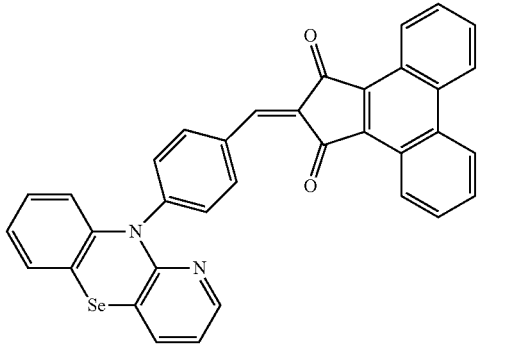

-continued
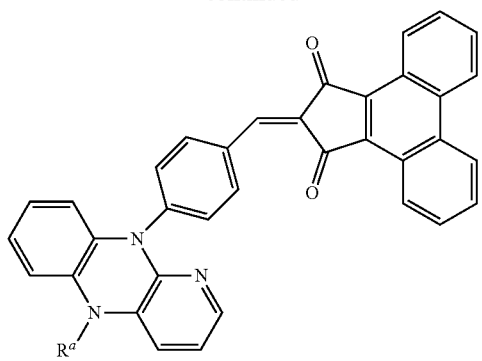
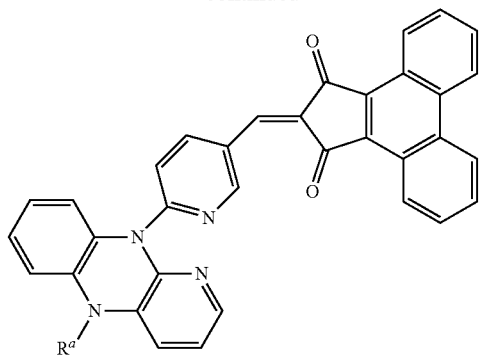
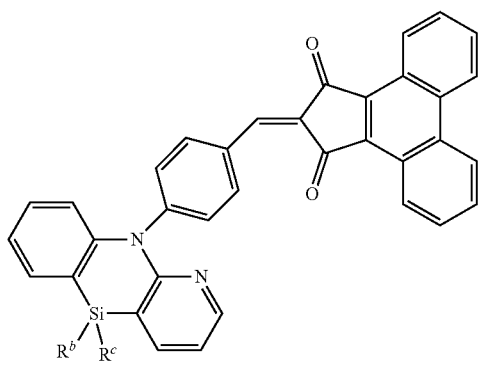
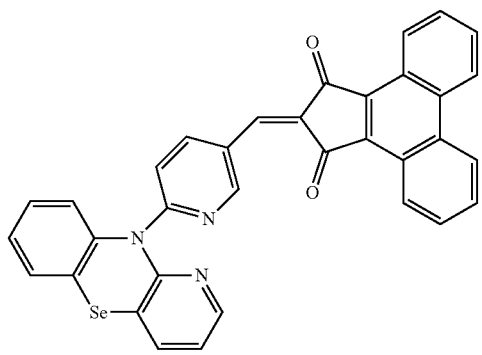
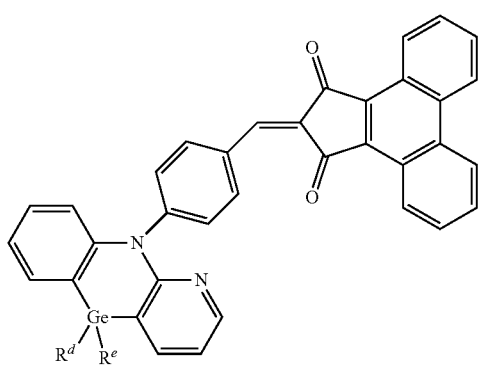
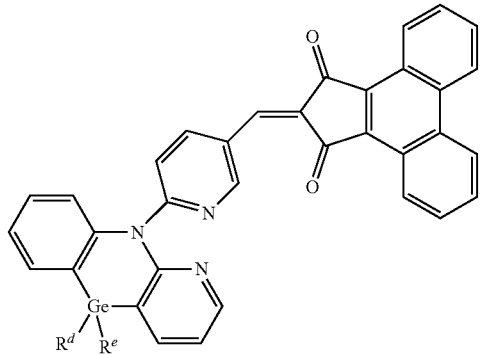
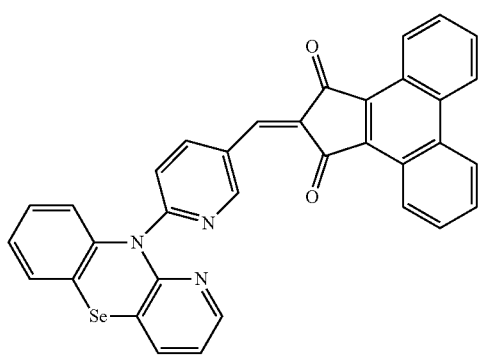
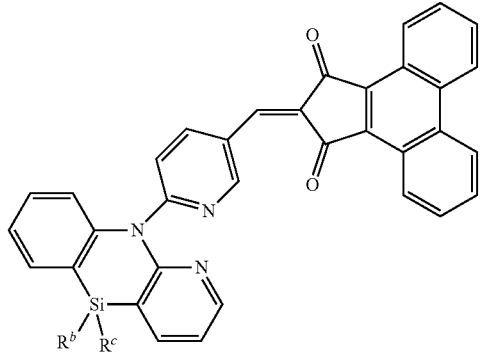

[Chemical Formula 6-7]
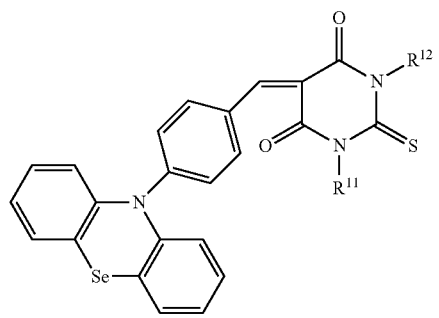
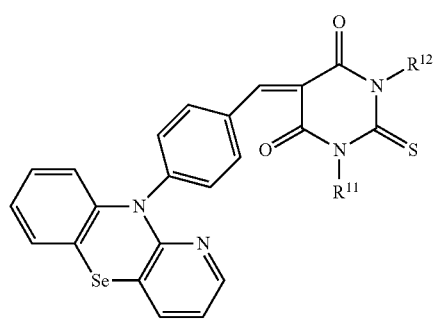
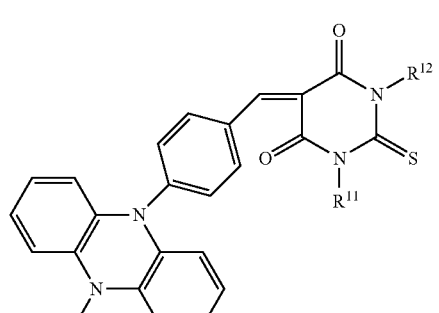
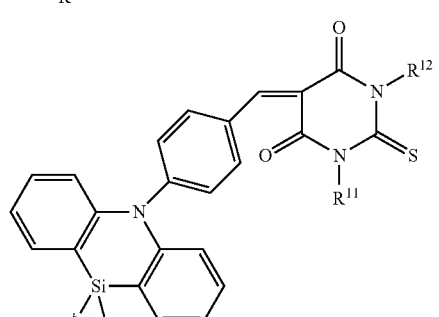
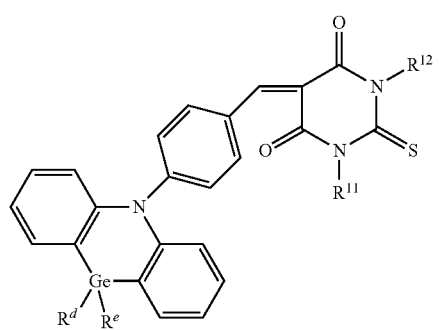
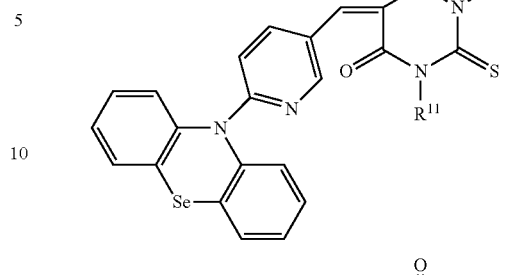
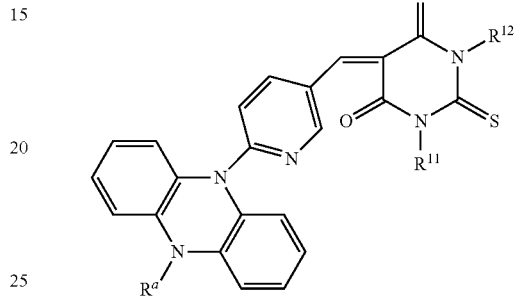
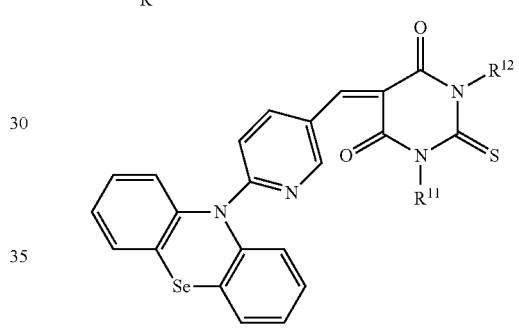
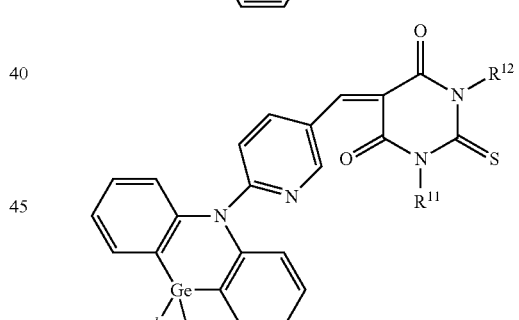
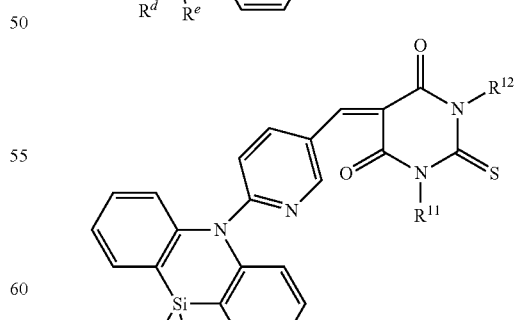
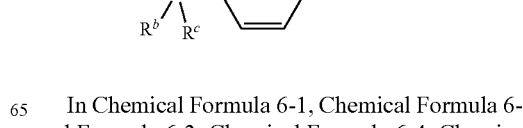
In Chemical Formula 6-1, Chemical Formula 6-2, Chemical Formula 6-3, Chemical Formula 6-4, Chemical Formula 6-5, Chemical Formula 6-6, and Chemical Formula 6-7, $R^a$, $R^b$, $R^c$, $R^d$, and $R^e$ may independently be one of hydrogen, a halogen, or a substituted or unsubstituted C1 to C10 alkyl group, $R^b$ and $R^c$ may be linked with each other to provide a ring structure, $R^d$ and $R^e$ may be linked with each other to provide a ring structure, $R^{11}$ and $R^{12}$ are the same as in Chemical Formula 5-4, and hydrogen in each aromatic ring may be replaced by a group of a substituted or unsubstituted C1 to C30 alkyl group, a substituted or unsubstituted C1 to C30 alkoxy group, a substituted or unsubstituted C6 to C30 aryl group, a substituted or unsubstituted C4 to C30 heteroaryl group, a halogen (F, Cl, Br, or I), a cyano group (—CN), a cyano-containing group, or a combination thereof.

In Chemical Formula 6-1, Chemical Formula 6-2, Chemical Formula 6-3, Chemical Formula 6-4, Chemical Formula 6-5, Chemical Formula 6-6, and Chemical Formula 6-7, the ring structure formed by linking $R^b$ and $R^c$ and the ring structure formed by linking $R^d$ and $R^e$ may be a spiro structure or a fused ring structure, for example a 5-membered or 6-membered ring structure. The ring structures may include at least one heteroatom of N, O, S, P, and Si therein.

The compound is a compound selectively absorbing light in a desired (and/or alternatively predetermined) wavelength region and may exhibit a light absorption curve having a full width at half maximum (FWHM) of about 50 nm to about 110 nm, in a thin film state. Herein, the FWHM is a width of a wavelength corresponding to half of a height of a maximum absorption point. When the full width at half maximum (FWHM) is small, wavelength selectivity is increased by selectively absorbing light in a narrow wavelength region. As used herein, when specific definition is not otherwise provided, it may be defined by absorbance measured by UV-Vis spectroscopy. When the full width at half maximum (FWHM) is within the range, selectivity in a green wavelength region may be increased. The thin film may be a thin film deposited under a vacuum condition.

The compound may be formed into a thin film by using a deposition method. The deposition method may provide a uniform thin film and have small inclusion possibility of impurities into the thin film, but when the compound has a lower melting point than a temperature for the deposition, a product decomposed from the compound may be deposited and thus performance of a device may be deteriorated. Accordingly, the compound desirably has a higher melting point than the deposition temperature. The compound has, for example, at least about 10° C., for example at least about 20° C., or at least about 30° C. higher melting point than the deposition temperature and thus may be desirably used for the deposition.

Specifically, a donor/acceptor-type material represented by Chemical Formula 1 may be thermally decomposed at its melting point (Tm) because the melting point (Tm) of the material is similar to a decomposition temperature (Td). Accordingly, when the material has a lower Tm than a sublimation temperature (deposition temperature, Ts) at which the material is vacuum-deposited to form a film, the material may be decomposed before sublimated (deposited) and not be used to manufacture a device. Since as for this material, Tm is higher than Ts, and desirably, ΔT(Tm−Ts) ≥10° C., this material is appropriate for manufacturing a stable image sensor.

In addition, during repetitive deposition, decomposition products may remain, which may have unfavorable effects on performance of a device. However, the compound may not produce decomposition products and thus may improve process stability.

In addition, a micro lens array (MLA) needs to be formed to concentrate light after manufacturing a photoelectric device during manufacture of an image sensor. This micro lens array requires a relatively high temperature (about 160° C. or greater), and this annealing process may deteriorate performance of the photoelectric device. The performance deterioration of the photoelectric device during the annealing process of MLA may be caused not by chemical decomposition of an organic material but its morphology change. The morphology change is in general caused, when a material starts a thermal vibration due to the annealing process, but a material having a firm molecular structure may not have the thermal vibration and be limited and/or prevented from the deterioration by the annealing process. The compound may be suppressed from the thermal vibration of molecules due to a conjugation structure (G-containing linking structure in Chemical Formula 1) in a donor region and stably maintained during the MLA annealing process and thus secure process stability.

The compound may be a p-type semiconductor compound. Since the compound works as a p-type semiconductor, the compound may be appropriately used, as long as it has a higher LUMO level than an n-type semiconductor. For example, when the compound is mixed with an n-type material such as fullerene, the compound desirably has a higher LUMO level than 4.2 eV than the fullerene having a LUMO level of 4.2 eV. As for the desirable HOMO-LUMO level of the compound, when the compound has a HOMO level ranging from about 5.0 eV to about 5.9 eV, and an energy bandgap ranging from about 1.9 eV to about 2.3 eV, the LUMO level of the compound is in a range of about 2.7 eV to about 3.9 eV. The compound having a HOMO level, an LUMO level, and an energy bandgap within the ranges may be used as a p-type semiconductor compound effectively absorbing light in a green wavelength region, and thus has high external quantum efficiency (EQE) and resultantly improves photoelectric conversion efficiency.

In some example embodiments, in view of a thin film formation, a stably depositable compound is desirable and thus the compound has a molecular weight of about 300 g/mol to about 1500 g/mol. However, even though the compound has a molecular weight out of the range, any sublimable (depositable) compound may be used without limitation. In addition, when the compound is formed to form a thin film using a coating process, any compound that is dissolved in a solvent and coated may be used without limitation.

Hereinafter, a photoelectric device including the compound according to an example embodiment is described with reference to drawings.

FIG. 1 is a cross-sectional view showing a photoelectric device according to an example embodiment.

Referring to FIG. 1, a photoelectric device 100 according to an example embodiment includes a first electrode 10 and a second electrode 20, and an active layer 30 between the first electrode 10 and the second electrode 20.

One of the first electrode 10 and the second electrode 20 is an anode and the other is a cathode. At least one of the first electrode 10 and the second electrode 20 may be a light-transmitting electrode, and the light-transmitting electrode may be made of, for example, a transparent conductor such as indium tin oxide (ITO) or indium zinc oxide (IZO), or a metal thin layer of a thin single layer or multilayer. When one of the first electrode 10 and the second electrode 20 is a non-light-transmitting electrode, it may be made of, for example, an opaque conductor such as aluminum (Al).

The active layer 30 includes a p-type semiconductor and an n-type semiconductor to form a pn junction, and absorbs external light to generate excitons and then separates the generated excitons into holes and electrons.

The active layer 30 includes the compound represented by Chemical Formula 1. The compound may act as a p-type semiconductor compound in the active layer 30.

The compound is a compound selectively absorbing light in a green wavelength region, and the active layer 30 including the compound may have a maximum absorption wavelength ($\lambda_{max}$) in a wavelength region of greater than or equal to about 500 nm and less than about 600 nm, for example about 520 nm to about 555 nm.

The active layer 30 may exhibit a light absorption curve having a relatively narrow full width at half maximum (FWHM) of about 50 nm to about 120 nm, for example about 50 nm to about 100 nm. Accordingly, the active layer 30 has high selectivity for light in a green wavelength region.

The active layer may have an absorption coefficient of greater than or equal to about $5.5 \times 10^4$ cm$^{-1}$, for example about $5.8 \times 10^4$ cm$^{-1}$ to about $10 \times 10^4$ cm$^{-1}$ or about $7.0 \times 10^4$ cm$^{-1}$ to about $10 \times 10^4$ cm$^{-1}$ when including the compound Chemical Formula 1 and C60 in a volume ratio of about 0.9:1 to about 1.1:1, for example about 1:1.

The active layer 30 may further include an n-type semiconductor compound for forming a pn junction.

The n-type semiconductor compound may include sub-phthalocyanine or a sub-phthalocyanine derivative, fullerene or a fullerene derivative, thiophene or a thiophene derivative, or a combination thereof.

The fullerene may include C60, C70, C76, C78, C80, C82, C84, C90, C96, C240, C540, a mixture thereof, a fullerene nanotube, and the like. The fullerene derivative may refer to compounds of these fullerenes having a substituent attached thereto. The fullerene derivative may include a substituent such as alkyl group, aryl group, or a heterocyclic group. Examples of the aryl groups and heterocyclic groups may be are a benzene ring, a naphthalene ring, an anthracene ring, a phenanthrene ring, a fluorene ring, a triphenylene ring, a naphthacene ring, a biphenyl ring, a pyrrole ring, a furan ring, a thiophene ring, an imidazole ring, an oxazole ring, a thiazole ring, a pyridine ring, a pyrazine ring, a pyrimidine ring, a pyridazine ring, an indolizine ring, an indole ring, a benzofuran ring, a benzothiophene ring, an isobenzofuran ring, a benzimidazole ring, an imidazopyridine ring, a quinolizidine ring, a quinoline ring, a phthalazine ring, a naphthyridine ring, a quinoxaline ring, a quinoxazoline ring, an isoquinoline ring, a carbazole ring, a phenanthridine ring, an acridine ring, a phenanthroline ring, a thianthrene ring, a chromene ring, an xanthene ring, a phenoxazine ring, a phenoxathiin ring, a phenothiazine ring, or a phenazine ring.

The sub-phthalocyanine or the sub-phthalocyanine derivative may be represented by Chemical Formula 7.

[Chemical Formula 7]

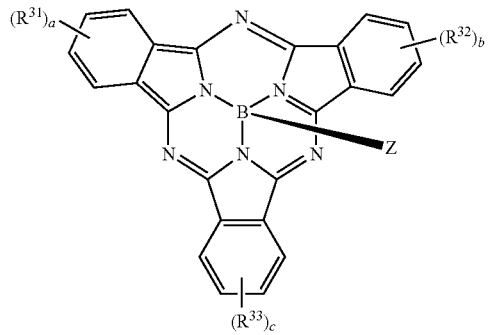

In Chemical Formula 7,
$R^{31}$ to $R^{33}$ may independently be one of hydrogen, a substituted or unsubstituted C1 to C30 alkyl group, a substituted or unsubstituted C1 to C30 alkoxy group, a substituted or unsubstituted C6 to C30 aryl group, a substituted or unsubstituted C3 to C30 heteroaryl group, a halogen, a halogen-containing group, or a combination thereof, a, b, and c may be integers ranging from 1 to 3, and Z may be a monovalent substituent.

For example, Z may be a halogen or a halogen-containing group, for example F, Cl, an F-containing group, or a Cl-containing group.

The halogen may refer to F, Cl, Br, or I and the halogen-containing group may refer to alkyl group where at least one of hydrogen is replaced by F, Cl, Br, or I.

The thiophene derivative may be for example represented by Chemical Formula 8 or 9, but is not limited thereto.

[Chemical Formula 8]

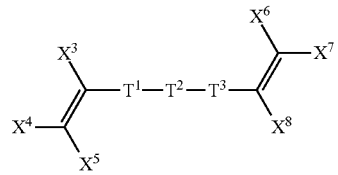

EWG$^1$-T$^1$-T$^2$-T$^3$-EWG$^2$      [Chemical Formula 9]

In Chemical Formulae 8 and 9, $T^1$, $T^2$, and $T^3$ may be aromatic rings including substituted or unsubstituted thiophene moieties, $T^1$, $T^2$, and $T^3$ may independently be present or may be fused to each other, $X^3$ to $X^8$ may independently be one of hydrogen, a substituted or unsubstituted C1 to C30 alkyl group, a substituted or unsubstituted C1 to C30 alkoxy group, a substituted or unsubstituted C6 to C30 aryl group, a substituted or unsubstituted C3 to C30 heterocyclic group, a cyano group, or a combination thereof, and EWG$^1$ and EWG$^2$ are independently electron withdrawing groups.

For example, in Chemical Formula 8, at least one of $X^3$ to $X^8$ may be an electron withdrawing group, for example a cyano-containing group.

The active layer 30 may further include a second p-type semiconductor compound selectively absorbing green light. The p-type semiconductor compound may be a compound represented by Chemical Formula 10.

[Chemical Formula 10]

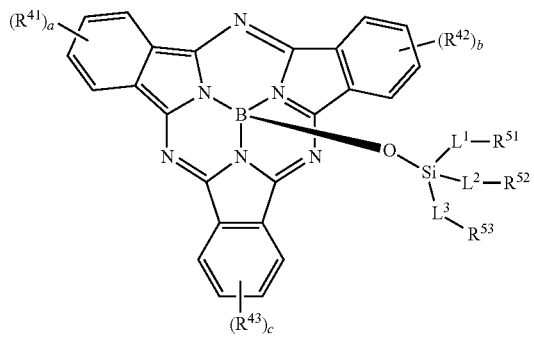

In Chemical Formula 10, $R^{41}$ to $R^{43}$ may independently be one of hydrogen, a substituted or unsubstituted C1 to C30 aliphatic hydrocarbon group, a substituted or unsubstituted C6 to C30 aromatic hydrocarbon group, a substituted or unsubstituted C1 to C30 aliphatic heterocyclic group, a substituted or unsubstituted C2 to C30 aromatic heterocyclic group, a substituted or unsubstituted C1 to C30 alkoxy group, a substituted or unsubstituted C6 to C30 aryloxy group, thiol group, a substituted or unsubstituted C1 to C30 alkylthio group, a substituted or unsubstituted C6 to C30 arylthio group, a cyano group, a cyano-containing group, a halogen, a halogen-containing group, a substituted or unsubstituted sulfonyl group (e.g., a substituted or unsubstituted C0 to C30 aminosulfonyl group, a substituted or unsubstituted C1 to C30 alkylsulfonyl group or a substituted or unsubstituted C6 to C30 arylsulfonyl group), or a combination thereof, or two adjacent groups of $R^{41}$ to $R^{43}$ are linked with each other to provide a fused ring, $L^1$ to $L^3$ may independently be one of a single bond, a substituted or unsubstituted C1 to C30 alkylene group, a substituted or unsubstituted C6 to C30 arylene group, a divalent substituted or unsubstituted C3 to C30 heterocyclic group, or a combination thereof, $R^{51}$ to $R^{53}$ may independently be one of a substituted or unsubstituted C1 to C30 alkyl group, a substituted or unsubstituted C1 to C30 alkoxy group, a substituted or unsubstituted C6 to C30 aryl group, a substituted or unsubstituted C3 to C30 heterocyclic group, a substituted or unsubstituted C1 to C30 alkoxy group, a substituted or unsubstituted amine group (e.g., a substituted or unsubstituted C1 to C30 alkylamine group or a substituted or unsubstituted C6 to C30 arylamine group), a substituted or unsubstituted silyl group, or a combination thereof, and a to c are independently an integer ranging from 0 to 4.

The second p-type semiconductor compound selectively absorbing green light may be included in an amount of about 500 to about 1500 parts by weight based on 100 parts by weight of the compound represented by Chemical Formula 1.

The active layer 30 may be a single layer or a multilayer. The active layer 30 may be, for example, an intrinsic layer (I layer), a p-type layer/I layer, an I layer/n-type layer, a p-type layer/I layer/n-type layer, a p-type layer/n-type layer, and the like.

The intrinsic layer (I layer) may include the compound of Chemical Formula 1 and the n-type semiconductor compound in a volume ratio of about 1:100 to about 100:1. The compound of Chemical Formula 1 and the n-type semiconductor compound may be included in a volume ratio ranging from about 1:50 to about 50:1 within the range, specifically, about 1:10 to about 10:1, and more specifically, about 1:1. When the compound of Chemical Formula 1 and the n-type semiconductor compound have a composition ratio within the range, an exciton may be effectively produced, and a pn junction may be effectively formed.

The p-type layer may include the semiconductor compound of Chemical Formula 1, and the n-type layer may include the n-type semiconductor compound.

The active layer 30 may have a thickness of about 1 nm to about 500 nm and specifically, about 5 nm to about 300 nm. When the active layer 30 has a thickness within the range, the active layer may effectively absorb light, effectively separate holes from electrons, and deliver them, thereby effectively improving photoelectric conversion efficiency. An optimal thickness of a thin film may be, for example, determined by an absorption coefficient of the active layer 30, and may be, for example, a thickness being capable of absorbing light of at least about 70% or more, for example about 80% or more, and for another example about 90%.

In the photoelectric device 100, when light enters from the first electrode 10 and/or second electrode 20, and when the active layer 30 absorbs light in a desired (and/or alternatively predetermined) wavelength region, excitons may be produced from the inside. The excitons are separated into holes and electrons in the active layer 30, and the separated holes are transported to an anode that is one of the first electrode 10 and the second electrode 20 and the separated electrons are transported to the cathode that is the other of and the first electrode 10 and the second electrode 20 so as to flow a current in the photoelectric device.

Hereinafter, a photoelectric device according to another example embodiment is described with reference to FIG. 2.

Figure 2:
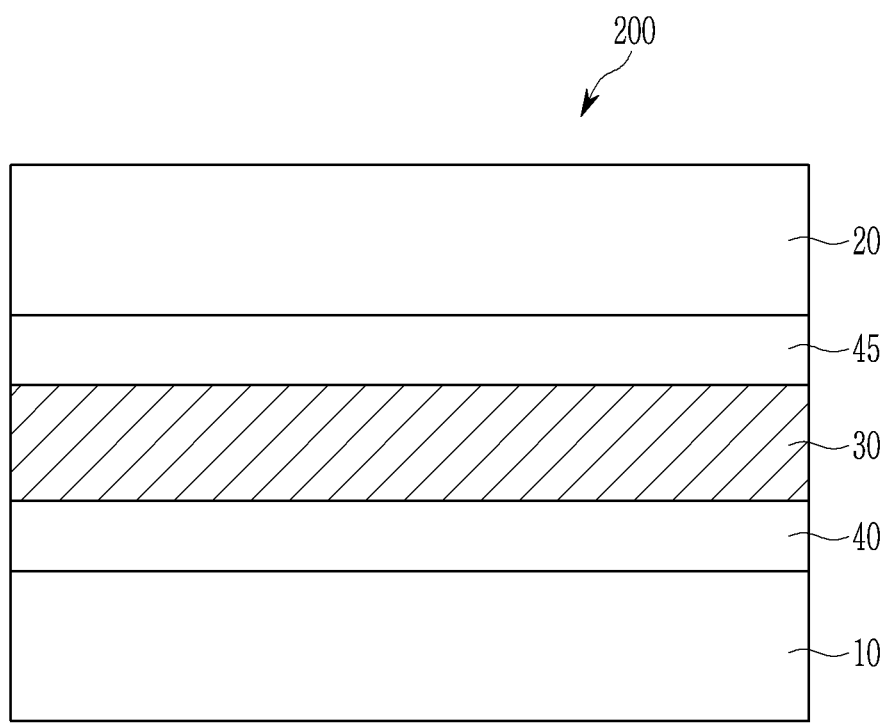
FIG. 2 is a cross-sectional view showing a photoelectric device according to another embodiment.

FIG. 2 is a cross-sectional view showing a photoelectric device according to another example embodiment.

Referring to FIG. 2, a photoelectric device 200 according to the present embodiment includes a first electrode 10 and a second electrode 20 facing each other, and an active layer 30 between the first electrode 10 and the second electrode 20, like the above embodiment.

However, the photoelectric device 200 according to the present embodiment further includes charge auxiliary layers 40 and 45 between the first electrode 10 and the active layer 30, and the second electrode 20 and the active layer 30, unlike the above embodiment. The charge auxiliary layers 40 and 45 may facilitate the transfer of holes and electrons separated from the active layer 30, so as to increase efficiency.

The charge auxiliary layers 40 and 45 may be at least one selected from a hole injection layer (HIL) for facilitating hole injection, a hole transport layer (HTL) for facilitating hole transport, an electron blocking layer (EBL) for limiting and/or preventing electron transport, an electron injection layer (EIL) for facilitating electron injection, an electron transport layer (ETL) for facilitating electron transport, and a hole blocking layer (HBL) for limiting and/or preventing hole transport.

The charge auxiliary layers 40 and 45 may include, for example, an organic material, an inorganic material, or an organic/inorganic material. The organic material may be an organic compound having hole or electron characteristics, and the inorganic material may be, for example, a metal oxide such as molybdenum oxide, tungsten oxide, nickel oxide, and the like.

The hole transport layer (HTL) may include one selected from, for example, poly(3,4-ethylenedioxythiophene):poly (styrenesulfonate) (PEDOT:PSS), polyarylamine, poly(N-vinylcarbazole), polyaniline, polypyrrole, N,N,N',N'-tetrakis(4-methoxyphenyl)-benzidine (TPD), 4-bis[N-(1-naphthyl)-N-phenyl-amino]biphenyl (α-NPD), m-MTDATA, 4,4',4"-tris(N-carbazolyl)-triphenylamine (TCTA), and a combination thereof, but is not limited thereto.

The electron blocking layer (EBL) may include one selected from, for example, poly(3,4-ethylenedioxythiophene):poly(styrenesulfonate) (PEDOT:PSS), polyarylamine, poly(N-vinylcarbazole), polyaniline, polypyrrole, N,N,N',N'-tetrakis(4-methoxyphenyl)-benzidine (TPD), 4,4'-bis[N-(1-naphthyl)-N-phenyl-amino]biphenyl (α-NPD), m-MTDATA, 4,4',4"-tris(N-carbazolyl)-triphenylamine (TCTA), and a combination thereof, but is not limited thereto.

The electron transport layer (ETL) may include one selected from, for example, 1,4,5,8-naphthalene-tetracarboxylic dianhydride (NTCDA), bathocuproine (BCP), LiF, $Alq_3$, $Gaq_3$, $Inq_3$, $Znq_2$, $Zn(BTZ)_2$, $BeBq_2$, and a combination thereof, but is not limited thereto.

The hole blocking layer (HBL) may include one selected from, for example, 1,4,5,8-naphthalene-tetracarboxylic dianhydride (NTCDA), bathocuproine (BCP), LiF, $Alq_3$, $Gaq_3$, $Inq_3$, $Znq_2$, $Zn(BTZ)_2$, $BeBq_2$, and a combination thereof, but is not limited thereto.

Either one of the charge auxiliary layers 40 and 45 may be omitted.

The photoelectric device may be applied to various fields, for example a solar cell, an image sensor, a photo-detector, a photo-sensor, and a light emitting device, but is not limited thereto.

Hereinafter, an example of an image sensor including the photoelectric device is described referring to drawings. As an example of an image sensor, an organic CMOS image sensor is described.

Figure 3:
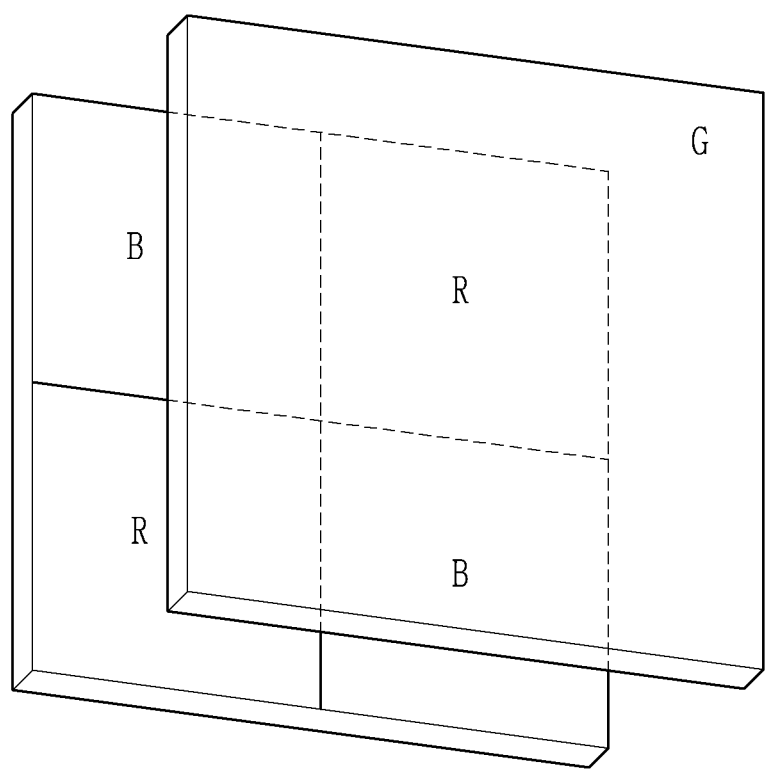
FIG. 3 is a schematic top plan view showing an organic CMOS image sensor according to an example embodiment.
Figure 4:
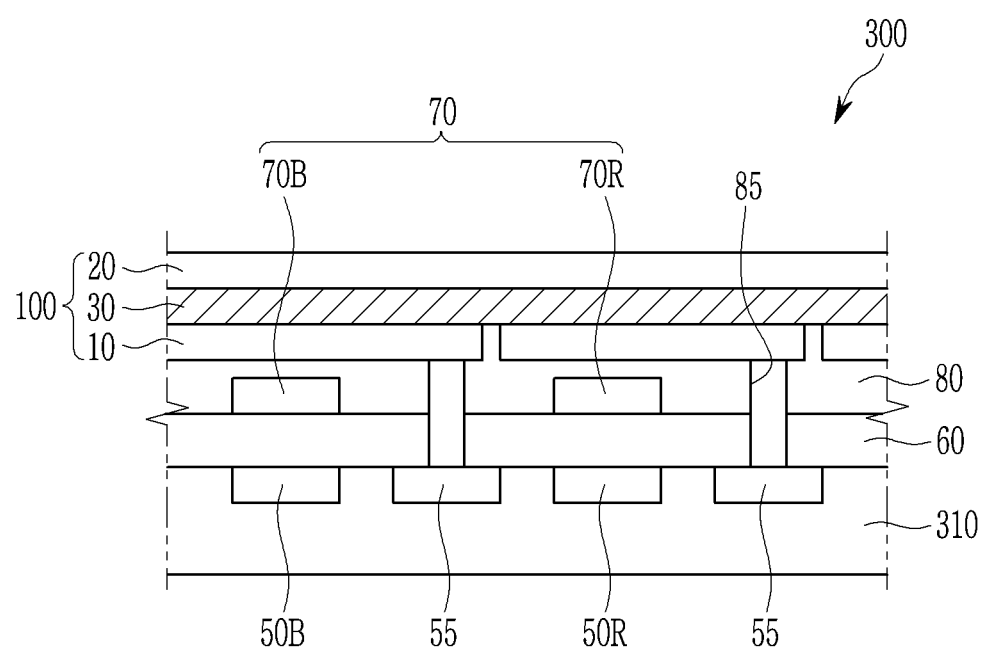
FIG. 4 is a cross-sectional view showing the organic CMOS image sensor of FIG. 3.

FIG. 3 is a schematic top plan view showing an organic CMOS image sensor according to an example embodiment, and FIG. 4 is a cross-sectional view showing the organic CMOS image sensor of FIG. 3.

Referring to FIGS. 3 and 4, an organic CMOS image sensor 300 according to an example embodiment includes a semiconductor substrate 310 integrated with photo-sensing devices 50B and 50R, a transmission transistor (not shown), a charge storage 55, a lower insulation layer 60, a color filter layer 70, an upper insulation layer 80, and a photoelectric device 100.

The semiconductor substrate 310 may be a silicon substrate, and is integrated with the photo-sensing device 50, the transmission transistor (not shown), and the charge storage 55. The photo-sensing devices 50R and 50B may be photodiodes.

The photo-sensing devices 50B and 50R, the transmission transistor, and/or the charge storage 55 may be integrated in each pixel, and as shown in the drawing, the photo-sensing devices 50B and 50R may be respectively included in a blue pixel and a red pixel and the charge storage 55 may be included in a green pixel.

The photo-sensing devices 50B and 50R sense light, the information sensed by the photo-sensing devices may be transferred by the transmission transistor, the charge storage 55 is electrically connected to the photoelectric device 100, and the information of the charge storage 55 may be transferred by the transmission transistor.

In the drawings, the photo-sensing devices 50B and 50R are, for example, arranged in parallel without limitation, and the blue photo-sensing device 50B and the red photo-sensing device 50R may be stacked in a vertical direction.

A metal wire (not shown) and a pad (not shown) are formed on the semiconductor substrate 110. In order to decrease signal delay, the metal wire and pad may be made of a metal having low resistivity, for example, aluminum (Al), copper (Cu), silver (Ag), and alloys thereof, but are not limited thereto. Further, it is not limited to the structure, and the metal wire and pad may be positioned under the photo-sensing devices 50B and 50R.

The lower insulation layer 60 is formed on the metal wire and the pad. The lower insulation layer 60 may be made of an inorganic insulating material such as a silicon oxide and/or a silicon nitride, or a low dielectric constant (low K) material such as SiC, SiCOH, SiCO, and SiOF. The lower insulation layer 60 has a trench exposing the charge storage 55. The trench may be filled with fillers.

A color filter layer 70 is formed on the lower insulation layer 60. The color filter layer 70 includes a blue filter 70B formed in the blue pixel and selectively transmitting blue light and a red filter 70R formed in the red pixel and selectively transmitting red light. In an example embodiment, a cyan filter 70C and a yellow filter 70Y may be disposed instead of the blue filter 70B and the red filter 70R, respectively. In the present embodiment, a green filter is not included, but a green filter may be further included.

The color filter layer 70 may be omitted. For example, when the blue photo-sensing device 50B and the red photo-sensing device 50R are stacked in a vertical direction, the blue photo-sensing device 50B and the red photo-sensing device 50R may selectively absorb light in each wavelength region depending on their stack depth, and the color filter layer 70 may not be equipped.

The upper insulation layer 80 is formed on the color filter layer 70. The upper insulation layer 80 eliminates a step caused by the color filter layer 70 and smoothens the surface. The upper insulation layer 80 and the lower insulation layer 60 may include a contact hole (not shown) exposing a pad, and a through-hole 85 exposing the charge storage 55 of the green pixel.

The photoelectric device 100 is formed on the upper insulation layer 80. The photoelectric device 100 includes the first electrode 10, the active layer 30, and the second electrode 20 as described above.

The first electrode 10 and the second electrode 20 may be transparent electrodes, and the active layer 30 is the same as described above. The active layer 30 selectively absorbs and/or senses light in a green wavelength region and replaces a color filter of a green pixel.

Another color filter layer may be further disposed on the photoelectric device 100. The color filter layer may include a blue filter 70B and a red filter 70R or a cyan filter 70C and a yellow filter.

When light enters from the second electrode 20, the light in a green wavelength region may be mainly absorbed in the active layer 30 and photoelectrically converted, while the light in the rest of the wavelength regions passes through the first electrode 10 and may be sensed in the photo-sensing devices 50B and 50R.

As described above, the photoelectric devices selectively absorbing light in a green wavelength region are stacked and thereby a size of an image sensor may be decreased and a down-sized image sensor may be realized.

As described above, the compound represented by the Chemical Formula 1 may be used as a semiconductor compound, aggregation between compounds in a thin film state is inhibited, and thereby light absorption characteristics depending on a wavelength may be maintained. Thereby, green wavelength selectivity may be maintained, crosstalk caused by unnecessary absorption of other light except a green wavelength region may be decreased and sensitivity may be increased.

In an embodiment, in FIG. 4, another color filter layer may be further disposed on the photoelectric device 100. The color filter layer may include a blue filter 70B and a red filter 70R or a cyan filter 70C and a yellow filter.

Figure 5:
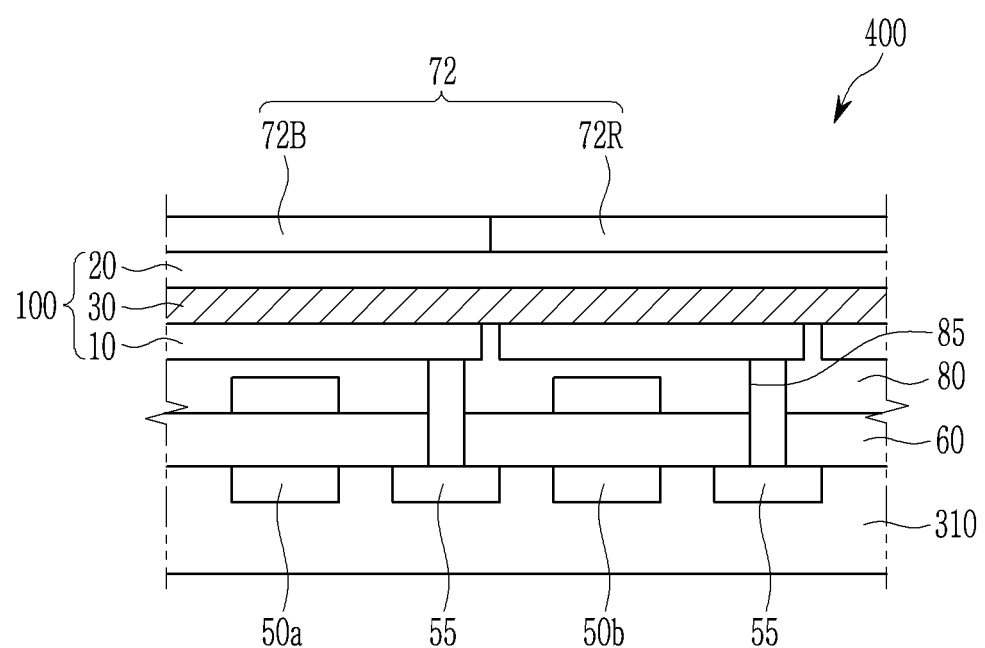
FIG. 5 is a cross-sectional view showing an organic CMOS image sensor according to an example embodiment.

The color filter layer may be disposed on the photoelectric device 100. An organic CMOS image sensor having such a structure is shown in FIG. 5. FIG. 5 is a cross-sectional view showing an organic CMOS image sensor 400 according to an example embodiment. Referring to FIG. 5, the organic CMOS image sensor 400 has the same structure as the organic CMOS image sensor 300 shown in FIG. 4, except that a color filter layer 72 including a blue filter 72B and a red filter 72R is disposed on the photoelectric device 100. In addition, a cyan filter 70C and a yellow filter 72Y may be disposed instead of the blue filter 72B and the red filter 72R, respectively.

Figure 6:
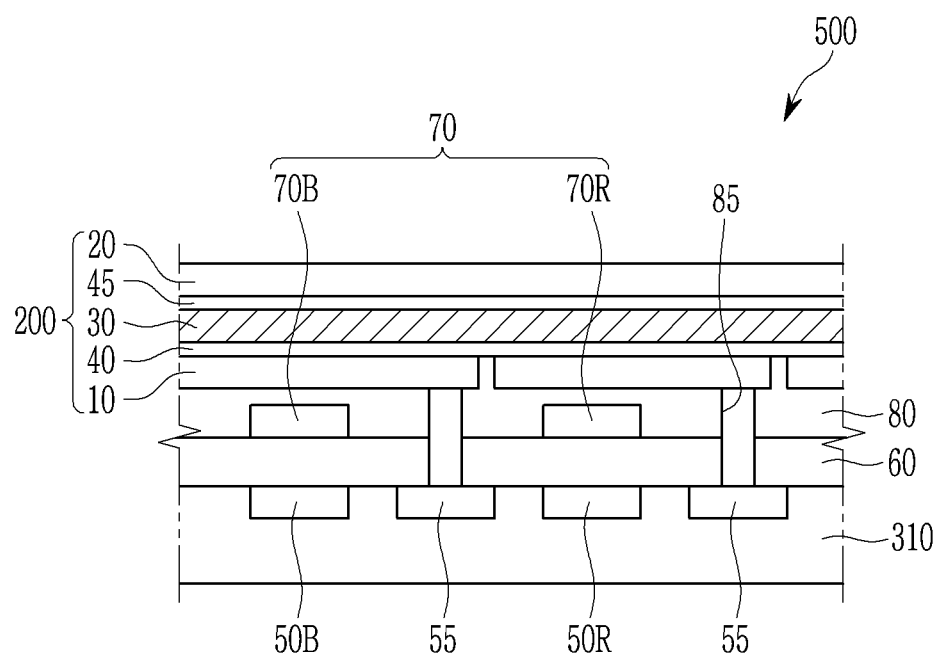
FIG. 6 is a schematic cross-sectional view showing an organic CMOS image sensor according to another example embodiment.

In FIGS. 4 and 5, the photoelectric device 100 of FIG. 1 is included, but it is not limited thereto, and thus the photoelectric device 200 of FIG. 2 may be applied in the same manner. FIG. 6 shows a structure of an image sensor having such a structure, and is a cross-sectional view of an organic CMOS image sensor 500 including the photoelectric device 200 in FIG. 2.

Figure 7:
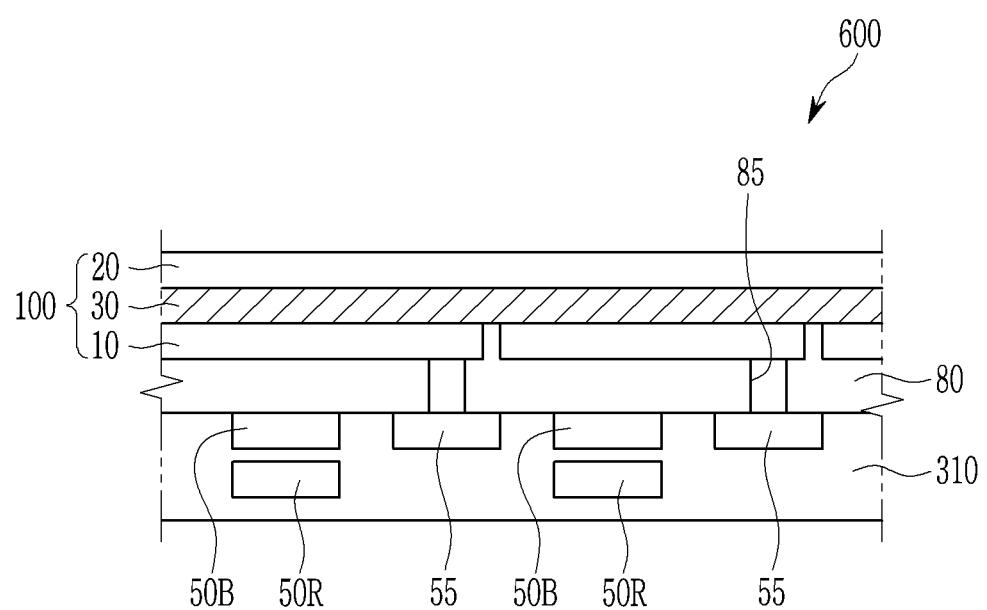
FIG. 7 is a schematic cross-sectional view showing an organic CMOS image sensor according to another example embodiment.

FIG. 7 is a cross-sectional view showing the organic CMOS image sensor according to another example embodiment.

Referring to FIG. 7, the organic CMOS image sensor 600 includes a semiconductor substrate 310 integrated with photo-sensing devices 50B and 50R, a transmission transistor (not shown), and a charge storage 55, an insulation layer 80, and a photoelectric device 100, like the example embodiment illustrated in FIG. 5.

However, the organic CMOS image sensor 600 according to the example embodiment illustrated in FIG. 7 includes the blue photo-sensing device 50B and the red photo-sensing device 50R that are stacked and does not include a color filter layer 70, unlike the example embodiment illustrated in FIG. 6. The blue photo-sensing device 50B and the red photo-sensing device 50R are electrically connected with the charge storage 55, and the information of the charge storage 55 may be transferred by the transmission transistor (not shown). The blue photo-sensing device 50B and the red photo-sensing device 50R may selectively absorb light in each wavelength region depending on a stack depth.

As described above, the photoelectric devices selectively absorbing light in a green wavelength region are stacked and the red photo-sensing device and the blue photo-sensing device are stacked, and thereby a size of an image sensor may be decreased and a down-sized image sensor may be realized. As described above, the photoelectric device 100 has improved green wavelength selectivity, and crosstalk caused by unnecessary absorption of other light except a green wavelength region may be decreased while increasing sensitivity.

In FIG. 7, the photoelectric device 100 of FIG. 1 is included, but it is not limited thereto, and thus the photoelectric device 200 of FIG. 2 may be applied in the same manner.

Figure 8:
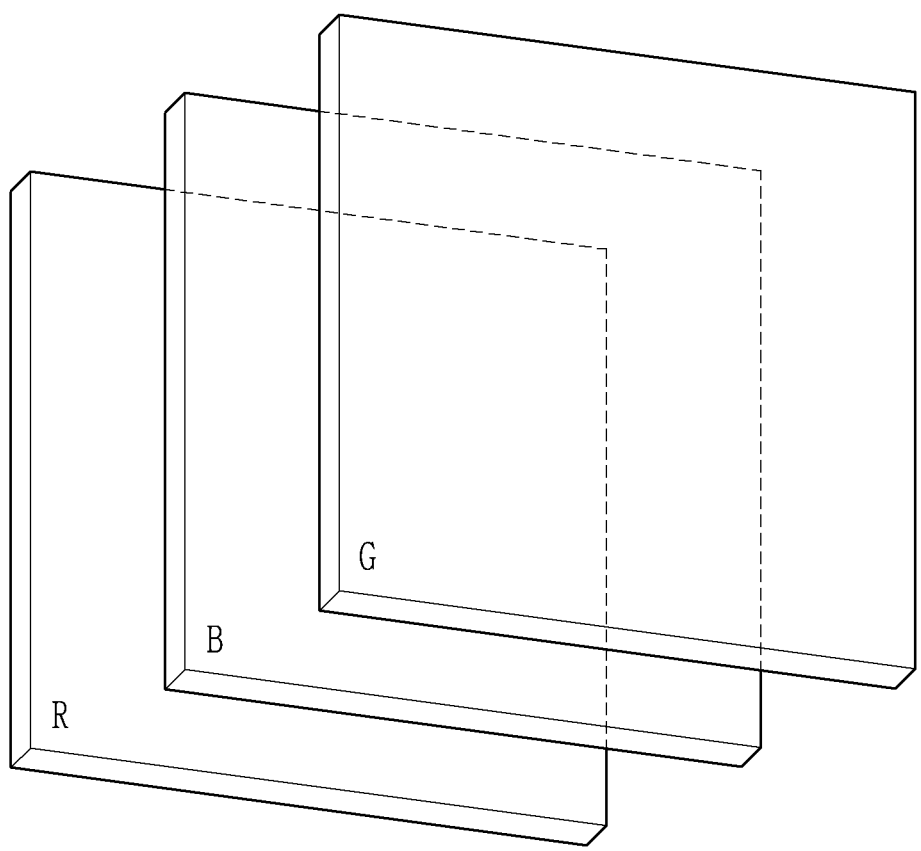
FIG. 8 is a schematic view showing an organic CMOS image sensor according to another example embodiment.

FIG. 8 is a schematic view showing an organic CMOS image sensor according to another example embodiment.

Referring to FIG. 8, the organic CMOS image sensor according to the present embodiment includes a green photoelectric device (G) selectively absorbing light in a green wavelength region, a blue photoelectric device (B) selectively absorbing light in a blue wavelength region, and a red photoelectric device (R) selectively absorbing light in a red wavelength region that are stacked.

In the drawing, the red photoelectric device (R), the blue photoelectric device (B) and the green photoelectric device (G) are sequentially stacked, but the stack order may be changed without limitation.

The green photoelectric device (G) may be the above photoelectric device 100 or photoelectric device 200, the blue photoelectric device (B) may include electrodes facing each other and an active layer interposed therebetween and including an organic material selectively absorbing light in a blue wavelength region, the red photoelectric device (R) may include electrodes facing each other and an active layer interposed therebetween and including an organic material selectively absorbing light in a red wavelength region.

As described above, the green photoelectric device (G) selectively absorbing light in a green wavelength region, the blue photoelectric device (B) selectively absorbing light in a blue wavelength region, and the photoelectric device (R) selectively absorbing light in a red wavelength region are stacked, and thereby a size of an image sensor may be decreased and a down-sized image sensor may be realized, and also sensitivity may be increased and crosstalk may be reduced.

The image sensor may be applied to various electronic devices, for example, a mobile phone, a digital camera, and the like but is not limited thereto.

Figure 9:
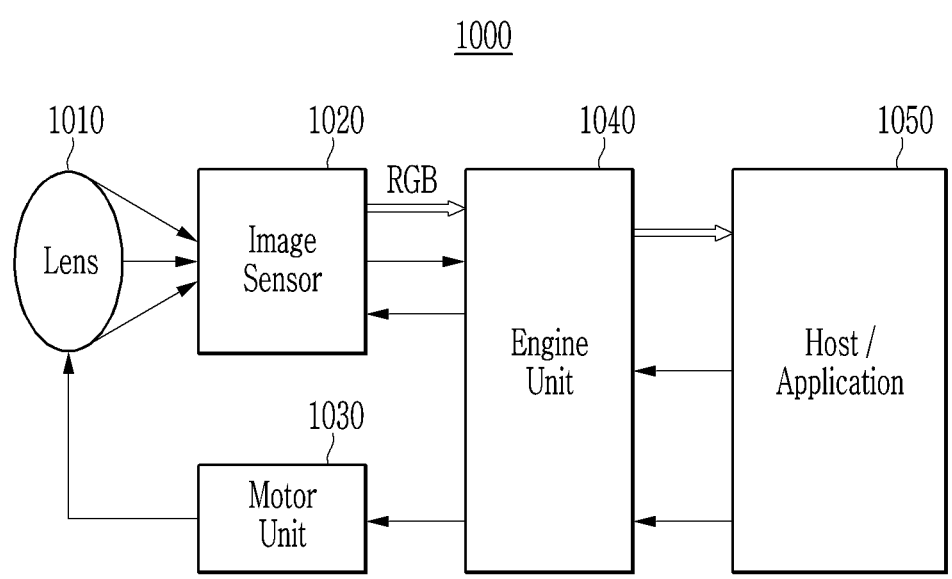
FIG. 9 is a block diagram of a digital camera including an image sensor according to an embodiment.

FIG. 9 is a block diagram of a digital camera including an image sensor according to an embodiment.

Referring to FIG. 9, a digital camera 1000 includes a lens 1010, an image sensor 1020, a motor unit 1030, and an engine unit 1040. The image sensor 1020 may be one of image sensors according to embodiments shown in FIGS. 3 to 8.

The lens 1010 concentrates incident light on the image sensor 1020. The image sensor 1020 generates RGB data for received light through the lens 1010.

In some embodiments, the image sensor 1020 may interface with the engine unit 1040. The motor unit 1030 may adjust the focus of the lens 1010 or perform shuttering in response to a control signal received from the engine unit 1040. The engine unit 1040 may control the image sensor 1020 and the motor unit 1030.

The engine unit 1040 may be connected to a host/application 1050.

Hereinafter, the embodiments are illustrated in more detail with reference to examples. However, inventive concepts are not limited thereto.

Synthesis Example 1: Synthesis of Compound Represented by Chemical Formula 1A (2-(4-10H-phenoselenazin-10-yl)benxylidene)-1H-cyclopenta[b]naphthalene-1,3(2H)-dione)

[Chemical Formula 1A]

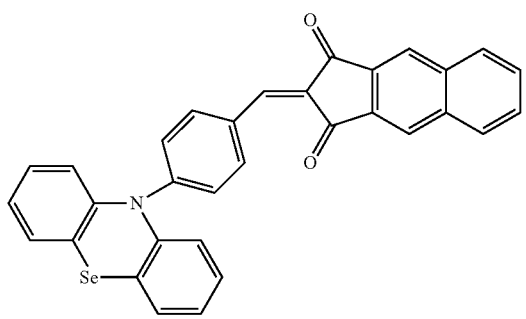

[Reaction Scheme 1A]

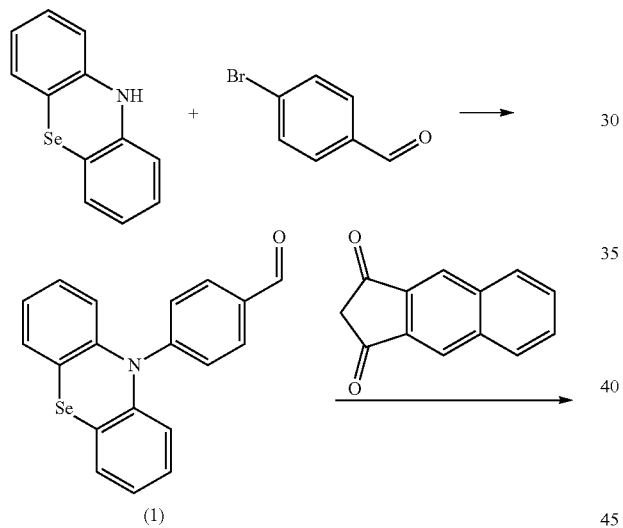

1A (i) Synthesis of Compound 1

10H-phenoselenazine (7.03 g, 28.55 mmol) and p-bromobenzaldehyde (6.34 g, 34.26 mmol) are put in a 2-necked round-bottomed flask and then, purged with $N_2$ gas. Subsequently, 150 mL of toluene, bis(dibenzylideneacetone)palladium (0) (1.64 g, 2.85 mmol), tri-tert-butylphosphine (1.16 g, 5.71 mmol), and cesium carbonate (27.90 g, 85.65 mmol) are added thereto in a dropwise fashion, and the mixture is refluxed at 105° C. for 12 hours. A product obtained therefrom is separated and purified through silica gel column chromatography (toluene:hexane=a volume ratio of 1:4) to obtain Compound 1 (5 g, a yield of 50%).

(ii) Synthesis of Compound Represented by Chemical Formula 1A 1.33 g (3.78 mmol) of Compound (1) and 0.82 g (4.16 mmol) of 1H-cyclopenta[b]naphthalene-1,3(2H)-dione are put in a 2-necked round-bottomed flask and then, fudged with $N_2$ gas. Subsequently, 100 ml of ethanol and piperidine are added thereto in a dropwise fashion, and the mixture is refluxed at 57° C. for 6 hours. The obtained mixture is cooled down to room temperature (25° C.), and water is added thereto. When a powder is formed therein, the powder is filtered and then, purified through column chromatography (eluting solvent: dichloromethane/hexane/ethylacetate). A product therefrom is recrystallized by using dichloromethane and hexane to obtain Compound 1A (1.3 g, yield: 65%).

$^1$H NMR (600 MHz, CDCl$_3$): δ=8.48 (d, 2H), 8.45 (s, 1H), 8.43 (s, 1H), 8.07 (dd, 2H), 7.87 (s, 1H), 7.69 (d, 2H), 7.66 (dd, 2H), 7.64 (d, 2H), 7.46 (t, 2H), 7.28 (t, 2H), 7.01 (d, 2H).

Synthesis Example 2: Synthesis of Compound Represented by Chemical Formula 1B

[Chemical Formula 1B]

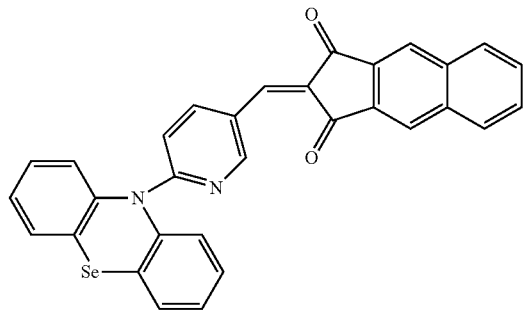

[Reaction Scheme 1B]

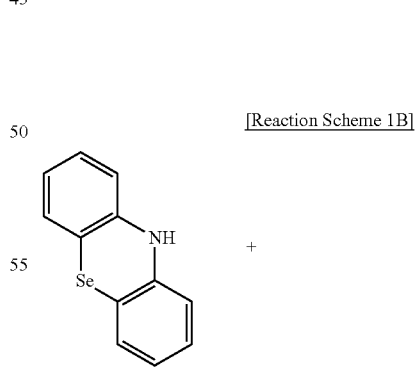

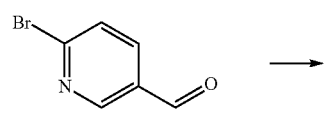

-continued

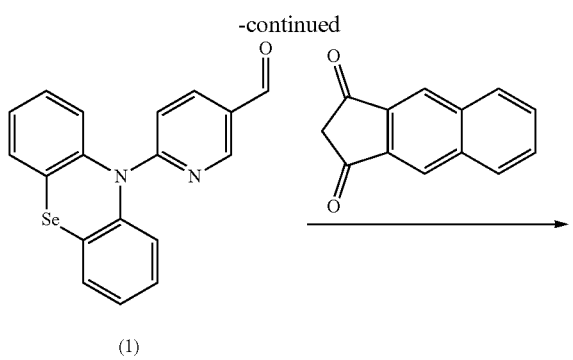

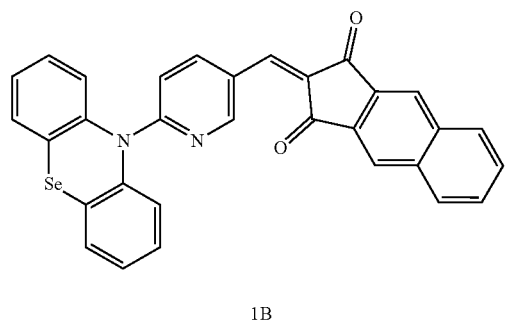

(i) Synthesis of Compound (1)

10H-phenoselenazine (4.91 g, 19.93 mmol) and 6-bromo-3-pyridinecarboxyaldehyde (4.45 g, 23.91 mmol) are put in a 2-necked round-bottomed flask and then, purged with $N_2$ gas. Subsequently, 150 mL of toluene, bis(dibenzylideneacetone)palladium (0) (1.15 g, 1.99 mmol), tri-tert-butylphosphine (0.80 g, 3.99 mmol), and cesium carbonate (19.48 g, 59.78 mmol) are added thereto in a dropwise fashion, and the obtained mixture is refluxed at 100° C. to 110° C. for 12 hours. A product obtained therefrom is separated and purified through silica gel column chromatography (toluene:hexane=a volume ratio of 1:4) to obtain Compound (1) (5 g, yield: 71%).

(ii) Synthesis of Compound Represented by Chemical Formula 1B 0.995 g (2.83 mmol) of Compound 1 and 0.61 g (3.12 mmol) of 1H-cyclopenta[b]naphthalene-1,3(2H)-dione are put in a 2-necked round-bottomed flask and then, purged with $N_2$ gas. Subsequently, 100 ml of ethanol and piperidine are added thereto in a dropwise fashion, and the mixture is refluxed at 57° C. for 6 hours. The obtained resultant is cooled down to room temperature (25° C.), and water is added thereto. When a powder is formed there, the powder is filtered and purified through column chromatography (eluting solvent: dichloromethane/hexane/ethylacetate). A product obtained therefrom is recrystallized by using dichloromethane and hexane to obtain Compound 1B (1.3 g, yield: 87%).

$^1$H NMR (600 MHz, CDCl$_3$): δ=9.27 (dd, 1H), 8.7 (s, 1H), 8.46 (s, 1H), 8.43 (s, 1H), 8.07 (dd, 2H), 7.82 (s, 1H), 7.74 (d, 2H), 7.67-7.64 (m, 4H), 7.43 (t, 2H), 7.27 (t, 2H), 6.92 (d, 1H).

Comparative Synthesis Example 1: Synthesis of Compound Represented by Chemical Formula 1C

[Chemical Formula 1C]

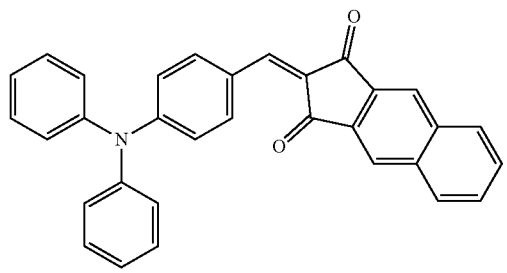

[Reaction Scheme 1C]

(i) Synthesis of Compound Represented by Chemical Formula 1C 4-(N,N-diphenylamino)-benzaldehyde (0.908 g, 3.32 mmol) and 0.72 g (3.65 mmol) of 1H-cyclopenta[b]naphthalene-1,3(2H)-dione are put in a 2-necked round-bottomed flask and then, purged with $N_2$ gas. Subsequently, 100 ml of ethanol and piperidine are added thereto in a dropwise fashion, and the mixture is refluxed at 57° C. for 6 hours. A resultant obtained therefrom is cooled down to room temperature (25° C.), and then, water is added thereto. When a powder is formed, the powder is filtered and purified through column chromatography (eluting solvent: dichloromethane/hexane/ethylacetate). A product therefrom is recrystallized by using dichloromethane and hexane to obtain a compound represented by Chemical Formula 1C (1.3 g, a yield of 87%).

$^1$H NMR (300 MHz, CDCl$_3$): δ=8.49 (d, 2H), 8.36 (d, 2H), 8.06 (dd, 2H), 7.88 (s, 1H), 7.65 (dd, 2H), 7.41-7.2 (m, 10H), 7.01 (d, 2H).

Comparative Synthesis Example 2: Synthesis of Compound Represented by Chemical Formula 1D

[Chemical Formula 1D]

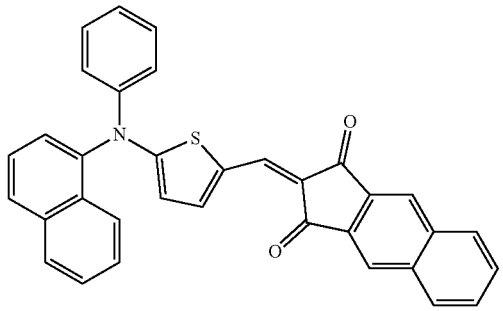

[Reaction Scheme 1D]

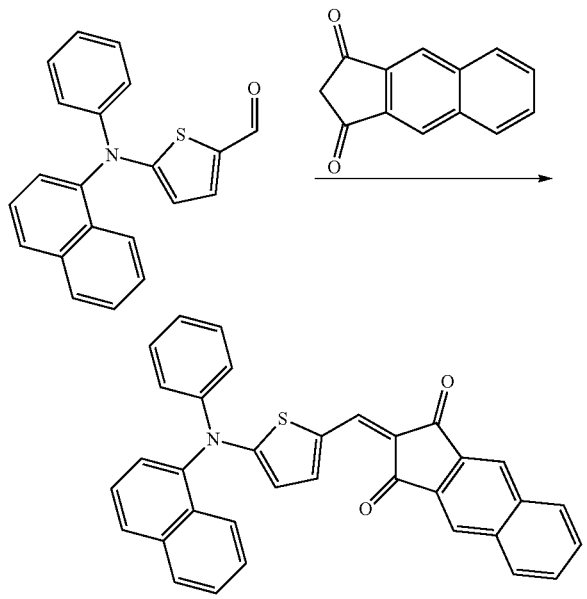

(i) Synthesis of Compound Represented by Chemical Formula 1D 5-(Naphthalen-1-yl(phenyl)amino)thiophene-2-carbaldehyde (1.1 g, 3.35 mmol) and 0.72 g (3.65 mmol) of 1H-cyclopenta[b]naphthalene-1,3(2H)-dione are put in a 2-necked round-bottomed flask and then, purged with $N_2$ gas. Subsequently, 100 ml of ethanol and piperidine are added thereto in a dropwise fashion, and the mixture is refluxed at 57° C. for 6 hours. A resultant therefrom is cooled down to room temperature (25° C.), and water is added thereto. When a powder is formed therein, the powder is filtered and purified through column chromatography (eluting solvent: dichloromethane/hexane/ethylacetate). A product therefrom is recrystallized by using dichloromethane and hexane to obtain a compound represented by Chemical Formula 1D (1.5 g, a yield of 88%)

$^1$H NMR (300 MHz, CDCl$_3$): δ=8.26 (s, 1H), 8.15 (s, 1H), 8.02-7.93 (m, 5H), 7.8 (s, 1H), 7.62-7.51 (m, 8H), 7.41 (t, 2H), 7.29 (t, 2H) 6.38 (d, 1H).

The compounds according to Synthesis Examples 1 and 2 and Comparative Synthesis Examples 1 and 2 along with C60 in a volume ratio of 1:1 are respectively thermally deposited to form a thin film having a thickness of 100 nm under vacuum (<10$^{-7}$ Torr) at a speed of 0.5 to 1.0 Å/s and then, irradiated by an ultraviolet-visible ray (UV-Vis) by using Cary 5000 UV spectroscopy (Varian Inc.) to evaluate light absorption characteristics (a full width at half maximum (FWHM)) and an energy level of each thin film.

The results are shown in Table 1.

TABLE 1

| Compounds | | Full width at half maximum (FWHM) (nm) | HOMO (eV) | LUMO (eV) |
| --- | --- | --- | --- | --- |
| Synthesis Example 1 | Chemical Formula 1A | 94 | −5.70 | −2.61 |
| Synthesis Example 2 | Chemical Formula 1B | 102 | −5.82 | −2.78 |
| Comparative Synthesis Example 1 | Chemical Formula 1C | 105 | −5.53 | −2.69 |
| Comparative Synthesis Example 2 | Chemical Formula 1D | 110 | −5.8 | −3.5 |

Thermal Stability of Compounds According to Synthesis Examples 1 and 2, Comparative Synthesis Examples 1 and 2

Thermal stability of the compounds according to Synthesis Examples 1 and 2 and Comparative Synthesis Examples 1 and 2 is evaluated by measuring a 10 wt % loss temperature (Ts(10%), a deposition temperature) and a 50 wt % loss temperature (Ts(50%), a deposition temperature) at 10 Pa. The loss temperatures are measured in a thermal gravimetric analysis (TGA) method. In addition, a melting point (Tm) of each compound is measured under a normal pressure condition through a differential thermal analysis (DTA, 10° C./min), and a decomposition-starting temperature (Td) thereof is measured through Pyrolysis-GC/MS (Py-GC/MS). The results are shown in Table 2.

TABLE 2

| Compounds | | Tm (° C.) | Ts 10% (° C.) | Ts 50% (° C.) | ΔT (Tm − Ts 50%) (° C.) | Decomposition-starting temperature (Td) (° C.) |
| --- | --- | --- | --- | --- | --- | --- |
| Synthesis Example 1 | Chemical Formula 1A | 333 | 268 | 296 | 37 | 310 |
| Synthesis Example 2 | Chemical Formula 1B | 308 | 261 | 288 | 20 | 290 |
| Comparative Synthesis Example 1 | Chemical Formula 1C | 265 | 225 | 256 | 9 | 250 |
| Comparative Synthesis Example 2 | Chemical Formula 1D | 303 | 259 | 287 | 16 | 240 |

Referring to Table 2, the compounds according to Synthesis Examples 1 and 2 shows a low deposition temperature but a high decomposition-starting temperature and thus leave no residues during the deposition process and may be desirable for a deposition process.

When the compounds have a lower melting point than a deposition temperature through vacuum deposition to form a film, the compounds may be decomposed and simultaneously gasified and thus, hardly formed into a film. Accordingly, the compounds should have a higher melting point than a deposition temperature. The compounds according to Synthesis Examples 1 and 2 have respective 37° C. and 20°

C. of a difference between a melting point and a deposition temperature which are larger than those of Comparative Synthesis Examples 1 and 2. Accordingly, the compounds according to Synthesis Examples 1 and 2 have a larger difference between a melting point and a deposition temperature and thus may advantageously secure process stability during the deposition compared with the compounds according to Comparative Synthesis Examples 1 and 2.

Example 1: Manufacture of Photoelectric Device

An about 150 nm-thick anode is formed by sputtering ITO on a glass substrate, and a 140 nm-thick active layer is formed thereon by codepositing a compound represented by Chemical Formula 1A according to Synthesis Example 1 (a p-type semiconductor compound) and C60 (an n-type semiconductor compound) in a volume ratio of 1:1. Subsequently, a 10 nm-thick molybdenum oxide (MoOx, 0<x≤3) thin film is formed thereon as a charge auxiliary layer. On the molybdenum oxide thin film, a 7 nm-thick cathode is formed by sputtering ITO, manufacturing a photoelectric device.

Example 2: Manufacture of Photoelectric Device

A photoelectric device of Example 2 is manufactured according to the same method as Example 1 except for using the compound according to Synthesis Example 2 instead of the compound according to Synthesis Example 1.

Comparative Example 1 and 2: Manufacture of Photoelectric Devices

Photoelectric devices according to Comparative Examples 1 and 2 are respectively manufactured according to the same method as Example 1 except for respectively using the compound according to Comparative Synthesis Examples 1 and 2 instead of the compound according to Synthesis Example 1.

External Quantum Efficiency (EQE) of Photoelectric Device after Being Annealed at High Temperature The photoelectric devices according to Examples 1 and 2 and Comparative Examples 1 and 2 are measured regarding external quantum efficiency at room temperature (24° C.) and after being annealed at a high temperature. The external quantum efficiency is measured by using an IPCE measurement system (McScience Inc., Korea). First, the IPCE measurement system is calibrated by using a Si photodiode (Hamamatsu Photonics K.K., Japan), the photoelectric devices according to Examples 1 and 2 and Comparative Examples 1 and 2 are respectively equipped thereon, and then, external quantum efficiency (EQE) thereof in a wavelength range of about 350 to about 750 nm is measured. The external quantum efficiency of the photoelectric devices after being annealed at a high temperature of at 160° C. for 1 hour is measured in the same wavelength range of about 350 to about 750 nm by using the same system. An EQE maintenance rate after being annealed at a high temperature is calculated according to Equation 1 and evaluated. The results are shown in Table 3.

[Equation 1]

$$\left(\frac{EQE \text{ after being annealed at a high temperature}}{EQE \text{ at room temperature}}\right) \times 100$$

TABLE 3

| Photoelectric device | Compound | EQE maintenance rate after being annealed (%) (at −3 V) |
|---|---|---|
| Example 1 | Chemical Formula 1A | 115% |
| Example 2 | Chemical Formula 1B | 115% |
| Comparative Example 1 | Chemical Formula 1C | 100% |
| Comparative Example 2 | Chemical Formula 2C | 100% |

As shown in Table 3, the photoelectric devices according to Examples 1 and 2 show 15% increased EQE at room temperature compared with EQE after being annealed at a high temperature. Accordingly, the photoelectric devices according to Examples 1 and 2 show excellent characteristics after being annealed at a high temperature compared with those according to Comparative Examples 1 and 2.

While some example embodiments have been described, it is to be understood that inventive concepts are not limited to the disclosed embodiments, but, on the contrary, inventive concepts are intended to cover various modifications and equivalent arrangements included within the spirit and scope of the appended claims.

DESCRIPTION OF SYMBOLS

| 10: first electrode | 20: second electrode |
|---|---|
| 30: active layer | 40, 45: charge auxiliary layer |
| 100, 200: photoelectric device | |
| 300, 400, 500: organic CMOS image sensor | |
| 310: semiconductor substrate | |
| 70B: blue filter 70R: red filter | |
| 70: color filter layer | 85: through-hole |
| 60: lower insulation layer | 80: upper insulation layer |
| 50B, 50R: photo-sensing device | 55: charge storage |

What is claimed is:
1. A compound represented by Chemical Formula 1:

[Chemical Formula 1]

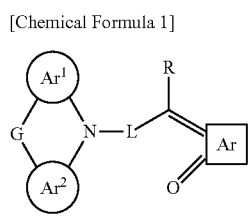

wherein, in Chemical Formula 1,
Ar is one of a substituted or unsubstituted 5-membered aromatic ring group, a substituted or unsubstituted 6-membered aromatic ring group, and a condensed ring of two or more of the foregoing ring groups,
R is one of hydrogen, a substituted or unsubstituted C1 to C30 alkyl group, a substituted or unsubstituted C1 to C30 alkoxy group, a substituted or unsubstituted C6 to C30 aryl group, a substituted or unsubstituted C3 to C30 heteroaryl group, a halogen, a cyano group (—CN), a cyano-containing group, or a combination thereof, L is one of a substituted or unsubstituted C6 to C16 aromatic ring group or a substituted or unsubstituted C3 to C13 N-containing heteroaromatic ring group, $Ar^1$ and $Ar^2$ are independently one of a substituted or unsubstituted C6 to C30 aryl group or a substituted or unsubstituted C3 to C30 heteroaryl group, and G is one of —Se—, —N═, —NR$^a$—, —SiR$^b$R$^c$—, —SiR$^{bb}$R$^{cc}$—, —GeR$^d$R$^e$—, or —GeR$^{dd}$R$^{ee}$— wherein R$^a$, R$^b$, R$^c$, R$^d$, and R$^e$ are independently one of hydrogen, a halogen, or a substituted or unsubstituted C1 to C10 alkyl group, wherein R$^{bb}$, R$^{cc}$, R$^{dd}$, and R$^{ee}$ are independently one of a substituted or unsubstituted C1 to C10 alkyl group, or a substituted or unsubstituted C6 to C10 aryl group, R$^{bb}$ and R$^{cc}$ are linked with each other to provide a ring structure, and R$^{dd}$ and R$^{ee}$ are linked with each other to provide a ring structure.

2. The compound of claim 1, wherein in Chemical Formula 1, L is one of linkers represented by Chemical Formula 2-1:

[Chemical Formula 2-1]

 (1)

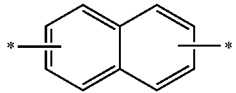 (2)

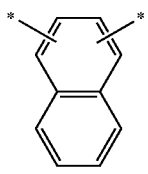 (3)

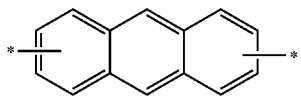 (4)

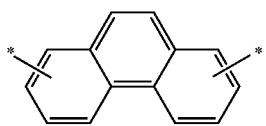 (5)

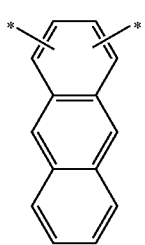 (6)

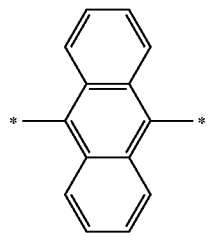 (7)

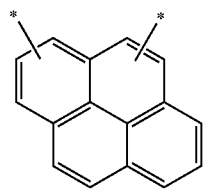 (8)

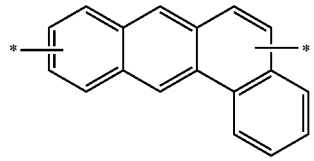 (9)

wherein, in Chemical Formula 2-1, hydrogen of —CH— in each aromatic ring is replaced by a group of a substituted or unsubstituted C1 to C20 alkyl group, a substituted or unsubstituted C1 to C20 alkoxy group, a substituted or unsubstituted C6 to C10 aryl group, a substituted or unsubstituted C4 to C10 heteroaryl group, a halogen, a cyano group (—CN), a cyano-containing group, or a combination thereof, or hydrogen of —CH— in each aromatic ring is not replaced by the group.

3. The compound of claim 1, wherein in Chemical Formula 1, L is one of linkers represented by Chemical Formula 2-2:

[Chemical Formula 2-2]

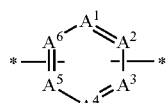 (1)

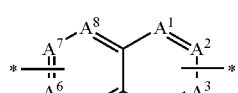 (2)

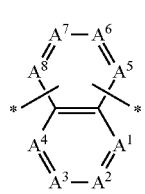 (3)

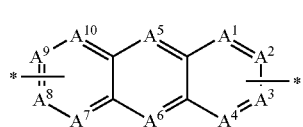 (4)

-continued

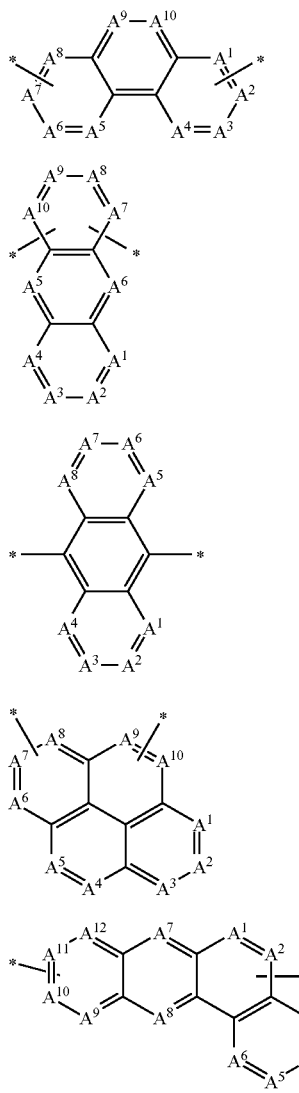

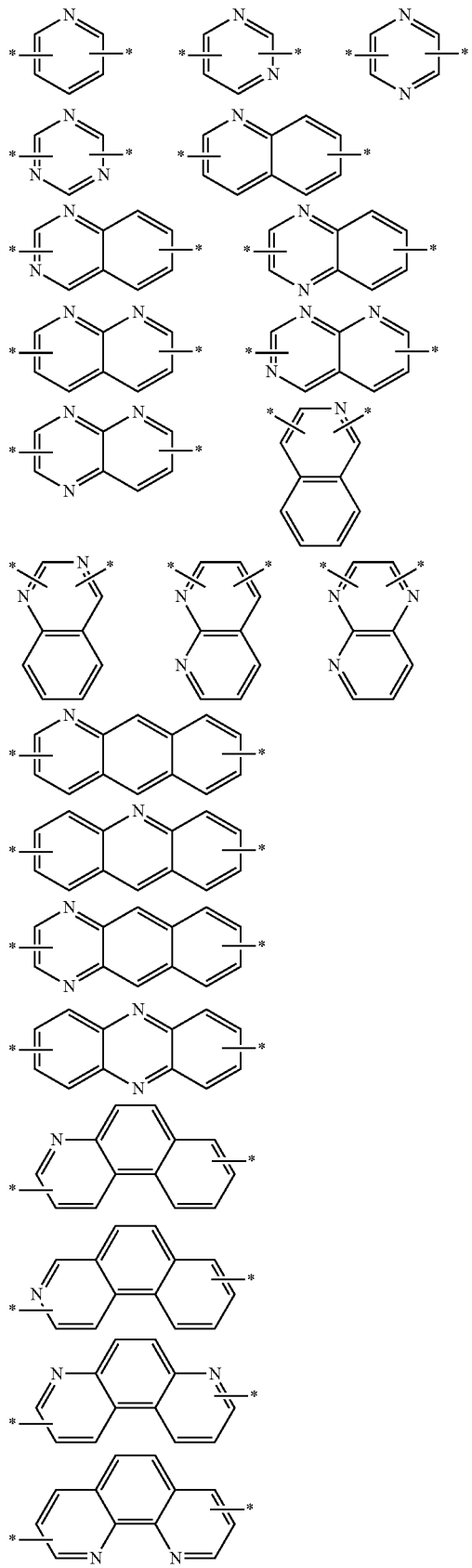

[Chemical Formula 3]

wherein, in Chemical Formula 2-2, $A^1$ to $A^{12}$ are independently N or $CR^a$, wherein, $R^a$ is one of hydrogen, a substituted or unsubstituted C1 to C20 alkyl group, a substituted or unsubstituted C1 to C20 alkoxy group, a substituted or unsubstituted C6 to C10 aryl group, a substituted or unsubstituted C4 to C10 heteroaryl group, a halogen, a cyano group (—CN), a cyano-containing group, or a combination thereof, one to three of $A^1$ to $A^6$ in Chemical Formula (1) are N, one to three of $A^1$ to $A^8$ in Chemical Formulae (2) and (3) are N, one to three of $A^1$ to $A^{10}$ in Chemical Formulae (4) and (6) are N, one to three of $A^1$ to $A^8$ in Chemical Formula (7) are N, one to three of $A^1$ to $A^9$ in Chemical Formula (8) are N, and one to three of $A^1$ to $A^{12}$ in Chemical Formula (9) are N.

4. The compound of claim 1, wherein in Chemical Formula 1, L is one of linkers represented by Chemical Formula 3:

-continued

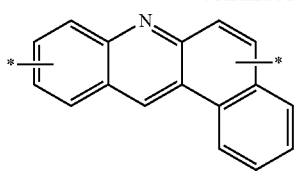

wherein, in Chemical Formula 3,
hydrogen of —CH— in each aromatic ring is replaced by a group of a substituted or unsubstituted C1 to C20 alkyl group, a substituted or unsubstituted C1 to C20 alkoxy group, a substituted or unsubstituted C6 to C10 aryl group, a substituted or unsubstituted C4 to C10 heteroaryl group, a halogen, a cyano group (—CN), a cyano-containing group, or a combination thereof, or
hydrogen of —CH— in each aromatic ring is not replaced by the group.

5. The compound of claim 1, wherein in Chemical Formula 1,
at least one of $Ar^1$ and $Ar^2$ includes a heteroatom at the No. 1 position, and
the heteroatom is one of nitrogen (N), sulfur (S), and selenium (Se).

6. The compound of claim 1, wherein in Chemical Formula 1, the ring group including $Ar^1$ and $Ar^2$ is one of groups of Chemical Formula 4:

[Chemical Formula 4]

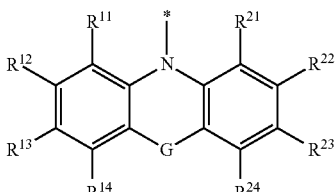

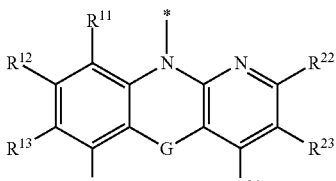

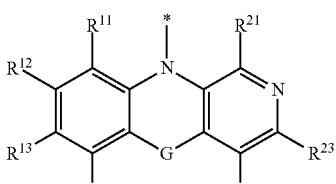

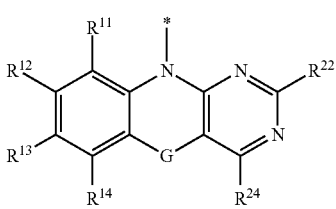

-continued

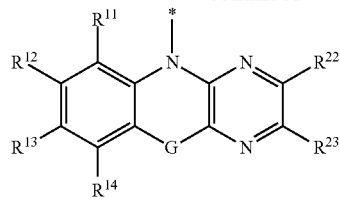

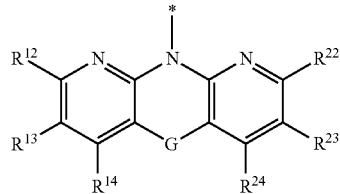

wherein, in Chemical Formula 4,
G is one of —Se—, —N═, —$NR^a$—, —$SiR^bR^c$—, —$SiR^{bb}R^{cc}$—, —$GeR^dR^e$—, or —$GeR^{dd}R^{ee}$— wherein $R^a$, $R^b$, $R^c$, $R^d$, and $R^e$ are independently one of hydrogen, a halogen, or a substituted or unsubstituted C1 to C10 alkyl group, wherein $R^{bb}$, $R^{cc}$, $R^{dd}$, and $R^{ee}$ are independently one of a substituted or unsubstituted C1 to C10 alkyl group, or a substituted or unsubstituted C6 to C10 aryl group, $R^{bb}$ and $R^{cc}$ are linked with each other to provide a ring structure, and $R^{dd}$ and $R^{ee}$ are linked with each other to provide a ring structure, and
$R^{11}$ to $R^{14}$ and $R^{21}$ to $R^{24}$ are independently one of hydrogen, a substituted or unsubstituted C1 to C30 alkyl group, a substituted or unsubstituted C6 to C30 aryl group, a substituted or unsubstituted C3 to C30 heteroaryl group, a halogen, a cyano group (—CN), a cyano-containing group, or a combination thereof,
two adjacent groups of $R^{11}$ to $R^{14}$ are linked with each other to provide a 5-membered aromatic ring or a 6-membered aromatic ring or two adjacent groups of $R^{11}$ to $R^{14}$ are not linked with each other to provide a 5-membered aromatic ring or a 6-membered aromatic ring, and
two adjacent groups of $R^{21}$ to $R^{24}$ are linked with each other to provide a 5-membered aromatic ring or a 6-membered aromatic ring or two adjacent groups of $R^{21}$ to $R^{24}$ are not linked with each other to provide a 5-membered aromatic ring or a 6-membered aromatic ring.

7. The compound of claim 1, wherein in Chemical Formula 1, the Ar-containing ring group is represented by Chemical Formula 5:

[Chemical Formula 5]

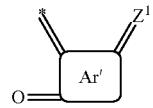

wherein, in Chemical Formula 5,
Ar' is one of a substituted or unsubstituted 5-membered aromatic ring group, a substituted or unsubstituted 6-membered aromatic ring group, and a condensed ring of two or more of the foregoing ring groups, and
$Z^1$ is O or $CR^aR^b$, wherein $R^a$ and $R^b$ are independently one of hydrogen, a substituted or unsubstituted C1 to C10 alkyl group, a cyano group, or a cyano-containing group, provided that at least one of $R^a$ and $R^b$ is a cyano group or a cyano-containing group.

8. The compound of claim 1, wherein in Chemical Formula 1, the Ar-containing ring group is represented by one of Chemical Formulae 5-1 to 5-6:

[Chemical Formula 5-1]

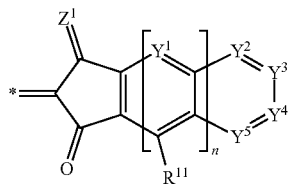

wherein, in Chemical Formula 5-1, $Z^1$ is O or $CR^aR^b$, wherein $R^a$ and $R^b$ are independently one of hydrogen, a substituted or unsubstituted C1 to C10 alkyl group, a cyano group, or a cyano-containing group, provided that at least one of $R^b$ and $R^c$ is a cyano group or a cyano-containing group, $Y^1$ to $Y^5$ are the same or different and are N or $CR^c$, wherein $R^c$ is one of hydrogen, a substituted or unsubstituted C1 to C30 alkyl group, a substituted or unsubstituted C1 to C30 alkoxy group, a substituted or unsubstituted C6 to C30 aryl group, a substituted or unsubstituted C4 to C30 heteroaryl group, a halogen, a cyano group, a cyano-containing group, or a combination thereof, $R^{11}$ is one of hydrogen, a substituted or unsubstituted C1 to C30 alkyl group, a substituted or unsubstituted C6 to C30 aryl group, a substituted or unsubstituted C4 to C30 heteroaryl group, a halogen, a cyano group (—CN), a cyano-containing group, or a combination thereof, n is 0, 1, or 2, and

* indicates a linking position,

[Chemical Formula 5-2]

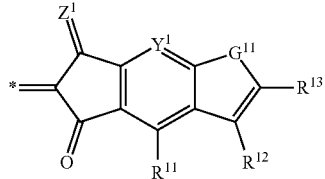

wherein, in Chemical Formula 5-2, $Y^1$ is N or $CR^c$, wherein R is one of hydrogen, a substituted or unsubstituted C1 to C30 alkyl group, a substituted or unsubstituted C1 to C30 alkoxy group, a substituted or unsubstituted C6 to C30 aryl group, a substituted or unsubstituted C4 to C30 heteroaryl group, a halogen, a cyano group, a cyano-containing group, or a combination thereof, $R^{11}$ to $R^{13}$ are the same or different and are one of hydrogen, a substituted or unsubstituted C1 to C30 alkyl group, a substituted or unsubstituted C6 to C30 aryl group, a substituted or unsubstituted C4 to C30 heteroaryl group, a halogen, a cyano group (—CN), a cyano-containing group, or a combination thereof, and $G^{11}$ is one of S, Se, $GeR^xR^y$, or Te, wherein $R^x$ and $R^y$ are the same or different and are independently one of hydrogen, a halogen, a substituted or unsubstituted C1 to C10 alkyl group, or a substituted or unsubstituted C6 to C10 aryl group,

[Chemical Formula 5-3]

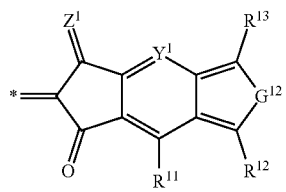

wherein, in Chemical Formula 5-3, $Y^1$ is N or $CR^c$, wherein $R^c$ is one of hydrogen, a substituted or unsubstituted C1 to C30 alkyl group, a substituted or unsubstituted C1 to C30 alkoxy group, a substituted or unsubstituted C6 to C30 aryl group, a substituted or unsubstituted C4 to C30 heteroaryl group, a halogen, a cyano group, a cyano-containing group, or a combination thereof, $R^{11}$ to $R^{13}$ are the same or different and are one of hydrogen, a substituted or unsubstituted C1 to C30 alkyl group, a substituted or unsubstituted C6 to C30 aryl group, a substituted or unsubstituted C4 to C30 heteroaryl group, a halogen, a cyano group (—CN), a cyano-containing group, or a combination thereof, and $G^{12}$ is one of S, Se, $GeR^xR^y$, or Te, wherein $R^x$ and $R^y$ are the same or different and are independently one of hydrogen, a halogen, a substituted or unsubstituted C1 to C10 alkyl group, or a substituted or unsubstituted C6 to C10 aryl group,

[Chemical Formula 5-4]

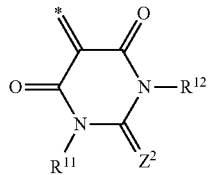

wherein, in Chemical Formula 5-4, $Z^2$ is one of O, S, Se, Te, or $C(R^d)(CN)$, wherein $R^d$ is one of hydrogen, a cyano group (—CN), or a C1 to C10 alkyl group, $R^{11}$ and $R^{12}$ are independently one of hydrogen, a substituted or unsubstituted C1 to C30 alkyl group, a substituted or unsubstituted C1 to C30 alkoxy group, a substituted or unsubstituted C6 to C30 aryl group, a substituted or unsubstituted C4 to C30 heteroaryl group, a halogen, a cyano group (—CN), or a combination thereof, and

* indicates a linking position,

[Chemical Formula 5-5]

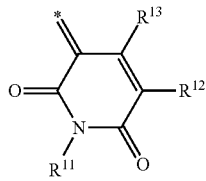

wherein, in Chemical Formula 5-5, $R^{11}$ to $R^{13}$ are independently one of hydrogen, a substituted or unsubstituted C1 to C30 alkyl group, a substituted or unsubstituted C1 to C30 alkoxy group, a substituted or unsubstituted C6 to C30 aryl group, a substituted or unsubstituted C4 to C30 heteroaryl group, a halogen, a cyano group (—CN), a cyano-containing group, or a combination thereof, and

* indicates a linking position,

[Chemical Formula 5-6]

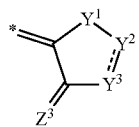

wherein, in Chemical Formula 5-6, $Z^3$ is one of O, S, Se, Te, or $C(R^d)(CN)$, wherein $R^d$ is one of hydrogen, a cyano group (—CN), or a C1 to C10 alkyl group, $Y^1$ is one of O, S, Se, Te, or $GeR^eR^f$ (wherein $R^e$ and $R^f$ are the same or different and are independently one of hydrogen, a halogen, a substituted or unsubstituted C1 to C10 alkyl group, or a substituted or unsubstituted C6 to C10 aryl group), $Y^2$ is one of $CR^h$, C=O, C=S, or $C=(CR^i)(CN)$, $Y^3$ is N or $NR^g$, if $Z^3$ is not oxygen (O), $Y^2$ is C=O, $R^g$, $R^h$, and $R^i$ are independently one of hydrogen, a substituted or unsubstituted C1 to C30 alkyl group, a substituted or unsubstituted C1 to C30 alkoxy group, a substituted or unsubstituted C6 to C30 aryl group, a substituted or unsubstituted C4 to C30 heteroaryl group, a halogen, a cyano group (—CN), a cyano-containing group, or a combination thereof, if $Y^2$ is $CR^h$ or $C=(CR^i)(CN)$ and $Y^3$ is $NR^g$, $Y^2$ and $Y^3$ are linked with each other to provide a $Y^2$-$Y^3$-containing fused ring with the structure represented by Chemical Formula 5-6 or are not a part of a $Y^2$-$Y^3$-containing fused ring with the structure represented by Chemical Formula 5-6, and

* indicates a linking position.

9. The compound of claim 1, wherein the compound exhibits a light absorption curve having a full width at half maximum (FWHM) of about 50 nm to about 120 nm.

10. The compound of claim 1, wherein a temperature (deposition temperature) at which 50 wt % of an initial weight of the compound is lost is greater than or equal to about 280° C.

11. The compound of claim 1, wherein a difference between a melting point of the compound and a temperature (deposition temperature) at which 50 wt % of an initial weight of the compound is lost is greater than or equal to about 10° C.

12. A photoelectric device, comprising:
a first electrode and a second electrode facing each other, and
an active layer between the first electrode and the second electrode,
the active layer including a compound represented by Chemical Formula 1,

[Chemical Formula 1]

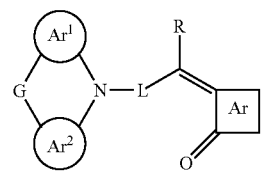

wherein, in Chemical Formula 1,

Ar is one of a substituted or unsubstituted 5-membered aromatic ring group, a substituted or unsubstituted 6-membered aromatic ring group, and a condensed ring of two or more of the foregoing ring groups, R is one of hydrogen, a substituted or unsubstituted C1 to C30 alkyl group, a substituted or unsubstituted C1 to C30 alkoxy group, a substituted or unsubstituted C6 to C30 aryl group, a substituted or unsubstituted C3 to C30 heteroaryl group, a halogen, a cyano group (—CN), a cyano-containing group, or a combination thereof, L is one of a substituted or unsubstituted C6 to C16 aromatic ring group or a substituted or unsubstituted C3 to C13 N-containing heteroaromatic ring group, $Ar^1$ and $Ar^2$ are independently one of a substituted or unsubstituted C6 to C30 aryl group or a substituted or unsubstituted C3 to C30 heteroaryl group, and G is one of —Se—, —N=, —$NR^a$—, —$SiR^bR^c$—, —$SiR^{bb}R^{cc}$—, —$GeR^dR^e$—, or —$GeR^{dd}R^{ee}$— wherein $R^a$, $R^b$, $R^c$, $R^d$, and $R^e$ are independently one of hydrogen, a halogen, or a substituted or unsubstituted C1 to C10 alkyl group, wherein $R^{bb}$, $R^{cc}$, $R^{dd}$, and $R^{ee}$ are independently one of a substituted or unsubstituted C1 to C10 alkyl group, or a substituted or unsubstituted C6 to C10 aryl group, $R^{bb}$ and $R^{cc}$ are linked with each other to provide a ring structure, and $R^{dd}$ and $R^{ee}$ are linked with each other to provide a ring structure.

13. The photoelectric device of claim 12, wherein in Chemical Formula 1, L is one of linkers represented by Chemical Formula 2-1:

[Chemical Formula 2-1]

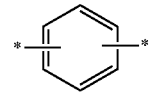

(1)

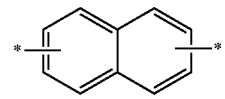

(2)

-continued (3)

(4)

(5)

(6)

(7)

(8)

(9)

wherein, in Chemical Formula 2-1,
hydrogen of —CH— in each aromatic ring is replaced by a group of a substituted or unsubstituted C1 to C20 alkyl group, a substituted or unsubstituted C1 to C20 alkoxy group, a substituted or unsubstituted C6 to C10 aryl group, a substituted or unsubstituted C4 to C10 heteroaryl group, a halogen, a cyano group (—CN), a cyano-containing group, or a combination thereof, or
hydrogen of —CH— in each aromatic ring is not replaced by the group.

14. The photoelectric device of claim 12, wherein in Chemical Formula 1, L is one of linkers represented by Chemical Formula 2-2:

[Chemical Formula 2-2]

(1)

(2)

(3)

(4)

(5)

(6)

(7)

(8)

-continued (9)
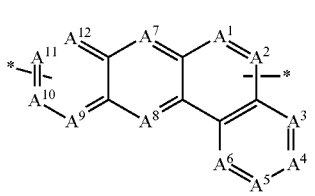

wherein, in Chemical Formula 2-2,
$A^1$ to $A^{12}$ are independently N or $CR^a$, wherein $R^a$ is hydrogen, a substituted or unsubstituted C1 to C20 alkyl group, a substituted or unsubstituted C1 to C20 alkoxy group, a substituted or unsubstituted C6 to C10 aryl group, a substituted or unsubstituted C4 to C10 heteroaryl group, a halogen, a cyano group (—CN), a cyano-containing group, or a combination thereof,
one to three of $A^1$ to $A^6$ in Chemical Formula (1) are N,
one to three of $A^1$ to $A^8$ in Chemical Formulae (2) and (3) are N,
one to three of $A^1$ to $A^{10}$ in Chemical Formulae (4) and (6) are N,
one to three of $A^1$ to $A^8$ in Chemical Formula (7) are N,
one to three of $A^1$ to $A^9$ in Chemical Formula (8) are N, and
one to three of $A^1$ to $A^{12}$ in Chemical Formula (9) are N.

15. The photoelectric device of claim 12, wherein in Chemical Formula 1, L is one of linkers represented by Chemical Formula 3:

[Chemical Formula 3]

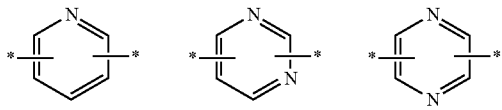
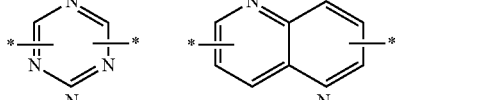
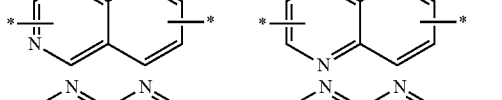
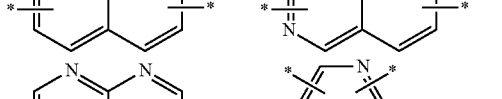
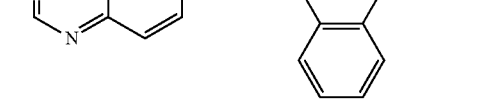

-continued

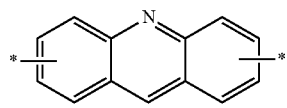
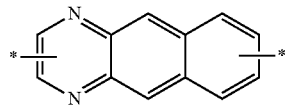
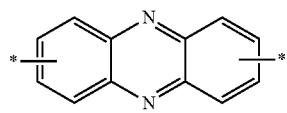
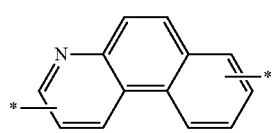
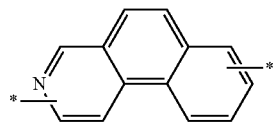
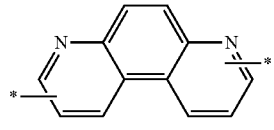
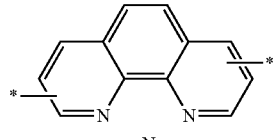
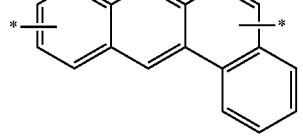

wherein, in Chemical Formula 3,
hydrogen of —CH— in each aromatic ring is replaced by a group of a substituted or unsubstituted C1 to C20 alkyl group, a substituted or unsubstituted C1 to C20 alkoxy group, a substituted or unsubstituted C6 to C10 aryl group, a substituted or unsubstituted C4 to C10 heteroaryl group, a halogen, a cyano group (—CN), a cyano-containing group, or a combination thereof, or
hydrogen of —CH— in each aromatic ring is not replaced by the group.

16. The photoelectric device of claim 12, wherein in Chemical Formula 1,
at least one of $Ar^1$ and $Ar^2$ includes a heteroatom at the No. 1 position, and
the heteroatom is one of nitrogen (N), sulfur (S), and selenium (Se).

17. The photoelectric device of claim 12, wherein in Chemical Formula 1, $Ar^1$ and $Ar^2$ are one of groups of Chemical Formula 4:

[Chemical Formula 4]

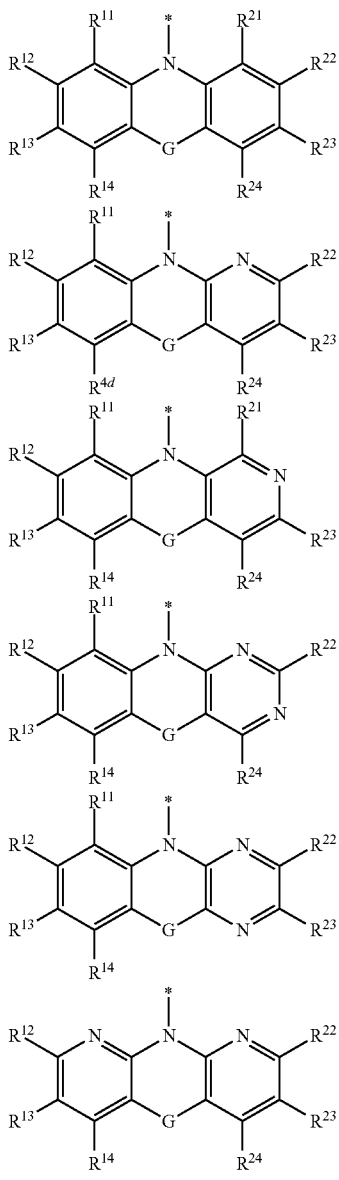

wherein, in Chemical Formula 4,

G is one of —Se—, —N═, —NR$^a$—, —SiR$^b$R$^c$—, —SiR$^{bb}$R$^{cc}$—, —GeR$^d$R$^e$—, or —GeR$^{dd}$R$^{ee}$— wherein R$^a$, R$^b$, R$^c$, R$^d$, and R$^e$ are independently one of hydrogen, a halogen, or a substituted or unsubstituted C1 to C10 alkyl group, wherein R$^{bb}$, R$^{cc}$, R$^{dd}$, and R$^{ee}$ are independently one of a substituted or unsubstituted C1 to C10 alkyl group, or a substituted or unsubstituted C6 to C10 aryl group, R$^{bb}$ and R$^{cc}$ are linked with each other to provide a ring structure, and R$^{dd}$ and R$^{ee}$ are linked with each other to provide a ring structure, and R$^{11}$ to R$^{14}$ and R$^{21}$ to R$^{24}$ are independently one of hydrogen, a substituted or unsubstituted C1 to C30 alkyl group, a substituted or unsubstituted C6 to C30 aryl group, a substituted or unsubstituted C3 to C30 heteroaryl group, a halogen, a cyano group (—CN), a cyano-containing group, or a combination thereof, two adjacent groups of R$^{11}$ to R$^{14}$ are linked with each other to provide a 5-membered aromatic ring or a 6-membered aromatic ring or two adjacent groups of R$^{11}$ to R$^{14}$ are not linked with each other to provide a 5-membered aromatic ring or a 6-membered aromatic ring, and two adjacent groups of R$^{21}$ to R$^{24}$ are linked with each other to provide a 5-membered aromatic ring or a 6-membered aromatic ring or two adjacent groups of R$^{21}$ to R$^{24}$ are not linked with each other to provide a 5-membered aromatic ring or a 6-membered aromatic ring.

18. The photoelectric device of claim 12, wherein in Chemical Formula 1, Ar-containing ring group is represented by Chemical Formula 5:

[Chemical Formula 5]

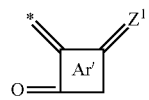

wherein, in Chemical Formula 5,

Ar' is one of a substituted or unsubstituted 5-membered aromatic ring group, a substituted or unsubstituted 6-membered aromatic ring group, and a condensed ring of two or more of the foregoing ring groups, and Z$^1$ is O or CR$^a$R$^b$, wherein R$^a$ and R$^b$ are independently one of hydrogen, a substituted or unsubstituted C1 to C10 alkyl group, a cyano group, or a cyano-containing group, provided that at least one of R$^a$ and R$^b$ is a cyano group or a cyano-containing group.

19. The photoelectric device of claim 12, wherein in Chemical Formula 1, the Ar-containing ring group is represented by one of Chemical Formulae 5-1 to 5-6:

[Chemical Formula 5-1]

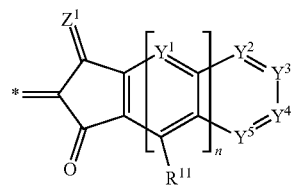

wherein, in Chemical Formula 5-1,

Z$^1$ is O or CR$^a$R$^b$ (wherein R$^a$ and R$^b$ are independently one of hydrogen, a substituted or unsubstituted C1 to C10 alkyl group, a cyano group, or a cyano-containing group, provided that at least one of R$^b$ and R$^c$ is a cyano group or a cyano-containing group), Y$^1$ to Y$^5$ are the same or different and are one of N and CR, wherein R$^c$ is one of hydrogen, a substituted or unsubstituted C1 to C30 alkyl group, a substituted or unsubstituted C1 to C30 alkoxy group, a substituted or unsubstituted C6 to C30 aryl group, a substituted or unsubstituted C4 to C30 heteroaryl group, a halogen, a cyano group, a cyano-containing group, or a combination thereof, R$^{11}$ is one of hydrogen, a substituted or unsubstituted C1 to C30 alkyl group, a substituted or unsubstituted C6 to C30 aryl group, a substituted or unsubstituted C4 to C30 heteroaryl group, a halogen, a cyano group (—CN), a cyano-containing group, or a combination thereof, n is 0, 1 or 2, and

* indicates a linking position,

[Chemical Formula 5-2]

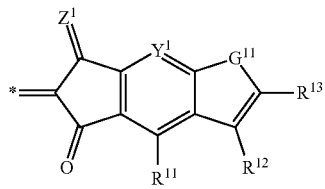

wherein, in Chemical Formula 5-2, $Y^1$ is N or $CR^c$, wherein R is one of hydrogen, a substituted or unsubstituted C1 to C30 alkyl group, a substituted or unsubstituted C1 to C30 alkoxy group, a substituted or unsubstituted C6 to C30 aryl group, a substituted or unsubstituted C4 to C30 heteroaryl group, a halogen, a cyano group, a cyano-containing group, or a combination thereof, $R^{11}$ to $R^{13}$ are the same or different and are one of hydrogen, a substituted or unsubstituted C1 to C30 alkyl group, a substituted or unsubstituted C6 to C30 aryl group, a substituted or unsubstituted C4 to C30 heteroaryl group, a halogen, a cyano group (—CN), a cyano-containing group, or a combination thereof, and $G^{11}$ is one of S, Se, $GeR^xR^y$, or Te, wherein $R^x$ and $R^y$ are the same or different and are independently one of hydrogen, a halogen, a substituted or unsubstituted C1 to C10 alkyl group, or a substituted or unsubstituted C6 to C10 aryl group,

[Chemical Formula 5-3]

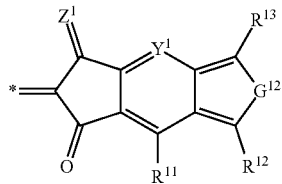

wherein, in Chemical Formula 5-3, $Y^1$ is N or $CR^c$, wherein $R^c$ is one of hydrogen, a substituted or unsubstituted C1 to C30 alkyl group, a substituted or unsubstituted C1 to C30 alkoxy group, a substituted or unsubstituted C6 to C30 aryl group, a substituted or unsubstituted C4 to C30 heteroaryl group, a halogen, a cyano group, a cyano-containing group, or a combination thereof, $R^{11}$ to $R^{13}$ are the same or different and are one of hydrogen, a substituted or unsubstituted C1 to C30 alkyl group, a substituted or unsubstituted C6 to C30 aryl group, a substituted or unsubstituted C4 to C30 heteroaryl group, a halogen, a cyano group (—CN), a cyano-containing group, or a combination thereof, and $G^{12}$ is one of S, Se, $GeR^xR^y$, or Te, wherein $R^x$ and $R^y$ are the same or different and are independently one of hydrogen, a halogen, a substituted or unsubstituted C1 to C10 alkyl group, or a substituted or unsubstituted C6 to C10 aryl group,

[Chemical Formula 5-4]

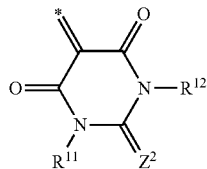

wherein, in Chemical Formula 5-4, $Z^2$ is one of O, S, Se, Te, or $C(R^d)(CN)$, wherein $R^d$ is one of hydrogen, a cyano group (—CN), or a C1 to C10 alkyl group, $R^{11}$ and $R^{12}$ are independently one of hydrogen, a substituted or unsubstituted C1 to C30 alkyl group, a substituted or unsubstituted C1 to C30 alkoxy group, a substituted or unsubstituted C6 to C30 aryl group, a substituted or unsubstituted C4 to C30 heteroaryl group, a halogen, a cyano group (—CN), or a combination thereof, and

* indicates a linking position,

[Chemical Formula 5-5]

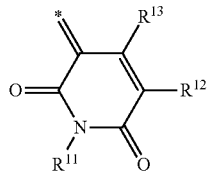

wherein, in Chemical Formula 5-5, $R^{11}$ to $R^{13}$ are independently one of hydrogen, a substituted or unsubstituted C1 to C30 alkyl group, a substituted or unsubstituted C1 to C30 alkoxy group, a substituted or unsubstituted C6 to C30 aryl group, a substituted or unsubstituted C4 to C30 heteroaryl group, a halogen, a cyano group (—CN), a cyano-containing group, or a combination thereof, and

* indicates a linking position,

[Chemical Formula 5-6]

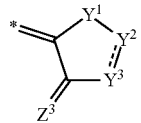

wherein, in Chemical Formula 5-6, $Z^3$ is one of O, S, Se, Te, or $C(R^d)(CN)$, wherein $R^d$ is one of hydrogen, a cyano group (—CN), or a C1 to C10 alkyl group, $Y^1$ is one of O, S, Se, Te, or $GeR^eR^f$ (wherein $R^e$ and $R^f$ are the same or different and are independently one of hydrogen, a halogen, a substituted or unsubstituted C1 to C10 alkyl group, or a substituted or unsubstituted C6 to C10 aryl group), $Y^2$ is one of $CR^h$, C=O, C=S, or C=$(CR^i)(CN)$, $Y^3$ is N or $NR^g$, if $Z^3$ is not oxygen (O), $Y^2$ is C=O, $R^g$, $R^h$, and $R^i$ are independently one of hydrogen, a substituted or unsubstituted C1 to C30 alkyl group, a substituted or unsubstituted C1 to C30 alkoxy group, a substituted or unsubstituted C6 to C30 aryl group, a substituted or unsubstituted C4 to C30 heteroaryl group, a halogen, a cyano group (—CN), a cyano-containing group, or a combination thereof, if $Y^2$ is $CR^h$ or $C=(CR^i)(CN)$ and $Y^3$ is $NR^g$, $Y^2$ and $Y^3$ are linked with each other to provide a $Y^2$-$Y^3$-containing fused ring with the structure (a pentagonal ring) represented by Chemical Formula 5-6 or are not a part of a $Y^2$-$Y^3$-containing fused ring with the structure represented by Chemical Formula 5-6, and

* indicates a linking position.

20. The photoelectric device of claim 12, wherein the active layer exhibits a light absorption curve having a full width at half maximum (FWHM) of about 50 nm to about 120 nm.

21. An image sensor comprising:
the photoelectric device of claim 12.

22. The image sensor of claim 21, wherein the image sensor includes a semiconductor substrate integrated with a plurality of first photo-sensing devices sensing light in a blue wavelength region and a plurality of second photo-sensing devices sensing light in a red wavelength region, and the photoelectric device is on the semiconductor substrate and selectively sensing light in a green wavelength region.

23. The image sensor of claim 22, wherein
the image sensor further includes a color filter layer, and
the color filter layer includes a blue filter selectively transmitting light in a blue wavelength region and a red filter selectively transmitting light in a red wavelength region.

24. The image sensor of claim 22, wherein the first photo-sensing device and the second photo-sensing device are stacked in a vertical direction in the semiconductor substrate.

25. The image sensor of claim 21, wherein the image sensor includes a green photoelectric device of the photoelectric device, a blue photoelectric device selectively absorbing light in a blue wavelength region, and a red photoelectric device selectively absorbing light in a red wavelength region that are stacked.

26. An electronic device comprising:
the image sensor of claim 21.

* * * * *